US006673827B1

(12) United States Patent
Brouillette et al.

(10) Patent No.: US 6,673,827 B1
(45) Date of Patent: Jan. 6, 2004

(54) METHODS OF TREATING FUNGAL INFECTIONS WITH INHIBITORS OF NAD SYNTHETASE ENZYME

(75) Inventors: Wayne J. Brouillette, Pelham, AL (US); Christie G. Brouillette, Pelham, AL (US); Lawrence J. DeLucas, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 29 days.

(21) Appl. No.: 09/606,256

(22) Filed: Jun. 29, 2000

Related U.S. Application Data

(60) Provisional application No. 60/141,436, filed on Jun. 29, 1999.

(51) Int. Cl.$^7$ ............................................. A61K 31/405
(52) U.S. Cl. ........................................................ 514/415
(58) Field of Search ............................................ 514/415

(56) References Cited

U.S. PATENT DOCUMENTS

| | | |
|---|---|---|
| 3,610,795 A | 10/1971 | Antoine |
| 4,275,068 A | 6/1981 | Thiele et al. |
| 4,289,777 A | 9/1981 | Albrecht et al. |
| 4,767,712 A | 8/1988 | Motai et al. |
| 4,797,358 A | 1/1989 | Misaki et al. |
| 4,859,692 A | 8/1989 | Bernstein et al. |
| 4,921,786 A | 5/1990 | Takahashi et al. |
| 5,206,146 A | 4/1993 | Misaki et al. |
| 5,486,768 A | 1/1996 | Cipollina et al. |
| 5,521,197 A | 5/1996 | Audia |
| 5,583,149 A | 12/1996 | Cipollina et al. |
| 5,589,349 A | 12/1996 | Shinzaki et al. |
| 5,622,953 A | 4/1997 | Janssen et al. |
| 5,639,752 A | 6/1997 | Macor |
| 5,659,040 A | 8/1997 | Blatcher et al. |
| 5,708,008 A | 1/1998 | Audia et al. |
| 5,744,488 A | 4/1998 | Cross et al. |
| 5,786,473 A | 7/1998 | Blatcher et al. |
| 5,834,493 A | 11/1998 | Gil Quintero et al. |
| 5,849,764 A | 12/1998 | Goulet et al. |
| 5,932,743 A | 8/1999 | Collini et al. |
| 5,936,098 A | 8/1999 | Yasuda et al. |
| 5,962,474 A | 10/1999 | Audia et al. |
| 5,965,582 A | 10/1999 | Lebaut et al. |
| 5,977,154 A | 11/1999 | Bell et al. |
| 5,981,525 A | 11/1999 | Farina et al. |
| 5,981,550 A | 11/1999 | Goulet et al. |
| 5,981,776 A | 11/1999 | Diaz et al. |
| 5,990,150 A | 11/1999 | Matsui et al. |
| 5,998,438 A | 12/1999 | Slassi et al. |
| 6,022,880 A | 2/2000 | Effland et al. |
| 6,037,123 A | 3/2000 | Benton et al. |
| 6,046,136 A | 4/2000 | James et al. |
| 6,174,873 B1 | 1/2001 | Wrenn, Jr. |
| 6,187,541 B1 | 2/2001 | Benton et al. |
| 6,228,588 B1 | 5/2001 | Benton et al. |
| 6,339,073 B1 | 1/2002 | Pero |

FOREIGN PATENT DOCUMENTS

| | | |
|---|---|---|
| EP | 0 909 405 | 10/1993 |
| EP | 0 585 722 | 3/1994 |
| WO | WO 99/36422 | 7/1999 |
| WO | WO 00/10996 | 3/2000 |

OTHER PUBLICATIONS

Cristofoli et al., "the Synthesis of Tethered Heterocyclic Dimers as Inhibitors of NAD Synthetase", Gordon Research Conference on Heterocyclic Chemistry, New Port, Rhode Island, Jun. 28–Jul. 3, 1998 ("Title only").

Garcia et al., "Synthesis of Potential NAD Synthetase Inhibitors as Antibacterial Agents", Division of Medicinal Chemistry American Chemical Society National Meeting, Boston, Massachusetts, Aug. 23–27, 1998 ("Title only").

Schmitt et al., "The Synthesis of Tethered Heterocyclic Dimers as Inhibitors of NAD Synthetase", Division of Medicinal Chemistry, American Chemical Society National Meeting, Boston, Massachusetts, Aug. 23–27, 1998 ("Title only").

Garcia et al., "Combinatorial Synthesis of NAD Synthetase Inhibitors", Abstract 297, Divisional of Medicinal Chemistry, 218$^{th}$, National American Chemical Society Meeting, New Orleans, Louisiana, Aug. 22–26. 1999 ("Title only").

Poster #5 Abstract, Brouillette et al., "Synthesis of NAD Synthetase Inhibitors as Potential Antibacterial Agents", Abstract #298, Division of Medicinal Chemistry, 218$^{th}$ National American Chemical Society Meeting, New Orleans, LA, Aug. 22–26, 1999.

Poster #6 Abstract, Brouillette et al., "Synthesis of Inhibitors of Prokaryotic NAD Synthetase", Abstract #295, Division of Medicinal Chemistry, 218$^{th}$ National American Chemical Society Meeting, New Orleans, LA, Aug. 22–26, 1999.

Structure Search 1, May 10, 2000.
Structure Search 2, May 10, 2000.

Rizzi et al., "A novel deamido–NAD+–binding site revealed by the trapped NAD–adenylate intermediate in the NAD+ synthetase structure", Structure, vol. 6, No. 9, 1998, pp. 1129–1140.

Shridhar et al., "Antimicrobial Agents.: Synsthesisi & Antimicrobial Activity of New Aryloxyalkyu Esters of p–hydroxydenzoic acid", J. Par. Sc., vol. 65, No. 7, Jul. 1976, pp. 1074–1078.

Merck Index 1954, p. 1030, compound No. 6434: Nicotine.

Shridhar et al., "Antimicrobial Agents—Part III+:Synthesis and Antimicrobial Activity of Some New aryloxyalkyl Esters of 3–Allyl/methyl/chloro–4–Hydroxybenzoic Acids", J. Indian Chem. Soc., vol. LVI, Jan. 1979, pp. 74–76.

(List continued on next page.)

*Primary Examiner*—Kevin E. Weddington
(74) *Attorney, Agent, or Firm*—Womble Carlyle Sandridge & Rice, PLLC

(57) ABSTRACT

The present invention provides methods of treating or preventing fungal infections in a host comprising administering a treatment effective or treatment effective amount of a yeast NAD synthetase inhibitor compound. The invention further provides a method of killing yeast comprising administering a yeast NAD synthetase compound that selectively binds to catalytic sites in yeast whereby the yeast is killed.

87 Claims, No Drawings

OTHER PUBLICATIONS

Cristofoli et al., "The Synthesis of Tethered Heterocyclic Dimers as Inhibitors of NAD Synthetase", Poster presentation, Gordon Research Conference on Heterocyclic Compounds, 1998, Newport, RI (Abstract only).

J. Fostel and D. Montgomery, *Antimicro. Agents Chemother.*, 39, 586 (1995).

J. Fostel, D. Montgomery, and P. Lartey, *FEMS Microbiol. Lett.*, 138, 105 (1996).

N. H. Georgopapadakou, *Curr. Opin. Microbiol.*, 1, 547–557 (1998).

A. H. Groll and T.J. Walsh, *Curr. Opin. Infect. Dis.*, 10, 449 (1997).

C. A. Kauffman and P1 L. Carver, *Drugs*, 53, 539 (1997).

B. C. Monk and D. S. Perlin, *Crit. Rev. Microbiol.*, 20, 209 (1994). (b).

B. C. Monk, A. B. Mason, T.B. Kardos, and D. S. Perlin, *Acta Biochim. Pol.*, 42, 481 (1995).

K. Richardson, "Fluconazole, an Orally Active Antifungal Agent," in C. R. Ganellin and S. M. Roberts, *Medicinal Chemistry*, $2^{nd}$ ed., Academic Press, San Diego, 1993.

M. Rizzi, C. Nessi, A. Mattevi, A. Coda, M. Bolognesi, and A. Galizzi, *The EMBO Journal*, 15, 5125–5134 (1996).

E. G. Weinberg, "Antifungal Agents," in W.O. Foye, T. L. Lemke, and D. A. Williams, *Principles of Medicinal Chemistry*, $4^{th}$ edition, Williams and Jenkins, Media, PA, 1995, pp. 803–811.

C. K. Yu and L. S. Dietrich, *J. Biol. Chem.*, 247, 4794–4802 (1972).

METHODS OF TREATING FUNGAL INFECTIONS WITH INHIBITORS OF NAD SYNTHETASE ENZYME

CROSS REFERENCE TO RELATED APPLICATIONS

This application is related to copending provisional application Ser. No. 60/141,43, filed Jun. 29, 1999, which is incorporated by reference, and claims the benefit of its earlier filing date under 35 USC Section 119(e).

STATEMENT AS TO FEDERALLY SPONSORED RESEARCH

This invention was made, at least in part, with a government grant from DARPA (Grant No. MDA 972-96-K). The U.S. government may have certain rights in this invention.

FIELD OF THE INVENTION

The present invention relates to methods of treating fungal infections. More particularly, the present invention relates to methods of treating yeast infections with compounds that selectively target the NAD synthetase enzyme of yeast, with little or no attendant targeting of the NAD synthetase enzyme of the host.

BACKGROUND OF THE INVENTION

The incidence of serious fungal infections, either systemic or topical, continues to increase for plants, animals, and humans. Fungi are plant-like eukaryotes that grow in colonies of single cells, called yeasts, or in filamentous mutlicellular aggregates, called molds. While many fungi are common in the environment and not harmful to plants or mammals, some are parasites of terrestrial plants and others can produce disease in humans and animals. When present in humans, mycotic (fungal) diseases can include contagious skin and hair infections, noncontagious systemic infections, and noncontagious foodborne toxemias. The incidence of such infections is not insignificant; in the U.S. approximately 10% of the population suffers from contagious skin and hair infections. While few healthy persons develop life-threatening systemic fungal infections, immunocompromised individuals, such as found in pregnancy, congenital thymic defects, or acquired immune deficiency syndrome (AIDS), can become seriously ill. This is further illustrated by the fact that fungal infections have become a major cause of death in organ transplant recipients and cancer patients.[1]

Numerous antifungal agents have been developed for topical use against nonsystemic fungal infections. However, the treatment of systemic fungal infections, particularly in immunocrompromised hosts, continues to be a major objective in infectious disease chemotherapy. The organisms most commonly implicated in systemic infections include Candida spp., *Cryptococcus neoformans*, and Aspergillus spp., although there are a number of emerging pathogens. The major classes of systemic drugs in use currently are the polyenes (e.g., amphotericin B) and the azoles (e.g., fluconazole). While somewhat effective in otherwise healthy patients, these agents are inadequate in severely immunocompromised individuals. Furthermore, drug resistance has become a serious problem, rendering these antifungal agents ineffective in some individuals.[2,3]

One reason for the limited number of systemic antifungal agents relates to the fact that, unlike bacteria, which are prokaryotes, yeast and molds are eukaryotes. Thus the biochemical make-up of yeast and molds more closely resembles eukaryotic human and animal cells. In general, this has made it difficult to develop antifungal drugs which selectively target in yeast an essential enzyme or biochemical pathway that has a close analog in humans and animals.

The ability to selectively inhibit the yeast form of a biochemical target with minimal effect on the mammalian form would provide a number of new approaches to the development of systemic antifungal drugs. In a few cases, this type of approach has already been proven to provide clinically useful systemic antifungal agents. For example, the mechanism of action for fluconazole, a widely used systemic antifungal drug, involves inhibition of a fungal C-14 demethylase, a cytochrome P450 enzyme that is essential for the production of the principal fungal sterol ergosterol. Ergosterol is very similar to the mammalian steroid cholesterol, and there is a closely related mammalian C-14 demethylase enzyme for which fluconazole is a much poorer inhibitor. This selectivity for inhibition of the fungal form of the enzyme over the mammalian form has resulted in the clinical utility of fluconazole.[4] In a further example, preclinical studies on new antifungal agents that select for the yeast form over the mammalian form of a biochemical target include development of inhibitors for the plasma membrane ATPase[5] and for topoisomerase I.[6]

The inventors herein previously were part of a group that developed a number of antibacterial and antimicrobial agents that were targeted to NAD synthetase, an essential enzyme found in nearly all prokaryotic and eukaryotic cells. This enzyme is essential for the biosynthesis of nicotinamide adenine dinucleotide (NAD$^+$), an essential cofactor in numerous enzymatic reactions. NAD synthetase catalyzes the last step in both the de novo and salvage pathways for NAD$^+$ biosynthesis, which involves the transfer of ammonia to the carboxylate of nicotinic acid adenine dinucleotide (NaAD) in the presence of ATP and Mg$^{+2}$. The overall reaction is illustrated in Scheme 1.

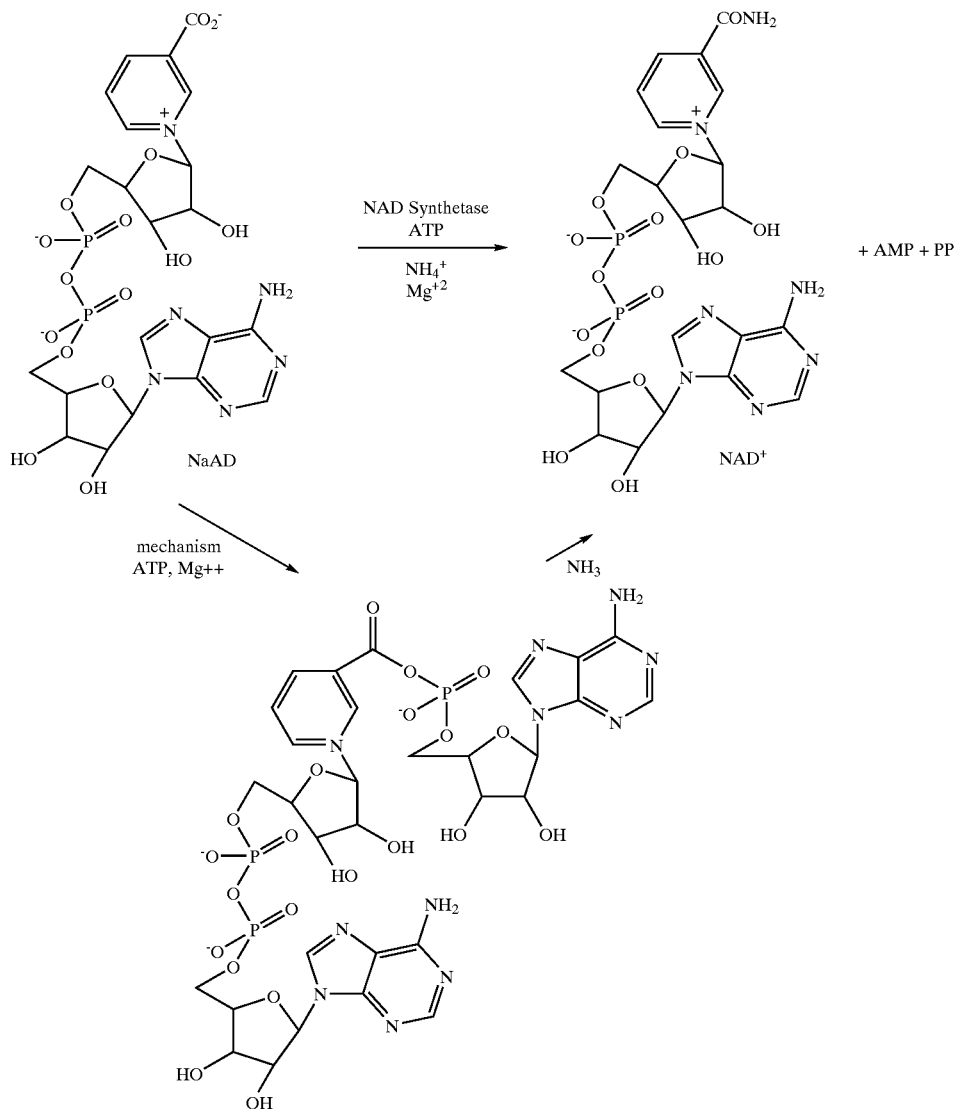

Scheme 1

Prokaryotic NAD synthetase is an ammonia-dependent amidotransferase that belongs to a family of "N-type" ATP pyrophosphatases; this family also includes asparagine synthetase and argininosuccinate synthetase.[7] Unlike eukaryotic NAD synthetase found in yeast and mammals that can use glutamine as a source of nitrogen, the prokaryotic NAD synthetase of bacteria requires ammonia as the only nitrogen source. Furthermore, *B. subtilis* NAD synthetase, which was previously crystallized and used for drug design by the inventors, is a dimer with molecular weight around 65,000, while the yeast enzyme is multimeric and has at least 10 times larger molecular weight.[8] These differences between eukaryotic and prokaryotic forms of NAD synthetase enzyme suggested that drugs specific for the prokaryotic enzyme could be designed, and the inventors subsequently developed inhibitors of this enzyme that are effective antibacterial and antimicrobial agents.[9] Given these marked differences between prokaryotic and eukaryotic NAD synthetase, the inventors fully expected that the compounds would be selective for the prokaryotic NAD synthetase and would show little to no effect on eukaryotic NAD synthetase.

SUMMARY OF THE INVENTION

The present invention is based in part on the surprising discovery that NAD synthetase inhibitors are highly effective in inhibiting the growth of yeast, yet exhibited only moderate toxicity in animals. Thus, the present invention includes the use of NAD synthetase inhibitors as new antifungal agents for preventing or controlling parasitic yeast and mold infections in plants, and for the prophylactic or therapeutic treatment, topically and systemically, of fungal infections in humans and animals.

In a major aspect, the present invention provides a method of treating or preventing an antifungal infection in a host comprising administering to a host a treatment effective or treatment preventive amount of a yeast NAD synthetase enzyme inhibitor compound.

In a further aspect, the method of killing yeast with an amount of yeast NAD synthetase enzyme inhibitor to reduce or eliminate the production of NAD whereby the yeast is killed.

In yet another aspect, the invention provides a method of decreasing yeast growth, comprising contacting the yeast with an amount of a yeast NAD synthetase enzyme inhibitor effective to reduce or eliminate the production of NAD whereby yeast growth is decreased.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included herein.

Before the present methods, compounds, compositions and apparatuses are disclosed and described it is to be understood that this invention is not limited to the specific synthetic methods described herein. It is to be further understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

Throughout this application, where a chemical diagram has a straight line emanating from a chemical structure, such a line represents a CH$_3$ group. For example, in the following diagram:

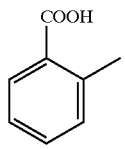

o-methylbenzoic acid is represented.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkylene" as used herein refers to a dysfunctional saturated branched or unbranched hydrocarbon chain containing from 1 to 24 carbon atoms, and includes, for example, methylene (—CH2-), ethylene (—CH2-CH2-), propylene (—CH2-CH2-CH2-), 2-methylpropylene [—CH2-CH(CH3)-CH2-], hexylene [—(CH2)6-] and the like. The term "cycloalkylene" as used herein refers to a cyclic alkylene group, typically a 5- or 6-membered ring.

The term "alkene" as used herein intends a mono-unsaturated or di-unsaturated hydrocarbon group of 2 to 24 carbon atoms. Asymmetric structures such as (AB)C=C(CD) are intended to include both the E and Z isomers. This may be presumed in structural formulae herein wherein an asymmetric alkene is present.

The term "alkynyl" as used herein refers to a branched or unbranched unsaturated hydrocarbon group of 1 to 24 carbon atoms wherein the group has at least one triple bond.

The term "cyclic" as used herein intends a structure that is characterized by one or more closed rings. As further used herein, the cyclic compounds discussed herein may be saturated or unsaturated and may be heterocyclic. By heterocyclic, it is meant a closed-ring structure, preferably of 5 or 6 members, in which one or more atoms in the ring is an element other than carbon, for example, sulfur, nitrogen, etc.

The term "bicyclic" as used herein intends a structure with two closed rings. As further used herein, the two rings in a bicyclic structure can be the same or different. Either of the rings in a bicyclic structure may be heterocyclic.

By the term "effective amount" of a compound as provided herein is meant a sufficient amount of the compound to provide the desired treatment or preventive effect. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation. It is preferred that the effective amount be essentially non-toxic to the subject, but it is contemplated that some toxicity will be acceptable in some circumstances where higher dosages are required.

By "pharmaceutically acceptable carrier" is meant a material that is not biologically or otherwise undesirable, i.e., the material may be administered to an individual along with the compounds of the invention without causing any undesirable biological effects or interacting in a deleterious manner with any of the other components of the pharmaceutical composition in which it is contained.

As used herein, "NAD synthetase enzyme" is defined as the enzyme that catalyzes the final reaction in the biosynthesis of NAD, namely, the transformation of NaAD into NAD. As used herein, the term "catalytic sites" are defined as those portions of the NAD synthetase enzyme that bind to substrates, and cofactors, including nicotinic acid adenine dinucleotide (NaAD), NAD, adenosine triphosphate (ATP), adenosine monophosphate (AMP), pyrophosphate, magnesium and ammonia in yeast. The term "receptor site" or "receptor subsite" relates to those portions of the yeast NAD synthetase enzyme in which the yeast NAD synthetase enzyme inhibitors disclosed herein are believed to bind. For the purposes of this disclosure, the terms "catalytic site," "receptor site" and "receptor subsite" may be used interchangeably.

In one embodiment, the invention provides administering an antifungal agent to a mammal in need of such treatment or prevention. In one embodiment, the fungal agent that causes the infection is yeast. In separate embodiments of the methods of administering, the antifungal agent comprises one or more compounds in FIG. 1 below. In further separate preferred embodiments of the methods of administering, the antifungal agent comprises one or more of the compounds set forth in FIG. 2 below. In still further separate embodiments, the compounds administered comprise one or more of the compounds of Structure 2, Structure 4, Structure 6, Structure 7, Structure 8, Structure 10, or Structure 12. In yet further separate embodiments of the methods of administering, the antifungal agent comprises one or more of the compounds denoted 1 to 1106 below.

Further provided by the invention herein is preferably a method of killing yeast with an amount of yeast NAD synthetase enzyme inhibitor compound to reduce or eliminate the production of NAD whereby the yeast is killed. A method of decreasing yeast growth, comprising contacting the yeast with an amount of yeast NAD synthetase enzyme inhibitor effective to reduce or eliminate the production of NAD whereby yeast growth is decreased is also provided. With respect to the method of killing yeast, as well as in the method of decreasing yeast growth, in separate embodiments of the methods the compound comprises one or more compounds of FIG. 1 below. In further separate embodiments, the compound comprises one or more compounds of FIG. 2 below. In a further embodiment, the compound administered is a compound of Structure 2, Structure 4, Structure 6, or Structure 7. In still further embodiments, the compounds administered comprise one or more of the compounds of Structure 8, Structure 10, or Structure 12. In yet further separate embodiments, the compounds administered comprise one or more compounds denoted 1–1106 below.

FIGURE 1:
LEAD I COMPOUNDS

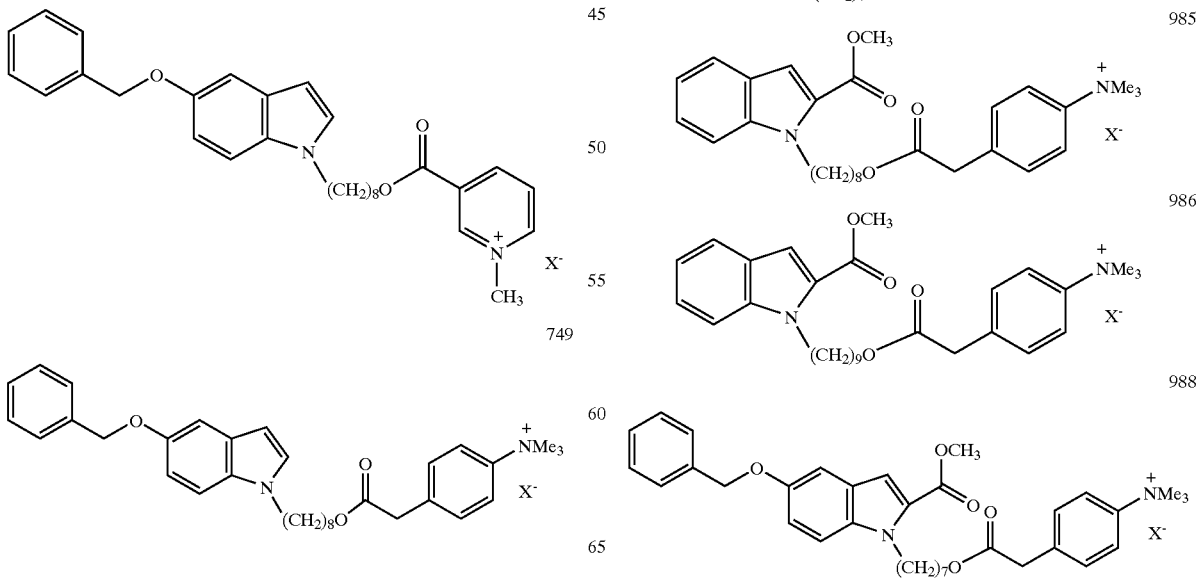

-continued
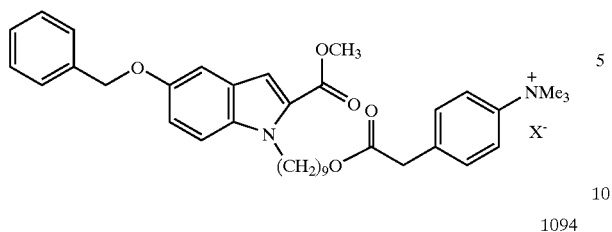
970
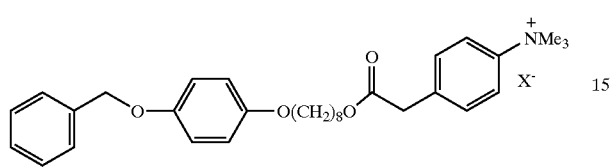
1094
In yet a further embodiment, the compound comprises one or more compounds of FIG. 2 below ("Lead II Compounds").
FIG. 2:
LEAD II COMPOUNDS
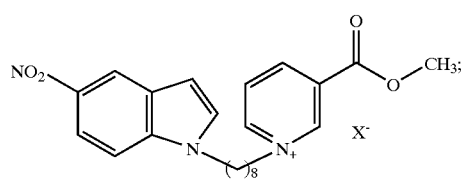
13
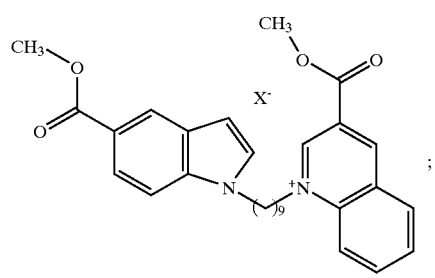
174
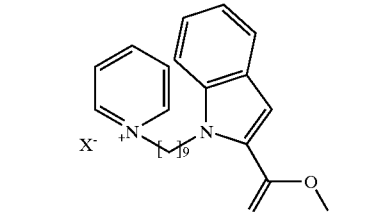
182
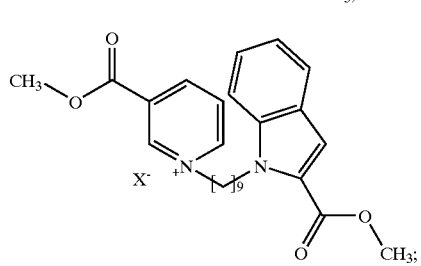
190
-continued
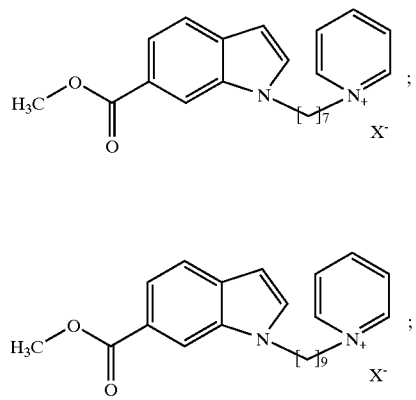
213
214
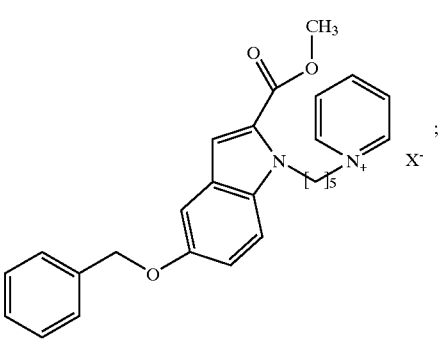
228
229
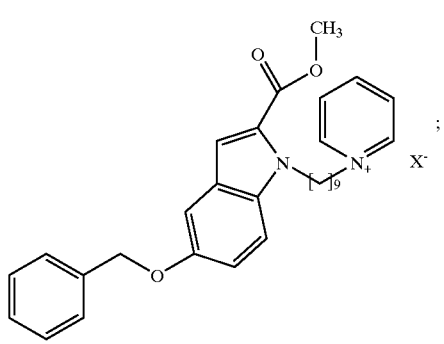
230

270
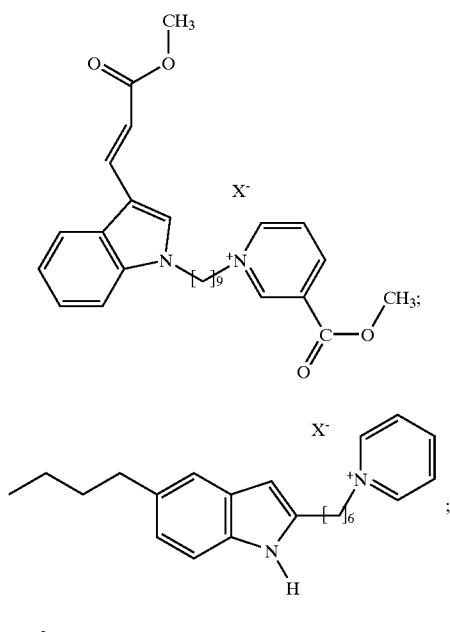
315
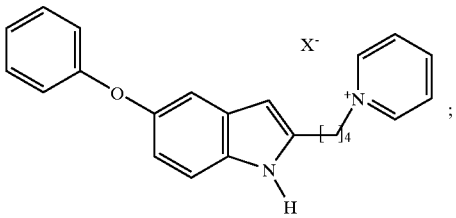
349
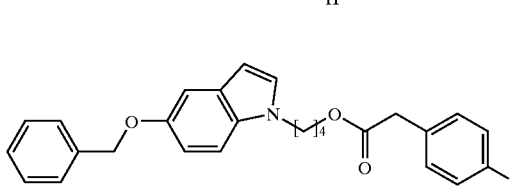
745
746
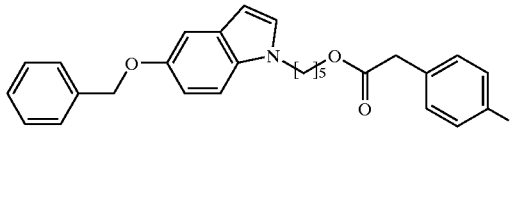
747
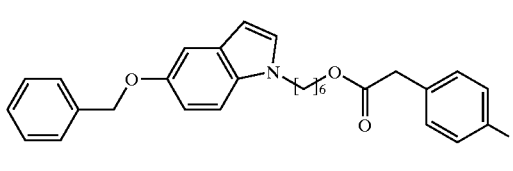
748
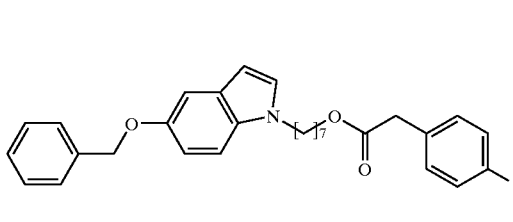
749
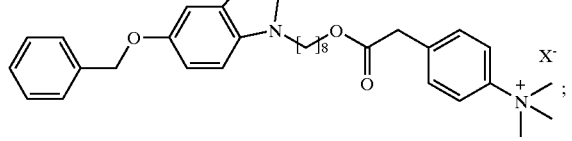
765
766
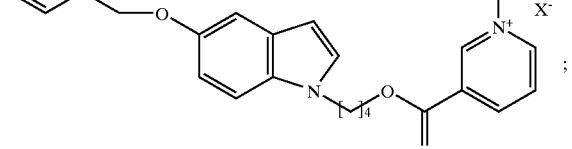
767
768
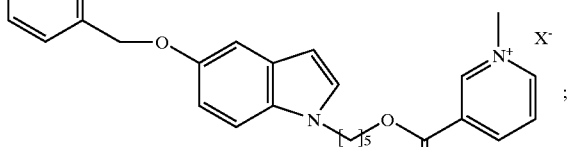
769

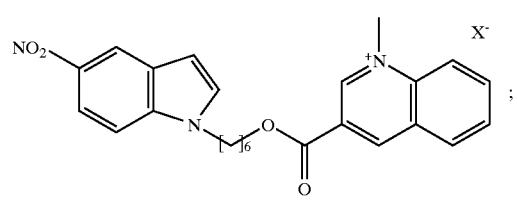
832
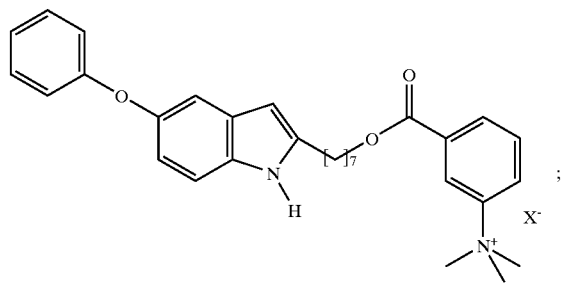
872
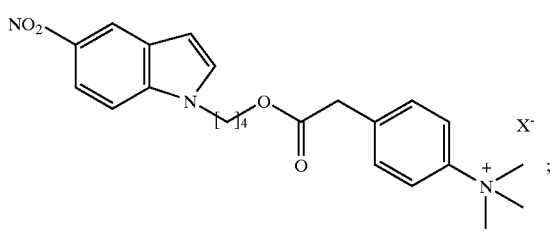
848
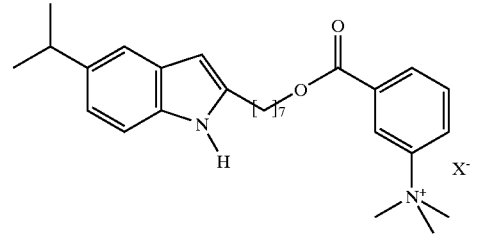
875
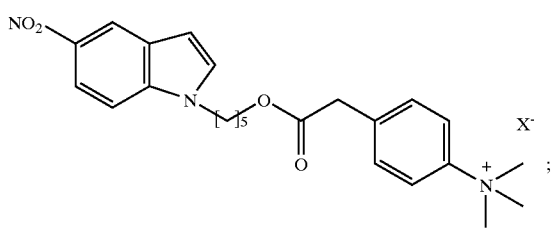
849
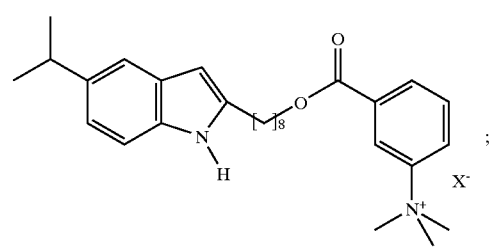
876
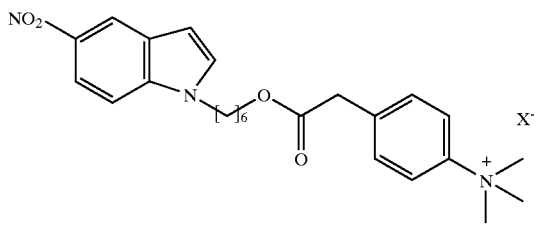
850
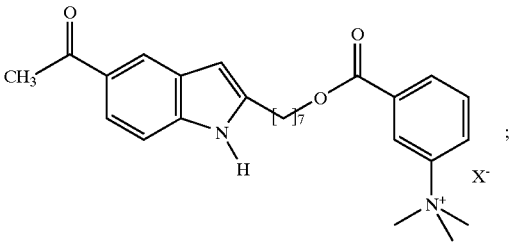
878
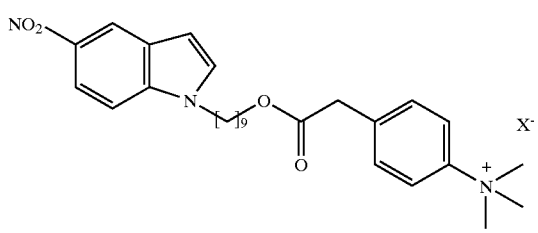
853
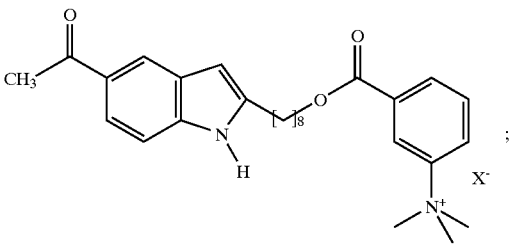
879
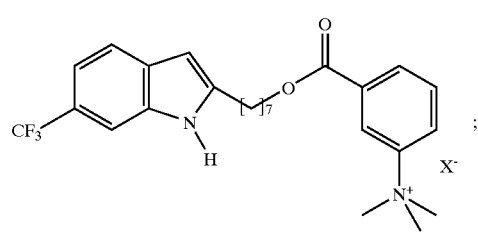
869
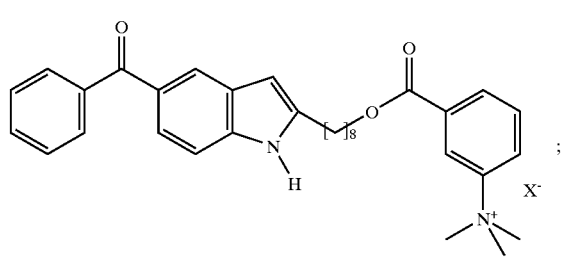
882

884
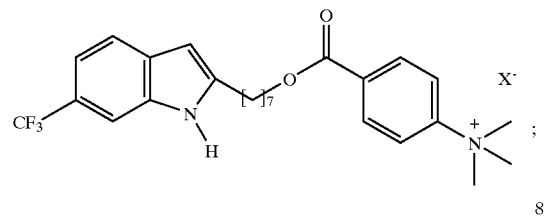
886
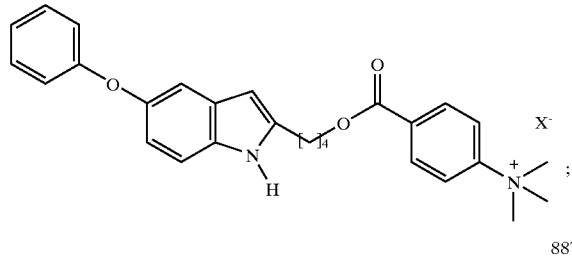
887
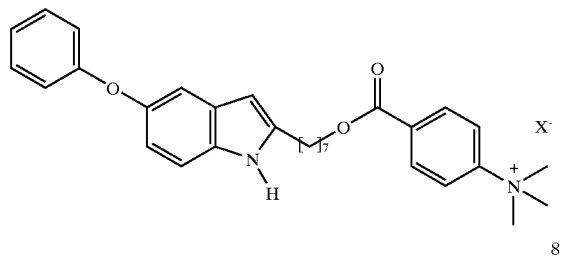
889
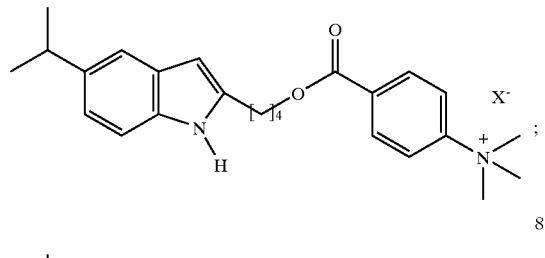
891
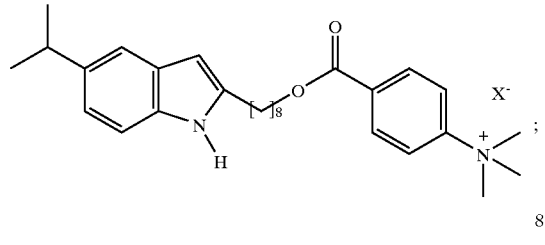
894
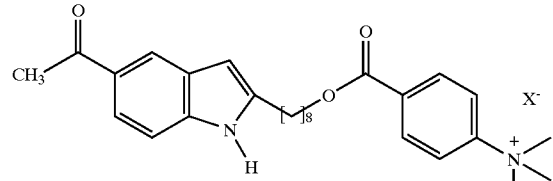
906
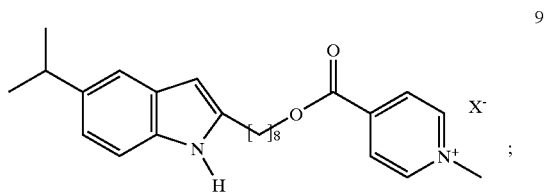
909
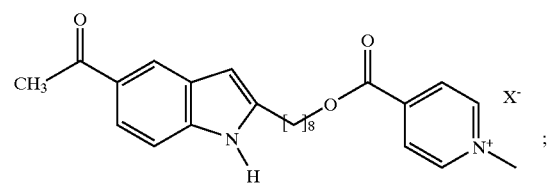
917
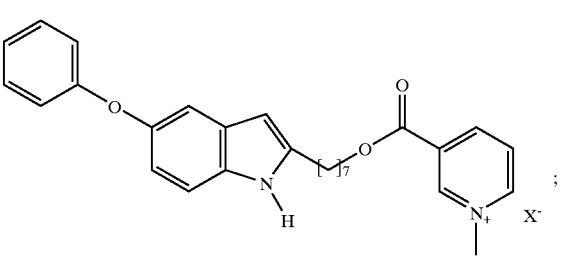
921
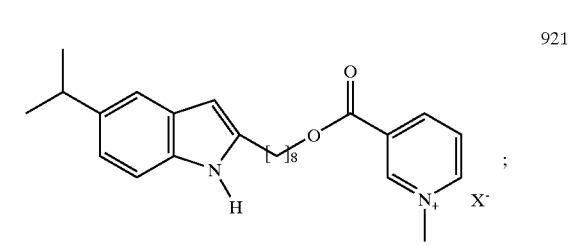
924
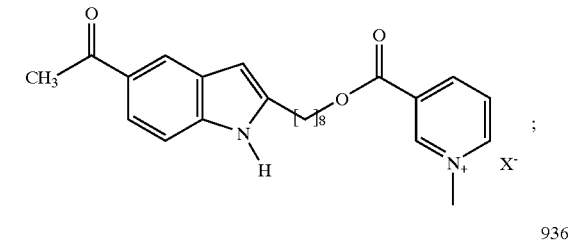
936
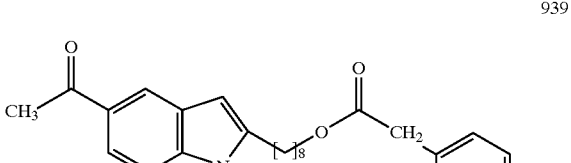
939
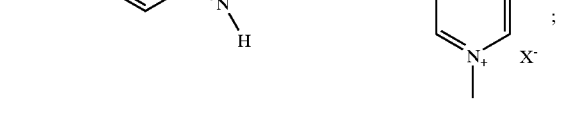

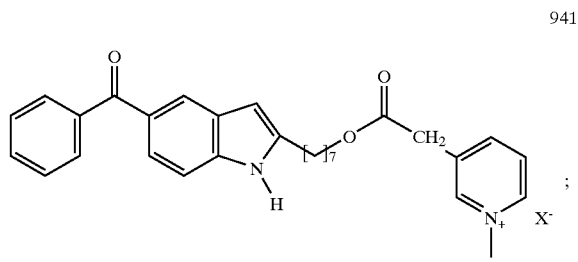
941
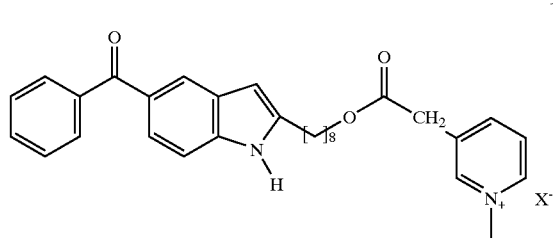
942
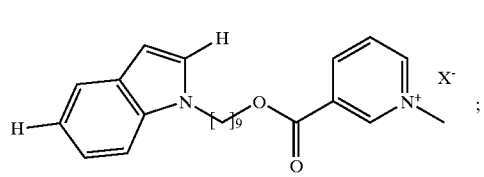
970
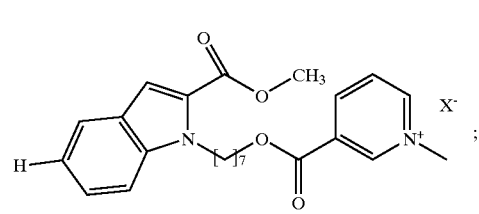
972
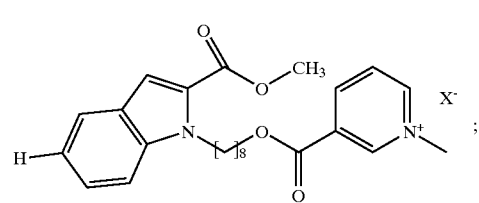
973
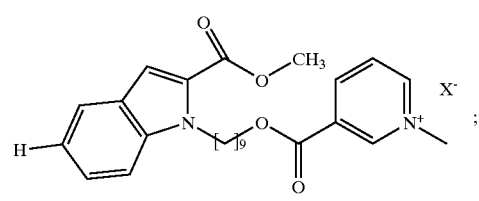
974
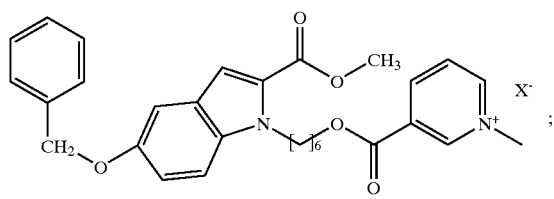
975
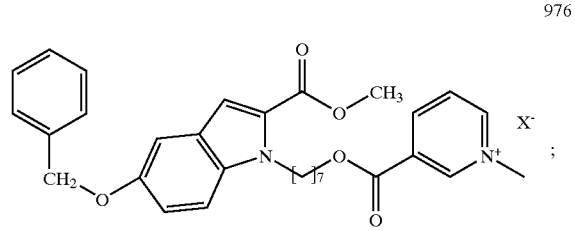
976
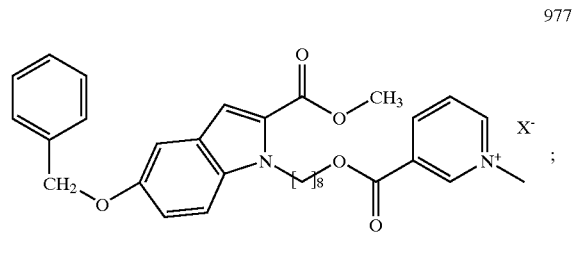
977
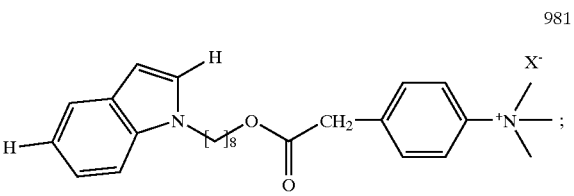
981
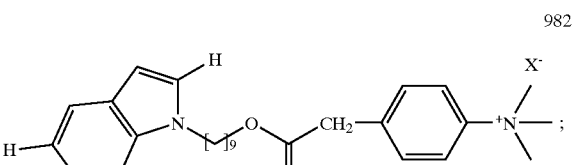
982
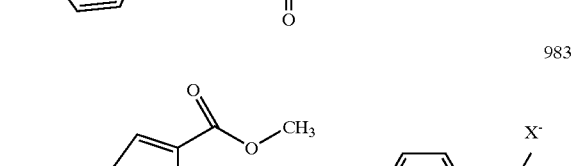
983
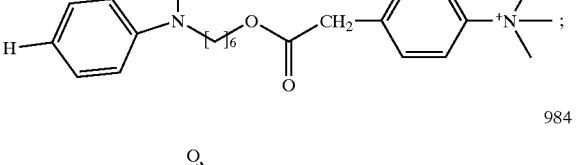
984
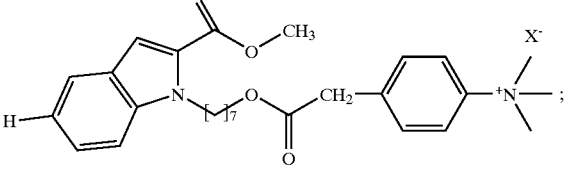
985
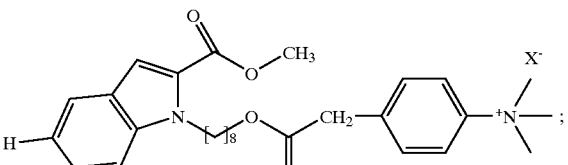
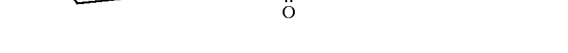

-continued
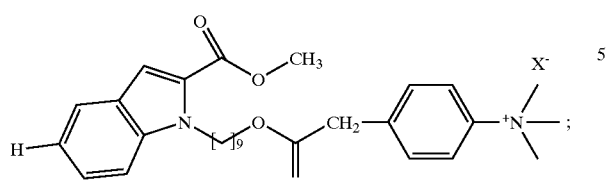
986
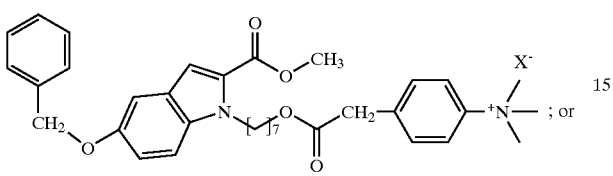
988
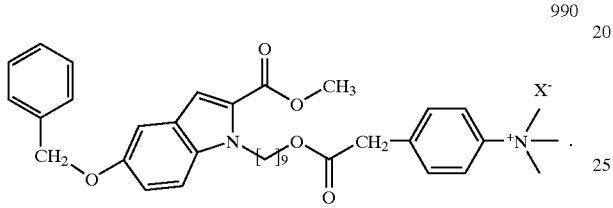
990
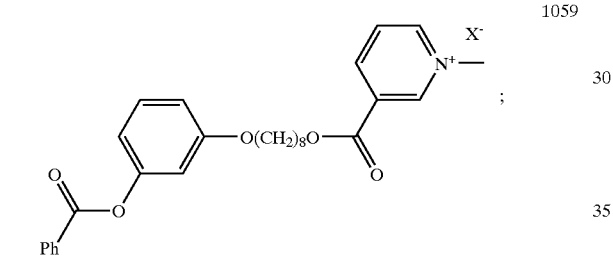
1059
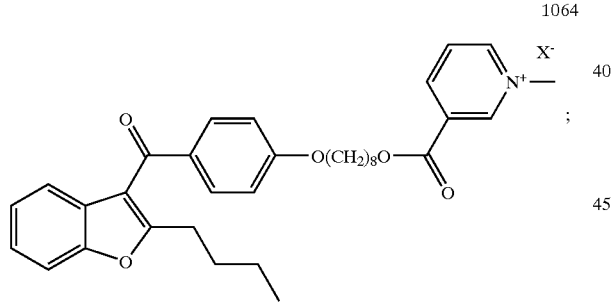
1064
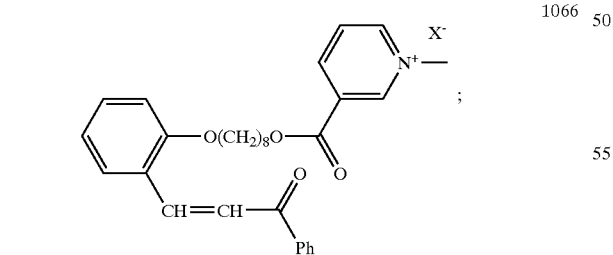
1066
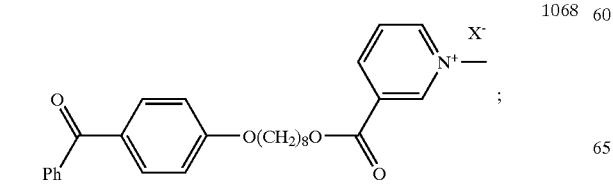
1068
-continued
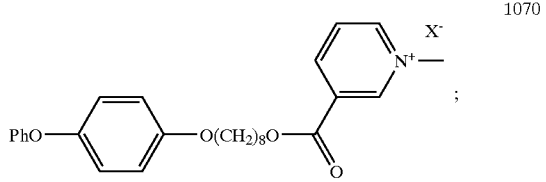
1070
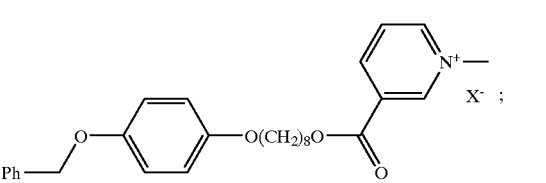
1072
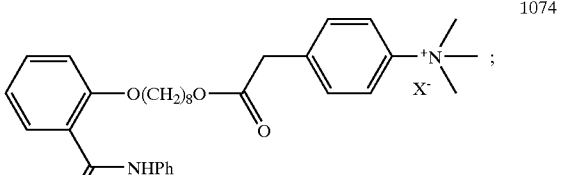
1074
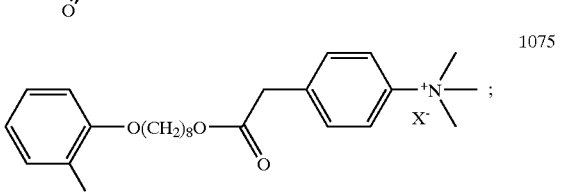
1075
1079
1080
1082
1084

-continued
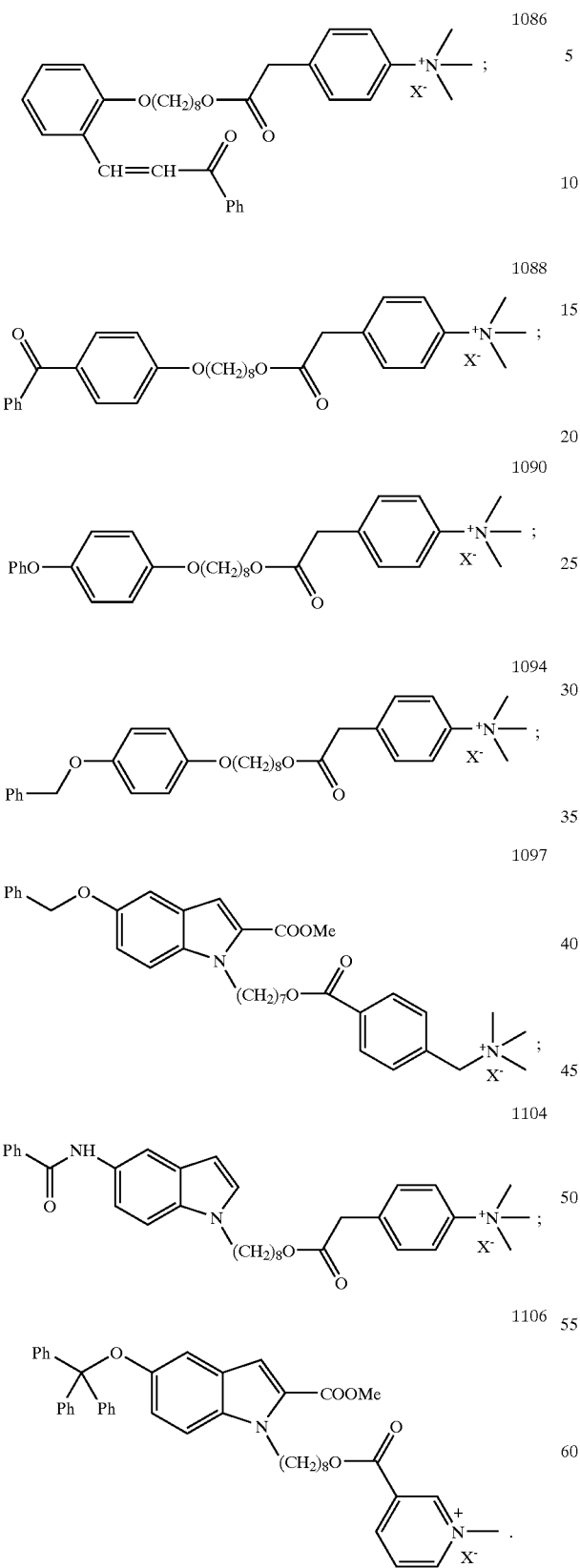
-continued
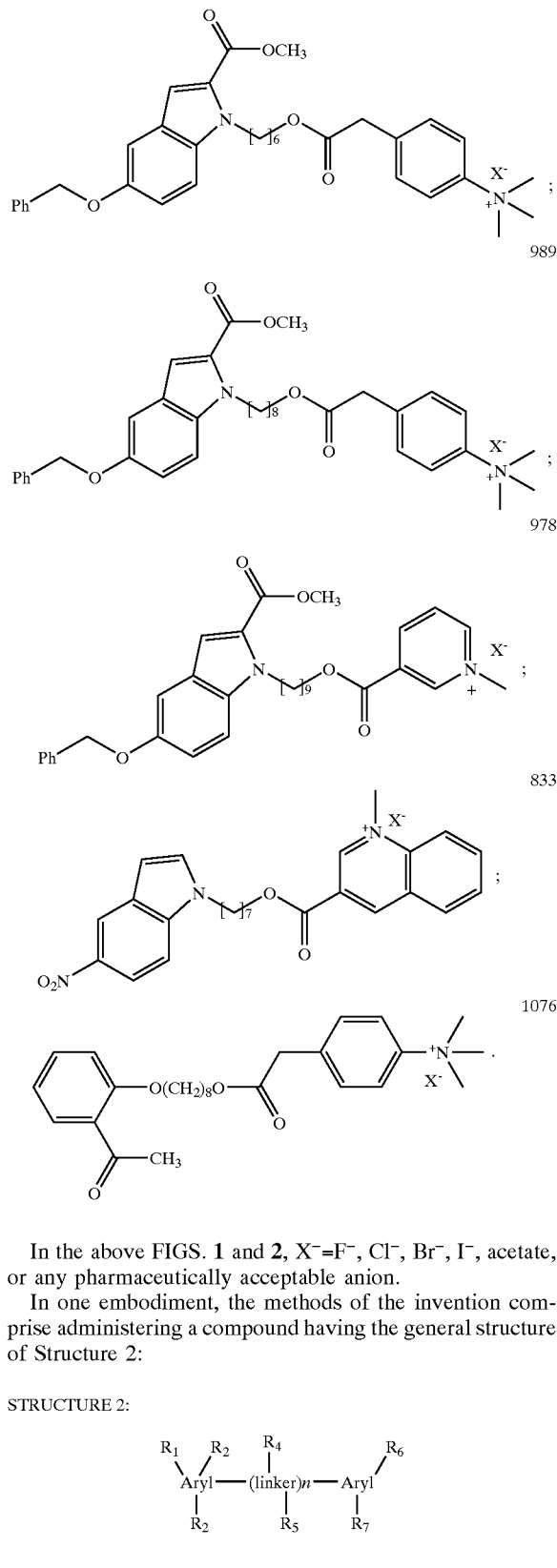
In the above FIGS. 1 and 2, $X^- = F^-$, $Cl^-$, $Br^-$, $I^-$, acetate, or any pharmaceutically acceptable anion.
In one embodiment, the methods of the invention comprise administering a compound having the general structure of Structure 2:
STRUCTURE 2:
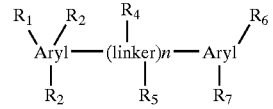

wherein:

n is an integer of from 1 to 12, $R_1$–$R_7$ each, independently, is an H, an unsubstituted or a substituted cyclic or aliphatic group, a branched or an unbranched group, and wherein the linker is a cyclic or aliphatic, branched or an unbranched alkyl, alkenyl, or an alkynyl group and wherein the linker may also contain heteroatoms. By heteroatoms, it is meant that one or more atoms is an element other than carbon.

$R_1$–$R_7$ may also be one of the following groups: an H, alkyl, alkenyl, alknyl, or an aryl. $R_1$–$R_7$, may further be a hydroxyl, ketone, nitro, amino, amidino, guanidino, carboxylate, amide, sulfonate, or halogen or the common derivatives of these groups. Note that n may also be an integer of from 3 to 10, more preferably 5 to 9 and, still more preferably 6 to 9. The tethered active molecule, e.g., in this example denoted "aryl," moieties may be the same or different.

In a further embodiment, the invention comprises administering a compound of Structure 4:

STRUCTURE 4:

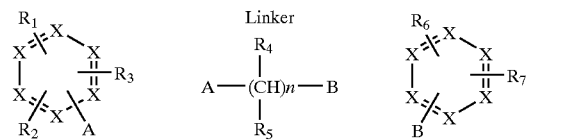

wherein:

X is a C, N, O or S within a monocyclic or bicyclic moiety, A and B represent the respective sites of attachment for the linker, n is an integer of from 1 to 12, $R_1$–$R_7$ each, independently, is an H, an unsubstituted or a substituted cyclic group, or an aliphatic group, or a branched or an unbranched group, and the linker is a saturated or unsaturated cyclic group or an aliphatic branched or unbranched alkyl, alkenyl or alkynyl group, and wherein the linker may also contain heteroatoms.

$R_1$–$R_7$ may also be one of the following groups: an H, alkyl, alkenyl, alkynyl, or an aryl group. $R_1$–$R_7$ may also be a hydroxyl, ketone, nitro, amino, amidino, guanidino, carboxylate, amide, sulfonate, or halogen or the common derivatives of these groups. One of skill in the art would know what moieties are considered to constitute derivatives of these groups. N may also be an integer of from 3 to 10, more preferably 5 to 9 and, still more preferably 6 to 9.

In a further embodiment, the methods of the invention comprise administering a compound of Structure 6:

STRUCTURE 6:

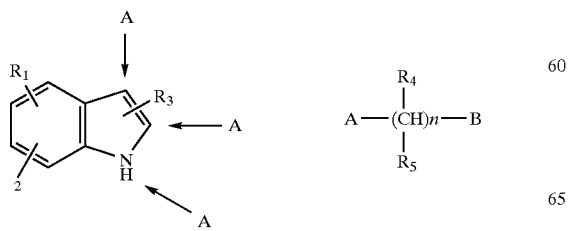

-continued

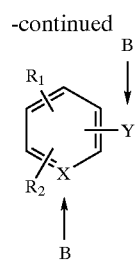

wherein:

X is C, N, O or S, Y is C, N, O, S, carboxy, ester, amide, or ketone, A and B represent he respective sites of attachment for a linker, n is an integer of from 1 to 12, and $R_1$–$R_7$ each, independently, is an H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain heteroatoms.

$R_1$–$R_7$ may also be one of the following groups: an H, alkyl, alkenyl, alknyl, or an aryl. $R_1$–$R_7$, may further be a hydroxyl, ketone, nitro, amino, amidino, guanidino, carboxylate, amide, sulfonate, or halogen or the common derivatives of these groups. Note that n may also be an integer of from 3 to 10, more preferably 5 to 9 and, still more preferably 6 to 9. The tethered active molecule, e.g., in this example denoted "aryl," moieties may be the same or different.

In a further embodiment, the methods of the invention comprise administering a compound of Structure 7:

STRUCTURE 7

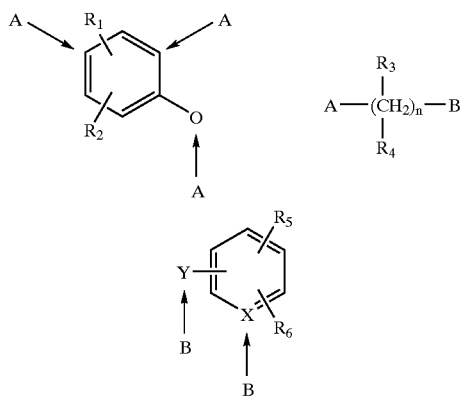

wherein:

X is C, N, O or S, Y is C, N, O, S, carboxy, ester, amide, or ketone, A and B represent the respective sites of attachment for a linker, n is an integer of from 1 to 12, and $R_1$–$R_6$ each, independently, is an H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain heteroatoms.

$R_1$–$R_6$ may also be one of the following groups: an H, alkyl, alkenyl, or alkynyl, or an aryl group. $R_1$–$R_6$ may also be an H, hydroxyl, ketone, nitro, amino, amidino, guanidino, carboxylate, amide, sulfonate, or halogen and the common derivatives of these groups. One of skill in the art would know what moieties are considered to constitute derivatives of these groups. N may also be an integer of from 3 to 10, more preferably 5 to 9 and, still more preferably 6 to 9.

In a further embodiment, the methods of the invention comprise administering a compound of Structure 8:

STRUCTURE 8:

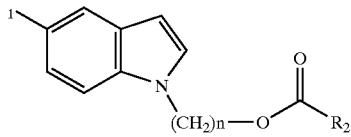

wherein:

n is an integer of from 1 to 12, $R_1$ is an H, methoxy, benzyloxy, or nitro and $R_2$ is 3–pyridyl, N-methyl-3-pyridyl, 3-quinolinyl, N-methyl-3-quinolinyl, 3-(dimethylamino)phenyl, 3-(trimethylammonio) phenyl, 4-(dimethylamino)phenyl, 4-(trimethylammonio)phenyl, 4-(dimethylamino) phenylmethyl, or 4-(trimethylammonio)phenylmethyl. N may also be an integer of from 3 to 10, more preferably 5 to 9 and, still more preferably 6 to 9.

In a further embodiment, the methods of the invention comprise administering a compound of Structure 10:

STRUCTURE 10:

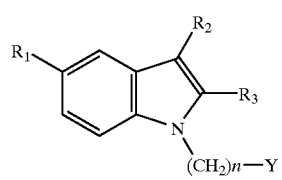

wherein:

n is an integer of from 1 to 12, $R_1$ is an H, $CO_2H$, —$OCH3$, or —$OCH_2Ph$, $R_2$ is H, $CO_2H$, or $CH=CHCO_2H$, $R_3$ is H or $CO_2H$, and Y is N-linked pyridine-3-carboxylic acid, N-linked pyridine, N-linked quinoline, or N-linked isoquinoline. N may also be an integer of from 3 to 10, more preferably 5 to 9 and, still more preferably 6 to 9.

In a further embodiment, the methods of the invention comprise administering a compound of Structure 12:

STRUCTURE 12:

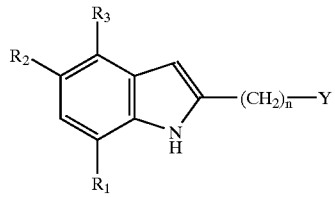

wherein:

n is an integer of from 1 to 12, $R_1$ is H, F, or $NO_2$, $R_2$ is H, $CH_3$, $CF_3$, $NO_2$, phenyl, n-butyl, isopropyl, F, phenyloxy, triphenylmethyl, methoxycarbonyl, methoxy, carboxy, cetyl, or benzoyl, $R_3$ is H or $CF_3$ and Y is N-linked pyridine-3-carboxylic acid, N-linked pyridine, N-linked quinoline, or N-linked isoquinoline. N may also be an integer of from 3 to 10, more preferably 5 to 9 and, still more preferably 6 to 9.

In a further embodiment, the methods of the invention comprise administering a compound of Structure 14:

STRUCTURE 14:

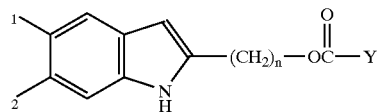

wherein:

n is an integer of from 1 to 12, $R_1$ is H, phenyloxy, isopropyl, acetyl, or benzoyl, $R_2$ is H or $CF_3$, and Y is 3-(dimethylamino)phenyl, 3-(trimelthylammonio) phenyl, 4-(dimethylamino)phenyl, 4-(trimethylammonio)phenyl, 2-(phenyl)phenyl, diphenylmethyl, 3-pyridyl, 4-pyridyl, or pyridine-3-methyl. N may also be an integer of from 3 to 10, more preferably 5 to 9 and, still more preferably 6 to 9.

In further embodiments of the invention herein, the invention comprises administering compounds of the structures denoted in Tables 102–128 as Compounds 1–274 were synthesized utilizing the methods disclosed previously in co-pending patent application PCT/US99/00810.

For Compounds 1–274, structures denoted in FIG. 6 as Fragments I–X each represent an active molecule, as defined previously herein, which can be included in the compounds of the present invention as further described in the respective Tables. In Fragments I–X of FIG. 6, the point of attachment for the linker compound is at the nitrogen.

In the chemical structures that follow, and as intended for the compounds of this invention, the symbol $T^-$ or $X^-$ designates generally the presence of an anion. As contemplated by the present invention, the type of anion in the compounds of this invention is not critical. The compounds of this invention may be comprised of any such moieties known generally to one of skill in the art or that follow from the synthesis methods disclosed in co-pending patent application PCT/US99/00810.

In separate embodiments of the invention herein, the methods of the invention comprise administering a compound corresponding to Structure 100:

Structure 100

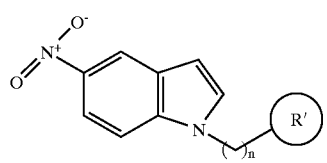

wherein R' is as defined below in FIG. 6:

FIGURE 6

I

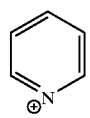

II 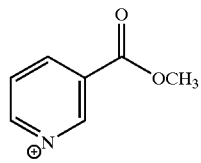

III 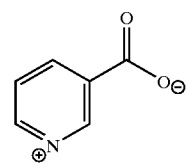

IV 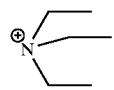

V 

VI 

VII 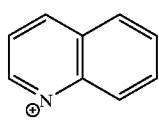

VIII 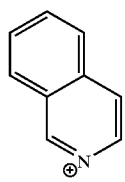

IX 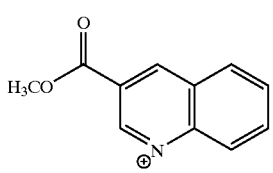

X 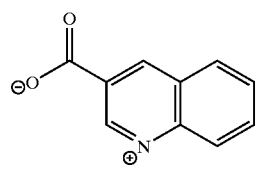

and n is an integer of from 1 to 12. N may also be from 3 to 10, more preferably 5 to 9 and, still more preferably 6 to 9.

In further separate embodiments of the invention herein, the methods of the invention comprise administering a compound corresponding to the structures set out in Structure 100 and as further defined in Table 100. For those compounds that correspond to Structure 100, n may also be an integer of from 1 to 12, from 3 to 10, from 5 to 9 and, still further, from 6 to 9.

STRUCTURE 100:

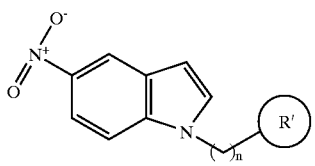

TABLE 100

SUBSTITUENT GROUPS FOR COMPOUNDS 1–24

| R' | n = 3 | 4 | 5 | 6 | 7 | 8 | 9 |
|---|---|---|---|---|---|---|---|
| I | 1 | 2 | 3 | 4 | 5 | 6 | 7 |
| II | 8 | 9 | 10 | 11 | 12 | 13 | 14 |
| III | 15 | 16 | 17 | 18 | 19 | 20 | 21 |
| IV | | | | | 22 | | |
| V | | | | | 23 | | |
| VI | | | | | 24 | | |

In the above Table, R' corresponds to a Fragment as previously defined in FIG. 6 and n indicates the number of linker groups separating the two tethered active molecule groups in the compound.

As set out below in relation to Compounds 25–274, Fragments A–G are set out in FIG. 8. The group denoted R in A–G of FIG. 8 can be a benzyl group, a methyl group or a hydrogen. The point of attachment of the linker group to Fragments A–G is at the nitrogen group.

In one embodiment, the methods of the invention comprise administering a compound corresponding to compounds of Structure 101. For those compounds that correspond to Structure 101, n is an integer of from 1 to 12, more preferably from 3 to 10, more preferably from 5 to 9 and, still more preferably from 6 to 9. The point of attachment of the linker group for both $R_1$ and R' is at the respective nitrogen groups of each illustrated fragment.

Structure 101

wherein R' is:

I 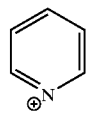

II 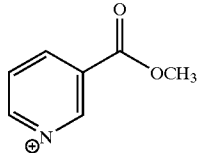

-continued
III
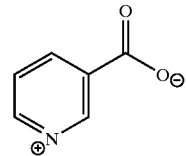
IV
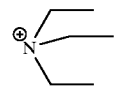
V
VI
VII
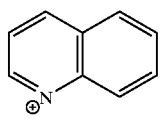
VIII
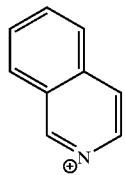
IX
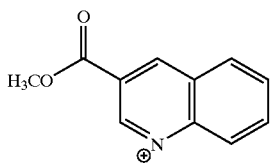
X
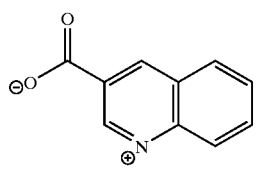
wherein R1 is:
A
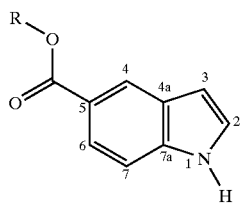
B
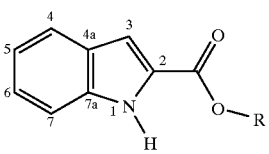
-continued
C
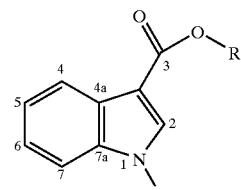
D
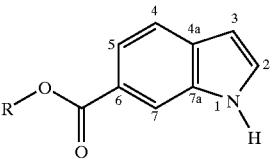
E
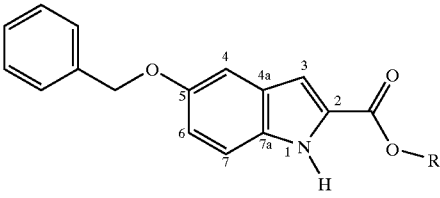
F
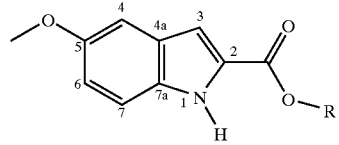
G
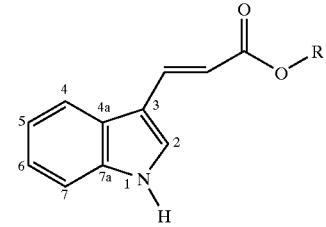
wherein the R group in Fragments A–G is a benzyl group, a methyl group or a hydrogen.
In one embodiment of the invention herein, the compounds may include the Fragments illustrated below in FIG. 8.
A
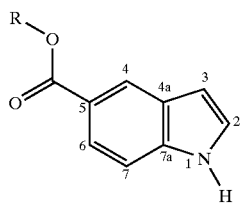
B
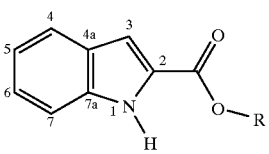

C 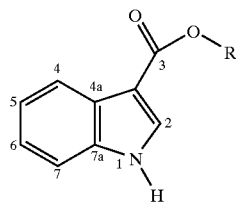

D 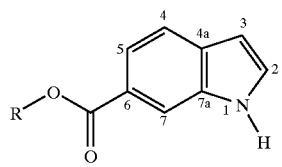

E 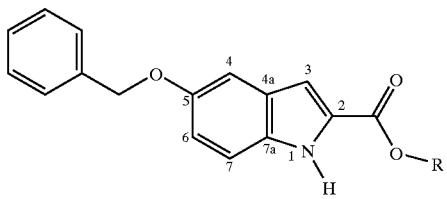

F 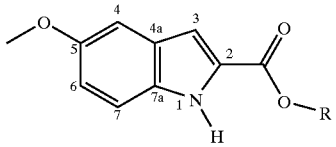

G 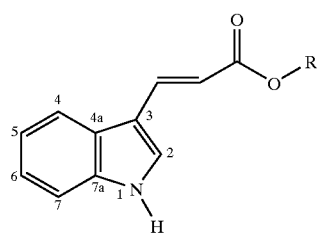

In further separate embodiments of the invention herein, the methods of the invention comprise administering a compound corresponding to the structures set out in Structure 102. For those compounds that correspond to Structure 102, n is an integer of from 1 to 12, from 3 to 10, more preferably from 5 to 9, and still more preferably from 6 to 9. In further embodiments, the compounds herein correspond to Structure 102, as further set out in Table 102.

STRUCTURE 102:

TABLE 102

SUBSTITUENT GROUPS FOR COMPOUNDS 25–48

| R' n⁻ | 4 | 6 | 8 |
|---|---|---|---|
| I | 25 | 26 | 27 |
| I* | 28 | 29 | 30 |
| II | 31 | 32 | 33 |
| III* | 34 | 35 | 36 |
| VII | 37 | 38 | 39 |

TABLE 102-continued

SUBSTITUENT GROUPS FOR COMPOUNDS 25–48

| R' n⁻ | 4 | 6 | 8 |
|---|---|---|---|
| VII* | 40 | 41 | 42 |
| VIII | 43 | 44 | 45 |
| VIII* | 46 | 47 | 48 |

In the above Table, R' corresponds to a Fragment as previously defined in FIG. 6, A corresponds to a Fragment as previously defined in FIG. 8, and n indicates the number of linker groups separating Groups R' and A in the respective compounds. Groups I, II, VII, VIII each have a benzyl group and Groups I*, III*, VII*, VIII* each have a hydrogen, respectively, in the position designated R in Fragment A of FIG. 8.

In further separate embodiments of the invention herein, the methods of the invention comprise administering a compound corresponding to the structures set out in Structure 104. For those compounds that correspond to Structure 104, n is an integer of from 1 to 12, from 3 to 10, more preferably from 5 to 9, and still more preferably from 6 to 9. In further embodiments, the compounds herein correspond to Structure 104, as further set out in Table 104.

STRUCTURE 104:

TABLE 104

SUBSTITUENT GROUPS FOR COMPOUNDS 49–66

| R' n⁻ | 4 | 6 | 8 |
|---|---|---|---|
| I | 49 | 50 | 51 |
| I* | 52 | 53 | 54 |
| VII | 55 | 56 | 57 |
| VII* | 58 | 59 | 60 |
| VIII | 61 | 62 | 63 |
| VIII* | 64 | 65 | 66 |

In the above Table, R' corresponds to a Fragment as previously defined in FIG. 6, B corresponds to a Fragment as previously defined in FIG. 8, and n indicates the number of linker groups separating Groups R' and B in the respective compounds. Groups I, VII, VIII each have a benzyl group and Groups I*, VII*, VIII* each have a hydrogen, respectively, in the position designated R in Fragment B of FIG. 8.

In further separate embodiments of the invention herein, the methods of the invention comprise administering a compound corresponding to the structures set out in Structure 106. For those compounds that correspond to Structure 106, n is an integer of from 1 to 12, from 3 to 10, more preferably from 5 to 9, and still more preferably from 6 to 9. In further embodiments, the compounds herein correspond to Structure 106, as further set out in Table 106.

STRUCTURE 106:

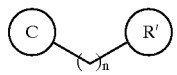

TABLE 106

SUBSTITUENT GROUPS FOR COMPOUNDS 67–90

| R' n⁻ | 4 | 6 | 8 |
|---|---|---|---|
| I | 67 | 68 | 69 |
| I* | 70 | 71 | 72 |
| II | 73 | 74 | 75 |
| III* | 76 | 77 | 78 |
| VII | 79 | 80 | 81 |
| VII* | 82 | 83 | 84 |
| VIII | 85 | 86 | 87 |
| VIII* | 88 | 89 | 90 |

In the above Table, R' corresponds to a Fragment as previously defined in FIG. 6, C corresponds to a Fragment as previously defined in FIG. 8, and n indicates the number of linker groups separating Groups R' and C in the respective compounds. Groups I, II, VII, VIII each have a benzyl group and Groups I*, 1II*, VII*, VIII* each have a hydrogen, respectively, in the position designated R in Fragment C of FIG. 8.

In further separate embodiments of the invention herein, the methods of the invention comprise administering a compound corresponding to the structures set out in Structure 108. For those compounds that correspond to Structure 108, n is an integer of from 1 to 12, from 3 to 10, more preferably from 5 to 9, and still more preferably from 6 to 9. In further embodiments, the compounds herein correspond to Structure 108, as further set out in Table 108.

STRUCTURE 108:

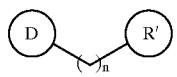

TABLE 108

SUBSTITUENT GROUPS FOR COMPOUNDS 91–108

| R' n⁻ | 4 | 6 | 8 |
|---|---|---|---|
| I | 91 | 92 | 93 |
| I* | 94 | 95 | 96 |
| VII | 97 | 98 | 99 |
| VII* | 100 | 101 | 102 |
| VIII | 103 | 104 | 105 |
| VIII* | 106 | 107 | 108 |

In the above Table, R' corresponds to a Fragment as previously defined in FIG. 6, D corresponds to a fragment as previously defined in FIG. 8, and n indicates the number of linker groups separating Groups R' and D in the compound. Groups I, VII, VIII each have a benzyl group and Groups I*, VII*, VIII* each have a hydrogen, respectively, in the position designated R in Fragment D of FIG. 8.

In further separate embodiments of the invention herein, the methods of the invention comprise administering a compound corresponding to the structures set out in Structure 110. For those compounds that correspond to Structure 110, n is an integer of from 1 to 12, from 3 to 10, more preferably from 5 to 9, and still more preferably from 6 to 9. In further embodiments, the compounds herein correspond to Structure 110, as further set out in Table 110.

STRUCTURE 110:

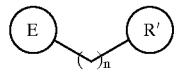

TABLE 110

SUBSTITUENT GROUPS FOR COMPOUNDS 109–126

| R' n⁻ | 4 | 6 | 8 |
|---|---|---|---|
| I | 109 | 110 | 111 |
| I* | 112 | 113 | 114 |
| VII | 115 | 116 | 117 |
| VII* | 118 | 119 | 120 |
| VIII | 121 | 122 | 123 |
| VIII* | 124 | 125 | 126 |

In the above Table, R' corresponds to a Fragment as previously defined in FIG. 6, E corresponds to a Fragment as previously defined in FIG. 8, and n indicates the number of linker groups separating Groups R' and E in the respective compounds. Groups I, VII, VIII each have a benzyl group and Groups I*, VII*, VIII* each have a hydrogen, respectively, in the position designated R in Fragment E of FIG. 8.

In further separate embodiments of the invention herein, the methods of the invention comprise administering a compound corresponding to the structures set out in Structure 112. For those compounds that correspond to Structure 112, n is an integer of from 1 to 12, from 3 to 10, more preferably from 5 to 9, and still more preferably from 6 to 9. In further embodiments, the compounds herein correspond to Structure 112, as further set out in Table 112.

STRUCTURE 112:

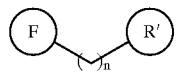

TABLE 112

SUBSTITUENT GROUPS FOR COMPOUNDS 127–144

| R' n⁻ | 4 | 6 | 8 |
|---|---|---|---|
| I | 127 | 128 | 129 |
| I* | 130 | 131 | 132 |
| VII | 133 | 134 | 135 |
| VII* | 136 | 137 | 138 |
| VIII | 139 | 140 | 141 |
| VIII* | 142 | 143 | 144 |

In the above Table, R' corresponds to a Fragment as previously defined in FIG. 6, F corresponds to a Fragment as previously defined in FIG. 8, and n indicates the number of linker groups separating Groups R' and F in the respective compounds. Groups I, VIII each have a benzyl group and Groups I*, VII*, VIII* each have a hydrogen, respectively, in the position designated R in Fragment F of FIG. 8.

In further separate embodiments of the invention herein, the methods of the invention comprise administering a compound corresponding to the structures set out in Structure 114. For those compounds that correspond to Structure 114, n is an integer of from 1 to 12, from 3 to 10, more preferably from 5 to 9, and still more preferably from 6 to 9. In further embodiments, the compounds herein correspond to Structure 114, as further set out in Table 114.

STRUCTURE 114:

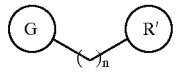

TABLE 114

SUBSTITUENT GROUPS FOR COMPOUNDS 145–162

| R' n⁻ | 4 | 6 | 8 |
|---|---|---|---|
| I | 145 | 146 | 147 |
| I* | 148 | 149 | 150 |
| VII | 151 | 152 | 153 |
| VII* | 154 | 155 | 156 |
| VIII | 157 | 158 | 159 |
| VIII* | 160 | 161 | 162 |

In the above Table, R' corresponds to a Fragment as previously defined in FIG. 6, G corresponds to a Fragment as previously defined in FIG. 8, and n indicates the number of linker groups separating Groups R' and G in the respective compounds. Groups I, VII, VIII each have a benzyl group and Groups I*, VII*, VIII* each have a hydrogen, respectively, in the position designated R in Fragment G of FIG. 8.

In further separate embodiments of the invention herein, the methods of the invention comprise administering a compound corresponding to the structures set out in Structure 116. For those compounds that correspond to Structure 116, n is an integer of from 1 to 12, from 3 to 10, more preferably from 5 to 9, and still more preferably from 6 to 9. In further embodiments, the compounds herein correspond to Structure 116, as further set out in Table 116.

STRUCTURE 116:

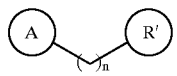

TABLE 116

SUBSTITUENT GROUPS FOR COMPOUNDS 163–178

| R' n⁻ | 3 | 5 | 7 | 9 |
|---|---|---|---|---|
| I | 163 | 164 | 165 | 166 |
| I* | 167 | 168 | 169 | 170 |
| II | 171 | 172 | 173 | 174 |
| III* | 175 | 176 | 177 | 178 |

In the above Table, R' corresponds to a Fragment as previously defined in FIG. 6, A corresponds to a Fragment as previously defined in FIG. 8, and n indicates the number of linker groups separating Groups R' and A in the respective compounds. Groups I, II each have a methyl group and Groups I*, III* each have a hydrogen, respectively, in the position designated R in Fragment A of FIG. 8.

In further separate embodiments of the invention herein, the methods of the invention comprise administering a compound corresponding to the structures set out in Structure 118. For those compounds that correspond to Structure 118, n is an integer of from 1 to 12, from 3 to 10, more preferably from 5 to 9, and still more preferably from 6 to 9. In further embodiments, the compounds herein correspond to Structure 118, as further set out in Table 118.

STRUCTURE 118:

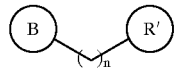

TABLE 118

SUBSTITUENT GROUPS FOR COMPOUNDS 179–194

| R' n⁻ | 3 | 5 | 7 | 9 |
|---|---|---|---|---|
| I | 179 | 180 | 181 | 182 |
| I* | 183 | 184 | 185 | 186 |
| II | 187 | 188 | 189 | 190 |
| III* | 191 | 192 | 193 | 194 |

In the above Table, R' corresponds to a Fragment as previously defined in FIG. 6, B corresponds to a Fragment as previously defined in FIG. 8, and n indicates the number of linker groups separating Groups R' and B in the respective compounds. Groups I, II each have a methyl group and Groups I*, III* each have a hydrogen, respectively, in the position designated R in Fragment B of FIG. 8.

In further separate embodiments of the invention herein, the methods of the invention comprise administering a compound corresponding to the structures set out in Structure 120. For those compounds that correspond to Structure 120, n is an integer of from 1 to 12, from 3 to 10, more preferably from 5 to 9, and still more preferably from 6 to 9. In further embodiments, the compounds herein correspond to Structure 120, as further set out in Table 120.

STRUCTURE 120:

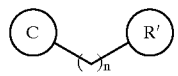

TABLE 120

SUBSTITUENT GROUPS FOR COMPOUNDS 195–210

| R' n⁻ | 3 | 5 | 7 | 9 |
|---|---|---|---|---|
| I | 195 | 196 | 197 | 198 |
| I* | 199 | 200 | 201 | 202 |
| II | 203 | 204 | 205 | 206 |
| III* | 207 | 208 | 209 | 210 |

In the above Table, R' corresponds to a Fragment as previously defined in FIG. 6, C corresponds to a Fragment as previously defined in FIG. 8, and n indicates the number of linker groups separating Groups R' and C in the respective compounds. Groups I, II each have a methyl group and Groups I*, II* each have a hydrogen, repectively, in the position designated R in Fragment C of FIG. 8. invention herein, the methods of the In further separate embodiments of the invention herein, the methods of the invention comprise administering a compound corresponding n Structure 122. For those compounds that correspond to Structure 122, n is an integer of from 1 to 12, from 3 to 10, more preferably from 5 to 9, and still more preferably from 6 to 9. In further embodiments, the compounds herein correspond to Structure 122, as further set out in Table 122.

STRUCTURE 122:

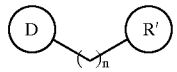

TABLE 122

SUBSTITUENT GROUPS FOR COMPOUNDS 211–226

| R' n= | 3 | 5 | 7 | 9 |
|---|---|---|---|---|
| I | 211 | 212 | 213 | 214 |
| I* | 215 | 216 | 217 | 218 |
| II | 219 | 220 | 221 | 222 |
| III* | 223 | 224 | 225 | 226 |

In the above Table, R' corresponds to a Fragment as previously defined in FIG. 6, D corresponds to a Fragment as previously defined in FIG. 8, and n indicates the number of linker groups separating Groups R' and D in the respective compounds. Groups I, II each have a methyl group and Groups I, III each have a hydrogen, respectively, in the position designated R in Fragment D of FIG. 8.

In further separate embodiments of the invention herein, the methods of the invention comprise administering a compound corresponding to the structures set out in Structure 124. For those compounds that correspond to Structure 124, n is an integer of from 1 to 12, from 3 to 10, more preferably from 5 to 9, and still more preferably from 6 to 9. In further embodiments, the compounds herein correspond to Structure 124, as further set out in Table 124.

STRUCTURE 124:

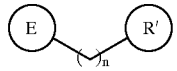

TABLE 124

SUBSTITUENT GROUPS FOR COMPOUNDS 227–242

| | n = | | | |
|---|---|---|---|---|
| R' | 3 | 5 | 7 | 9 |
| I | 227 | 228 | 229 | 230 |
| I* | 231 | 232 | 233 | 234 |
| II | 235 | 236 | 237 | 238 |
| III* | 239 | 240 | 241 | 242 |

In the above Table, R' corresponds to a Fragment as previously defined in FIG. 6, E corresponds to a Fragment as previously defined in FIG. 8, and n indicates the number of linker groups separating Groups R' and E in the respective compounds. Groups I, II each have a methyl group and Groups I*, III* each have a hydrogen, respectively, in the position designated R in Fragment E of FIG. 8.

In further separate embodiments of the invention herein, the methods of the invention comprise administering a compound corresponding to the structures set out in Structure 126. For those compounds that correspond to Structure 126, n is an integer of from 1 to 12, from 3 to 10, more preferably from 5 to 9, and still more preferably from 6 to 9. In further embodiments, the compounds herein correspond to Structure 126, as further set out in Table 126.

STRUCTURE 126:

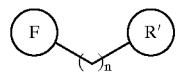

TABLE 126

SUBSTITUENT GROUPS FOR COMPOUNDS 243–258

| | n = | | | |
|---|---|---|---|---|
| R' | 3 | 5 | 7 | 9 |
| I | 243 | 244 | 245 | 246 |
| I* | 247 | 248 | 249 | 250 |
| II | 251 | 252 | 253 | 254 |
| III* | 255 | 256 | 257 | 258 |

In the above Table, R' corresponds to a Fragment as previously defined in FIG. 6, F corresponds to a Fragment as previously defined in FIG. 8, and n indicates the number of linker groups separating Groups R' and F in the respective compounds. Groups I, II each have a methyl group and Groups I*, III* each have a hydrogen, respectively, in the position designated R in Fragment F of FIG. 8.

In further separate embodiments of the invention herein, the methods of the invention comprise administering a compound corresponding to the structures set out in Structure 128. For those compounds that correspond to Structure 128, n is an integer of from 1 to 12, from 3 to 10, more preferably from 5 to 9, and still more preferably from 6 to 9. In further embodiments, the compounds herein correspond to Structure 128, as further set out in Table 128.

STRUCTURE 128:

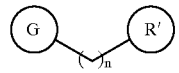

TABLE 128

SUBSTITUENT GROUPS FOR COMPOUNDS 259–274

| | n = | | | |
|---|---|---|---|---|
| R' | 3 | 5 | 7 | 9 |
| I | 259 | 260 | 261 | 262 |
| I* | 263 | 264 | 265 | 266 |
| II | 267 | 268 | 269 | 270 |
| III* | 271 | 272 | 273 | 274 |

In the above Table, R' corresponds to a Fragment as previously defined in FIG. 6, G corresponds to a Fragment as previously defined in FIG. 6, and n indicates the number of linker groups separating Groups R' and G in the respective compounds. Groups I, II each have a methyl group and Groups I*, III* each have a hydrogen, respectively, in the position designated R in Fragment G of FIG. 8.

As used herein, the following terms are defined as follows: Ph: phenyl; I-propyl=isopropyl; OPh=O-Phenyl; and diNO$_2$=dinitric.

In further embodiments, the compounds administered in the methods of the present invention correspond to compounds of the Structure 130 wherein n is an integer of from 1 to 12, from 3 to 10, from 5 to 9 and, still further, from 6 to 9. Further embodiments of the compounds corresponding to Structure 130 are set out in Table 130.

STRUCTURE 130:

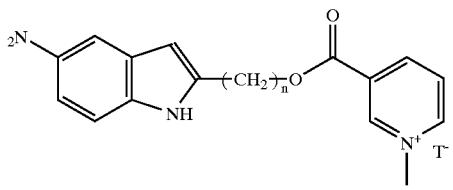

TABLE 130

COMPOUNDS CORRESPONDING TO STRUCTURE 130

| n = | | | | | | |
|---|---|---|---|---|---|---|
| 3 | 4 | 5 | 6 | 7 | 8 | 9 |
| 275 | 276 | 277 | 278 | 279 | 280 | 281 |

In further embodiments, the compounds administered according to the methods of the present invention correspond to compounds of the Structure 132 wherein n is an integer of from 1 to 12, more preferably, from 3 to 10, from 5 to 9 and, still further, from 6 to 9 and wherein and R is 5-H, 6-$CF_3$, 5-$CH_3$, 5,7-diF, 5,7-di$NO_2$, 5-Butyl, 5-iPropyl, 5-Phenyl, 5-$NO_2$, 5-Trityl, 5-F, 5-OPh, 5-COPh, 5-$CF_3$, 5-$COCH_3$, 5-$OCH_3$, 5-$COOCH_3$ or 5-COOH.

Further embodiments of the compounds corresponding to Structure 132 are set out in Table 132.

STRUCTURE 132:

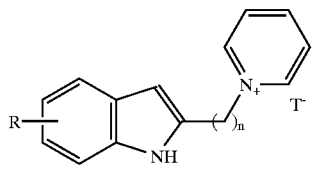

TABLE 132

COMPOUNDS 282–389 CORRESPONDING TO STRUCTURE 132

| | n = | | | | | |
|---|---|---|---|---|---|---|
| R | 3 | 4 | 5 | 6 | 7 | 8 |
| 5-H | 282 | 283 | 284 | 285 | 286 | 287 |
| 6-$CF_3$ | 288 | 289 | 290 | 291 | 292 | 293 |
| 5-$CH_3$ | 294 | 295 | 296 | 297 | 298 | 299 |
| 5,7-diF | 300 | 301 | 302 | 303 | 304 | 305 |
| 5,7-di$NO_2$ | 306 | 307 | 308 | 309 | 310 | 311 |
| 5-Butyl | 312 | 313 | 314 | 315 | 316 | 317 |
| 5-iPropyl | 318 | 319 | 320 | 321 | 322 | 323 |
| 5-Phenyl | 324 | 325 | 326 | 327 | 328 | 329 |
| 5-$NO_2$ | 330 | 331 | 332 | 333 | 334 | 335 |
| 5-Trityl | 336 | 337 | 338 | 339 | 340 | 341 |
| 5-F | 342 | 343 | 344 | 345 | 346 | 347 |
| 5-OPh | 348 | 349 | 350 | 351 | 352 | 353 |
| 5-COPh | 354 | 355 | 356 | 357 | 358 | 359 |
| 5-$CF_3$ | 360 | 361 | 362 | 363 | 364 | 365 |
| 5-$COCH_3$ | 366 | 367 | 368 | 369 | 370 | 371 |
| 5-$OCH_3$ | 372 | 373 | 374 | 375 | 376 | 377 |
| 5-$COOCH_3$ | 378 | 379 | 380 | 381 | 382 | 383 |
| 5-COOH | 384 | 385 | 386 | 387 | 388 | 389 |

In further embodiments, the compounds administered according to the methods of the present invention correspond to compounds of the Structure 134 wherein n is an integer of from 1 to 12, more preferably, from 3 to 10, from 5 to 9 and, still further, from 6 to 9 and wherein R is 5-H, 6-$CF_3$, 5-$CH_3$, 5,7-diF, 5,7-di$NO_2$, 5-Butyl, 5-iPropyl, 5-Phenyl, 5-$NO_2$, 5-Trityl, 5-F, 5-OPh, 5-COPh, 5-$CF_3$, 5-$COCH_3$, 5-$OCH_3$, 5-$COOCH_3$, or 5-COOH. Further embodiments of the compounds corresponding to Structure 134 are set out in Table 134.

STRUCTURE 134:

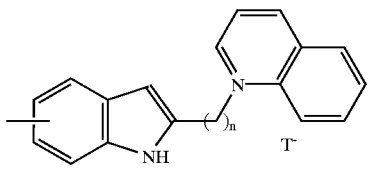

TABLE 134

COMPOUNDS 390–497 CORRESPONDING TO STRUCTURE 134

| | n = | | | | | |
|---|---|---|---|---|---|---|
| R | 3 | 4 | 5 | 6 | 7 | 8 |
| 5-H | 390 | 391 | 392 | 393 | 394 | 395 |
| 5-$CF_3$ | 396 | 397 | 398 | 399 | 400 | 401 |
| 5-$CH_3$ | 402 | 403 | 404 | 405 | 406 | 407 |
| 5,7-diF | 408 | 409 | 410 | 411 | 412 | 413 |
| 5,7-di$NO_2$ | 414 | 415 | 416 | 417 | 418 | 419 |
| 5-Butyl | 420 | 421 | 422 | 423 | 424 | 425 |
| 5-iPropyl | 426 | 427 | 428 | 429 | 430 | 431 |
| 5-Phenyl | 432 | 433 | 434 | 435 | 436 | 437 |
| 5-$NO_2$ | 438 | 439 | 440 | 441 | 442 | 443 |
| 5-Trityl | 444 | 445 | 446 | 447 | 448 | 449 |
| 5-F | 450 | 451 | 452 | 453 | 454 | 455 |
| 5-OPh | 456 | 457 | 458 | 459 | 460 | 461 |
| 5-COPh | 462 | 463 | 464 | 465 | 466 | 467 |
| 5-$CF_3$ | 468 | 469 | 470 | 471 | 472 | 473 |
| 5-$COCH_3$ | 474 | 475 | 476 | 477 | 478 | 479 |
| 5-$OCH_3$ | 480 | 481 | 482 | 483 | 484 | 485 |
| 5-$COOCH_3$ | 486 | 487 | 488 | 489 | 490 | 491 |
| 5-COOH | 492 | 493 | 494 | 495 | 496 | 497 |

In further embodiments, the compounds administered according to the methods of the present invention correspond to compounds of the Structure 136 wherein n is an integer of from 1 to 12, more preferably, from 3 to 10, from 5 to 9 and, still further, from 6 to 9 and wherein R is 5-H, 6-$CF_3$, 5-$CH_3$, 5,7-diF, 5,7-di$NO_2$, 5-Butyl, 5-iPropyl, 5-Phenyl, 5-$NO_2$, 5-Trityl, 5-F, 5-OPh, 5-COPh, 5-$CF_3$, 5-$COCH_3$, 5-$OCH_3$, 5-$COOCH_3$, or 5-COOH. Further embodiments of the compounds corresponding to Structure 136 are set out in Table 136.

STRUCTURE 136:

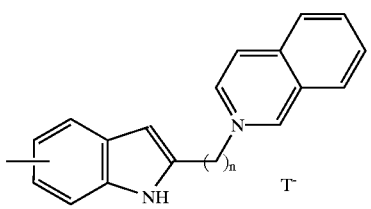

TABLE 136

COMPOUNDS 498–605 CORRESPONDING TO STRUCTURE 136

| R | n = 3 | 4 | 5 | 6 | 7 | 8 |
|---|---|---|---|---|---|---|
| 5-H | 498 | 499 | 500 | 501 | 502 | 503 |
| 6-CF$_3$ | 504 | 505 | 506 | 507 | 508 | 509 |
| 5-CH$_3$ | 510 | 511 | 512 | 513 | 514 | 515 |
| 5,7-diF | 516 | 517 | 518 | 519 | 520 | 521 |
| 5,7-diNO$_2$ | 522 | 523 | 524 | 525 | 526 | 527 |
| 5-Butyl | 528 | 529 | 530 | 531 | 532 | 533 |
| 5-iPropyl | 534 | 535 | 536 | 537 | 538 | 539 |
| 5-Phenyl | 540 | 541 | 542 | 543 | 544 | 545 |
| 5-NO$_2$ | 546 | 547 | 548 | 549 | 550 | 551 |
| 5-Trityl | 552 | 553 | 554 | 555 | 556 | 557 |
| 5-F | 558 | 559 | 560 | 561 | 562 | 563 |
| 5-OPh | 564 | 565 | 566 | 567 | 568 | 569 |
| 5-COPh | 570 | 571 | 572 | 573 | 574 | 575 |
| 5-CF$_3$ | 576 | 577 | 578 | 579 | 580 | 581 |
| 5-COCH$_3$ | 582 | 583 | 584 | 585 | 586 | 587 |
| 5-OCH$_3$ | 588 | 589 | 590 | 591 | 592 | 593 |
| 5-COOCH$_3$ | 594 | 595 | 596 | 597 | 598 | 599 |
| 5-COOH | 600 | 601 | 602 | 603 | 604 | 605 |

In further embodiments, the compounds administered according to the methods of the present invention correspond to compounds of the Structure 138 wherein n is an integer of from 1 to 12, more preferably, from 3 to 10, from 5 to 9 and, still further, from 6 to 9 and wherein R is 5-CF$_3$, 5-OPh, 5-iPropyl, 5-COCH$_3$, or 5-COPh and Y is 3-N,N-dimethylaminophenyl (3-N,N-diCH$_3$), 4-N,N-dimethylaminophenyl (4-N,N-diCH$_3$), or 2-Ph. Further embodiments of the compounds corresponding to Structure 138 are set out in Table 138.

STRUCTURE 138:

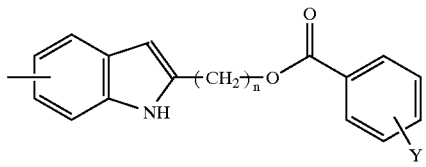

TABLE 138

COMPOUNDS 606–650 CORRESPONDING TO STRUCTURE 138

| R | n = 4 | 7 | 8 | Y |
|---|---|---|---|---|
| 5-CF$_3$ | 606 | 607 | 608 | 3-N,N-DiCH$_3$ |
| 5-CF$_3$ | 609 | 610 | 611 | 4-N,N-DiCH$_3$ |
| 5-CF$_3$ | 612 | 613 | 614 | 2-Ph |

TABLE 138-continued

COMPOUNDS 606–650 CORRESPONDING TO STRUCTURE 138

| R | n = 4 | 7 | 8 | Y |
|---|---|---|---|---|
| 5-OPh | 615 | 616 | 617 | 3-N,N-DiCH$_3$ |
| 5-OPh | 618 | 619 | 620 | 4-N,N-DiCH$_3$ |
| 5-OPh | 621 | 622 | 623 | 2-Ph |
| 5-iPropyl | 624 | 625 | 626 | 3-N,N-DiCH$_3$ |
| 5-iPropyl | 627 | 628 | 629 | 4-N,N-DiCH$_3$ |
| 5-iPropyl | 630 | 631 | 632 | 2-Ph |
| 5-COCH$_3$ | 633 | 634 | 635 | 3-N,N-DiCH$_3$ |
| 5-COCH$_3$ | 636 | 637 | 638 | 4-N,N-DiCH$_3$ |
| 5-COCH$_3$ | 639 | 640 | 641 | 2-Ph |
| 5-COPh | 642 | 643 | 644 | 3-N,N-DiCH$_3$ |
| 5-COPh | 645 | 646 | 647 | 4-N,N-DiCH$_3$ |
| 5-COPh | 648 | 649 | 650 | 2-Ph |

In further embodiments, the compounds administered according to the methods of the present invention correspond to compounds of the Structure 140 wherein n is an integer of from 1 to 12, more preferably, from 3 to 10, from 5 to 9 and, still further, from 6 to 9 and wherein R is 5-CF$_3$, 5-OPh, 5-iPropyl, 5-COCH$_3$ or 5-COPh, and Z is CH(Ph)$_2$ or 3-Pyridyl. Further embodiments of the compounds corresponding to Structure 140 are set out in Table 140.

STRUCTURE 140:

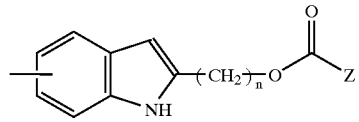

TABLE 140

COMPOUNDS 651–680 CORRESPONDING TO STRUCTURE 140

| R | n = 4 | 7 | 8 | Y |
|---|---|---|---|---|
| 5-CF$_3$ | 651 | 652 | 653 | CH(Ph)$_2$ |
| 5-CF$_3$ | 654 | 655 | 656 | 3-Pyridyl |
| 5-OPh | 657 | 658 | 659 | CH(Ph)$_2$ |
| 5-OPh | 660 | 661 | 662 | 3-Pyridyl |
| 5-iPropyl | 663 | 664 | 665 | CH(Ph)$_2$ |
| 5-iPropyl | 666 | 667 | 668 | 3-Pyridyl |
| 5-COCH$_3$ | 669 | 670 | 671 | CH(Ph)$_2$ |
| 5-COCH$_3$ | 672 | 673 | 674 | 3-Pyridyl |
| 5-COPh | 675 | 676 | 677 | CH(Ph)$_2$ |
| 5-COPh | 678 | 679 | 680 | 3-Pyridyl |

In further embodiments, the compounds administered according to the methods of the present invention correspond to compounds of the Structure 142 wherein n is an integer of from 1 to 12, more preferably, from 3 to 10, from 5 to 9 and, still further, from 6 to 9 and wherein R is 6-CF$_3$, 5-OPh, 5-iPropyl, 5-COCH$_3$, or 5-COPh. Further embodiments of the compounds corresponding to Structure 142 are set out in Table 142.

STRUCTURE 142:

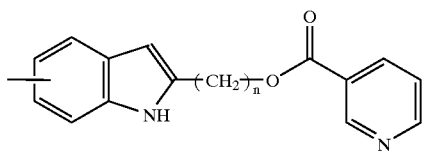

TABLE 142

COMPOUNDS 681–695 CORRESPONDING TO STRUCTURE 142

| R | n = 4 | n = 7 | n = 8 |
|---|---|---|---|
| 5-CF$_3$ | 681 | 682 | 683 |
| 5-OPh | 684 | 685 | 686 |
| 5-iPropyl | 687 | 688 | 689 |
| 5-COCH$_3$ | 690 | 691 | 692 |
| 5-COPh | 693 | 694 | 695 |

In further embodiments, the compounds administered according to the methods of the present invention correspond to compounds of the Structure 144 wherein n is an integer of from 1 to 12, more preferably, from 3 to 10, from 5 to 9 and, still further, from 6 to 9 and wherein R is 6-CF$_3$, 5-OPh, 5-iPropyl, 5-COCH$_3$, or 5-COPh. Further embodiments of the compounds corresponding to Structure 144 are set out in Table 144.

STRUCTURE 144:

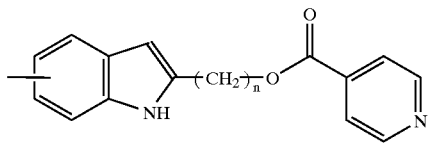

TABLE 144

COMPOUNDS 696–710 CORRESPONDING TO STRUCTURE 144

| R | n = 4 | n = 7 | n = 8 |
|---|---|---|---|
| 6-CF$_3$ | 696 | 697 | 698 |
| 5-OPh | 699 | 700 | 701 |
| 5-iPropyl | 702 | 703 | 704 |
| 5-COCH$_3$ | 705 | 706 | 707 |
| 5-COPh | 708 | 709 | 710 |

In further embodiments, the compounds administered according to the methods of the present invention correspond to compounds of the Structure 146 wherein n is an integer of from 1 to 12, from 3 to 10, from 5 to 9 and, still further, from 6 to 9. Further embodiments of the compounds corresponding to Structure 146 are set out in Table 146.

STRUCTURE 146:

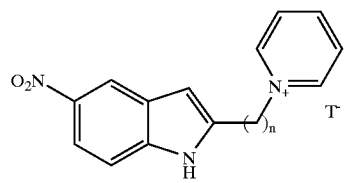

TABLE 146

COMPOUNDS 711–714 CORRESPONDING TO STRUCTURE 146

| n = 3 | n = 4 | n = 5 | n = 8 |
|---|---|---|---|
| 711 | 712 | 713 | 714 |

In further embodiments, the compounds administered according to the methods of the present invention correspond to compounds of the Structure 148, as further defined in Table 148.

STRUCTURE 148:

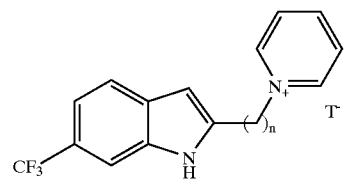

TABLE 148:
COMPOUND 715 CORRESPONDING TO STRUCTURE 148

| 715 |
|---|

In further embodiments, the compounds administered according to the methods of the present invention correspond to compounds of the Structure 150 wherein n is an integer of from 1 to 12, from 3 to 10, from 5 to 9 and, still further, from 6 to 9. Further embodiments of the compounds corresponding to Structure 150 are set out in Table 150.

STRUCTURE 150:

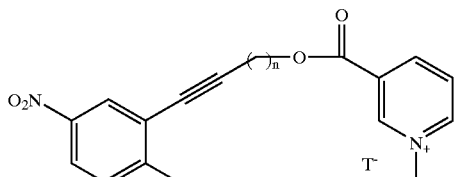

TABLE 150

| COMPOUNDS 716–718 CORRESPONDING TO STRUCTURE 150 | | |
|---|---|---|
| n = | | |
| 2 | 3 | 4 |
| 716 | 717 | 718 |

In further embodiments, the compounds administered according to the methods of the present invention correspond to compounds of the Structure 152 wherein n is an integer of from 1 to 12, from 3 to 10, from 5 to 9 and, still further, from 6 to 9. Further embodiments of the compounds corresponding to Structure 152 are set out in Table 152.

STRUCTURE 152:

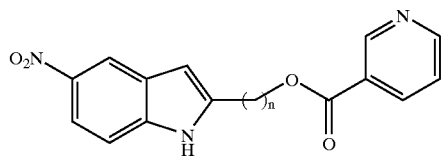

TABLE 152

| COMPOUNDS 719–725 CORRESPONDING TO STRUCTURE 152 | | | | | | |
|---|---|---|---|---|---|---|
| n = | | | | | | |
| 3 | 4 | 5 | 6 | 7 | 8 | 9 |
| 719 | 720 | 721 | 722 | 723 | 724 | 725 |

In further embodiments, the compounds administered according to the methods of the present invention correspond to compounds of the Structure 154 wherein n is an integer of from 1 to 12, more preferably, from 3 to 10, from 5 to 9 and, still further, from 6 to 9 and wherein Z is CH(DiPh), 4-(N,N-dimethylamino)phenyl, $CH_2CH_2$-(3-pyridyl), or (2-phenyl)-phenyl. Further embodiments of the compounds corresponding to Structure 154 are set out in Table 154.

STRUCTURE 154:

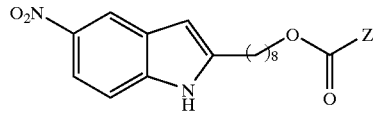

TABLE 154

| COMPOUNDS 726–729 CORRESPONDING TO STRUCTURE 154 | | | |
|---|---|---|---|
| Z = | | | |
| CH(Diph) | (4-N,N-DICH$_3$)phenyl | CH$_2$CH$_2$—(3-pyridyl) | (2-phenyl)-phenyl |
| 726 | 727 | 728 | 729 |

In further embodiments, the compounds administered according to the methods of the present invention correspond to compounds of the Structure 156 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 156 are set out in Table 156.

STRUCTURE 156:

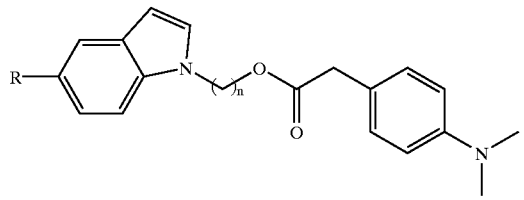

TABLE 156

| COMPOUNDS 730–739 CORRESPONDING TO STRUCTURE 156 | | | | | |
|---|---|---|---|---|---|
| | n = | | | | |
| R | 4 | 5 | 6 | 7 | 8 |
| —OCH$_3$ | 730 | 731 | 732 | 733 | 734 |
| —OCH$_2$Ph | 735 | 736 | 737 | 738 | 739 |

In further embodiments, the compounds administered according to the methods of the present invention correspond to compounds of the Structure 158 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 158 are set out in Table 158.

STRUCTURE 158:

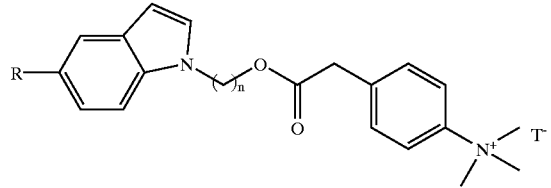

TABLE 158

| COMPOUNDS 740–749 CORRESPONDING TO STRUCTURE 158 | | | | | |
|---|---|---|---|---|---|
| | n = | | | | |
| R | 4 | 5 | 6 | 7 | 8 |
| —OCH$_3$ | 740 | 741 | 742 | 743 | 744 |
| —OCH$_2$Ph | 745 | 746 | 747 | 748 | 749 |

In further embodiments, the compounds administered according to the methods of the present invention correspond to compounds of the Structure 160 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 160 are set out in Table 160.

STRUCTURE 160:

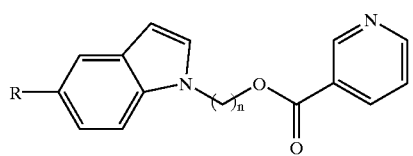

TABLE 160

COMPOUNDS 750–759 CORRESPONDING TO STRUCTURE 160

| R | n = 4 | 5 | 6 | 7 | 8 |
|---|---|---|---|---|---|
| —OCH$_3$ | 750 | 751 | 752 | 753 | 754 |
| —OCH$_2$Ph | 755 | 756 | 757 | 758 | 759 |

In further embodiments, the compounds administered according to the methods of the present invention correspond to compounds of the Structure 162 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 162 are set out in Table 162.

STRUCTURE 162:

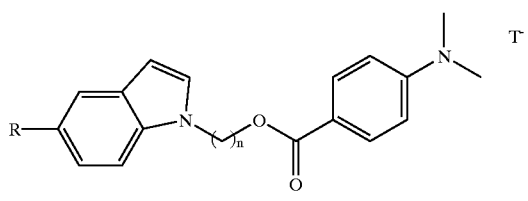

TABLE 162

COMPOUNDS 760–769 CORRESPONDING TO STRUCTURE 162

| R | n = 4 | 5 | 6 | 7 | 8 |
|---|---|---|---|---|---|
| —OCH$_3$ | 760 | 761 | 762 | 763 | 764 |
| —OCH$_2$Ph | 765 | 766 | 767 | 768 | 769 |

In further embodiments, the compounds administered according to the methods of the present invention correspond to compounds of the Structure 164 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 164 are set out in Table 164.

STRUCTURE 164:

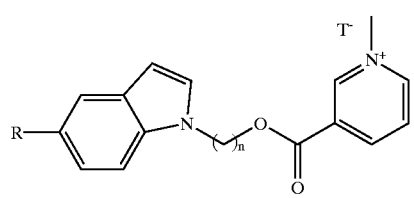

TABLE 164

COMPOUNDS 770–779 CORRESPONDING TO STRUCTURE 164

| R | n = 4 | 5 | 6 | 7 | 8 |
|---|---|---|---|---|---|
| —OCH$_3$ | 770 | 771 | 772 | 773 | 774 |
| —OCH$_2$Ph | 775 | 776 | 777 | 778 | 779 |

In further embodiments, the compounds administered according to the methods of the present invention correspond to compounds of the Structure 166 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 166 are set out in Table 166.

STRUCTURE 166:

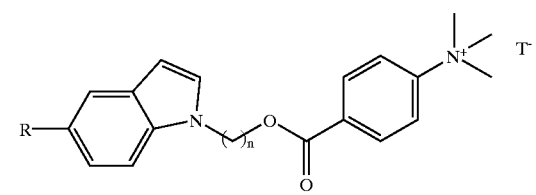

TABLE 166

COMPOUNDS 780–789 CORRESPONDING TO STRUCTURE 166

| R | n = 4 | 5 | 6 | 7 | 8 |
|---|---|---|---|---|---|
| —OCH$_3$ | 780 | 781 | 782 | 783 | 784 |
| —OCH$_2$Ph | 785 | 786 | 787 | 788 | 789 |

In further embodiments, the compounds administered according to the methods of the present invention correspond to compounds of the Structure 168 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 168 are set out in Table 168.

STRUCTURE 168:

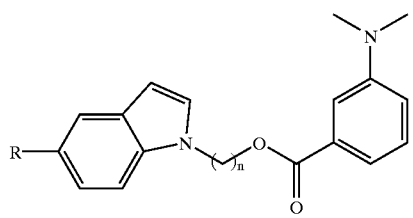

TABLE 168

COMPOUNDS 790–799 CORRESPONDING TO STRUCTURE 168

|  | n = | | | | |
|---|---|---|---|---|---|
| R | 4 | 5 | 6 | 7 | 8 |
| —OCH$_3$ | 790 | 791 | 792 | 793 | 794 |
| —OCH$_2$Ph | 795 | 796 | 797 | 798 | 799 |

In further embodiments, the compounds administered according to the methods of the present invention correspond to compounds of the Structure 170 wherein n is an integer of from 1 to 12, more preferably, from 3 to 10, from 5 to 9 and, still further, from 6 to 9 and wherein R is —OCH$_3$ or —OCH$_2$Ph. Further embodiments of the compounds corresponding to Structure 170 are set out in Table 170.

STRUCTURE 170:

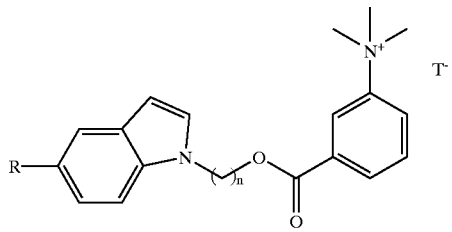

TABLE 170

COMPOUNDS 800–809 CORRESPONDING TO STRUCTURE 170

|  | n = | | | | |
|---|---|---|---|---|---|
| R | 4 | 5 | 6 | 7 | 8 |
| —OCH$_3$ | 800 | 801 | 802 | 803 | 804 |
| —OCH$_2$Ph | 805 | 806 | 807 | 808 | 809 |

In further embodiments, the compounds administered according to the methods of the present invention correspond to compounds of the Structure 172 wherein n is an integer of from 1 to 12, more preferably, from 3 to 10, from 5 to 9 and, still further, from 6 to 9 and wherein R is —OCH$_3$ and —OCH$_2$ Ph. Further embodiments of the compounds corresponding to Structure 172 are set out in Table 172.

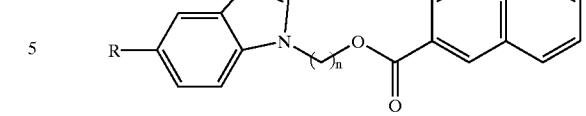

TABLE 172

COMPOUNDS 810–819 CORRESPONDING TO STRUCTURE 172

|  | n = | | | | |
|---|---|---|---|---|---|
| R | 4 | 5 | 6 | 7 | 8 |
| —OCH$_3$ | 810 | 811 | 812 | 813 | 814 |
| —OCH$_2$Ph | 815 | 816 | 817 | 818 | 819 |

In further embodiments, the compounds administered according to the methods of the present invention correspond to compounds of the Structure 174 wherein n is an integer of from 1 to 12, more preferably, from 3 to 10, from 5 to 9 and, still further, from 6 to 9 and wherein R is —OCH$_3$ and —OCH$_2$ Ph. Further embodiments of the compounds corresponding to Structure 174 are set out in Table 174.

STRUCTURE 174:

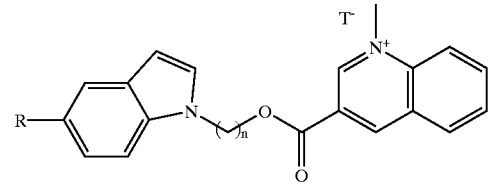

TABLE 174

COMPOUNDS 820–829 CORRESPONDING TO STRUCTURE 174

|  | n = | | | | |
|---|---|---|---|---|---|
| R | 4 | 5 | 6 | 7 | 8 |
| —OCH$_3$ | 820 | 821 | 822 | 823 | 824 |
| —OCH$_2$Ph | 825 | 826 | 827 | 828 | 829 |

In further embodiments, the compounds administered according to the methods of the present invention correspond to compounds of the Structure 176 wherein n is an integer of from 1 to 12, more preferably, from 3 to 10, from 5 to 9 and, still further, from 6 to 9 and wherein Z is 3-quinoline, 3-(N,N-dimethylamino)phenyl, or 4-(N,N-dimethylamino)phenyl. Further embodiments of the compounds corresponding to Structure 176 are set out in Table 176.

STRUCTURE 176:

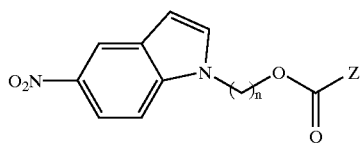

TABLE 176

COMPOUNDS 830–847
CORRESPONDING TO STRUCTURE 176

| Z | n = | | | | | |
|---|---|---|---|---|---|---|
| | 4 | 5 | 6 | 7 | 8 | 9 |
| 3-quinoline | 830 | 831 | 832 | 833 | 834 | 835 |
| 3-(N,N-diCH$_3$) phenyl | 836 | 837 | 838 | 839 | 840 | 841 |
| 4-(N,N-diCH$_3$) phenyl | 842 | 843 | 844 | 845 | 846 | 847 |

In further embodiments, the compounds administered according to the methods of the present invention correspond to compounds of the Structure 178 wherein n is an integer of from 1 to 12, from 3 to 10, from 5 to 9 and, still further, from 6 to 9. Further embodiments of the compounds corresponding to Structure 178 are set out in Table 178.

STRUCTURE 178:

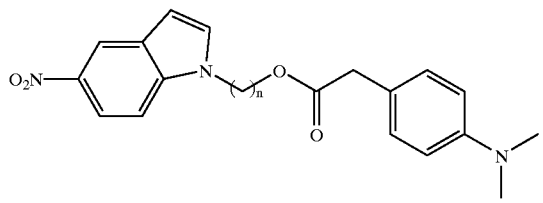

TABLE 178

COMPOUNDS 848–853
CORRESPONDING TO STRUCTURE 178

| N = | 4 | 5 | 6 | 7 | 8 | 9 |
|---|---|---|---|---|---|---|
| | 848 | 849 | 850 | 851 | 852 | 853 |

In further embodiments, the compounds administered according to the methods of the present invention correspond to compounds of the Structure 180 wherein n is an integer of from 1 to 12, from 3 to 10, from 5 to 9 and, still further, from 6 to 9. Further embodiments of the compounds corresponding to Structure 180 are set out in Table 180.

STRUCTURE 180:

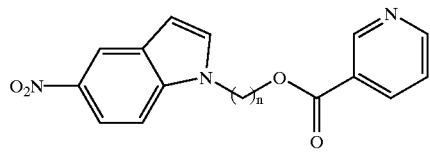

TABLE 180

COMPOUNDS 854–860 CORRESPONDING TO STRUCTURE 180

| n = | | | | | | |
|---|---|---|---|---|---|---|
| 2 | 3 | 4 | 5 | 6 | 7 | 8 |
| 854 | 855 | 856 | 857 | 858 | 859 | 860 |

In further embodiments, the compounds administered according to the methods of the present invention correspond to compounds of the Structure 182 wherein n is an integer of from 1 to 12, from 3 to 10, from 5 to 9 and, still further, from 6 to 9. Further embodiments of the compounds corresponding to Structure 182 are set out in Table 182.

STRUCTURE 182:

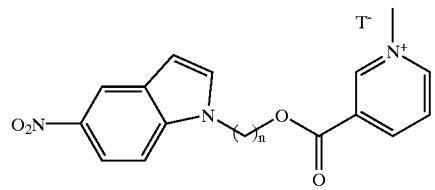

TABLE 182

COMPOUNDS 861–867 CORRESPONDING TO STRUCTURE 182

| n = | | | | | | |
|---|---|---|---|---|---|---|
| 2 | 3 | 4 | 5 | 6 | 7 | 8 |
| 861 | 862 | 863 | 864 | 865 | 866 | 867 |

In further embodiments, the compounds administered according to the methods of the present invention correspond to compounds of the Structure 184 wherein n is an integer of from 1 to 12, more preferably, from 3 to 10, from 5 to 9 and, still further, from 6 to 9 and wherein and R is 6-CF$_3$, 5-OPh, 5-CH(CH$_3$)$_2$, 5-COCH$_3$ or 5-COPh. Further embodiments of the compounds corresponding to Structure 184 are set out in Table 184.

STRUCTURE 184:

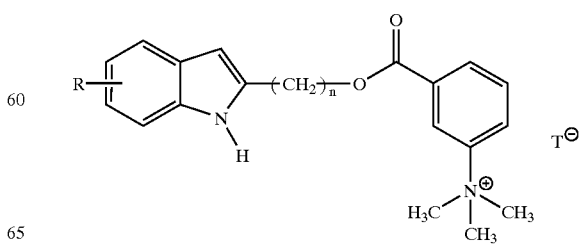

TABLE 184

COMPOUNDS 868–882
CORRESPONDING TO STRUCTURE 184

| R | n = 4 | n = 7 | n = 8 |
|---|---|---|---|
| 6-CF$_3$ | 868 | 869 | 870 |
| 5-OPh | 871 | 872 | 873 |
| 5-CH(CH$_3$)$_2$ | 874 | 875 | 876 |
| 5-COCH$_3$ | 877 | 878 | 879 |
| 5-COPh | 880 | 881 | 882 |

In further embodiments, the compounds administered according to the methods of the present invention correspond to compounds of the Structure 186 wherein n is an integer of from 1 to 12, more preferably, from 3 to 10, from 5 to 9 and, still further, from 6 to 9 and wherein R is 6-CF$_3$, 5-OPh, 5-CH(CH$_3$)$_2$, 5-COCH$_3$ or 5-COPh. Further embodiments of the compounds corresponding to Structure 186 are set out in Table 186.

STRUCTURE 186:

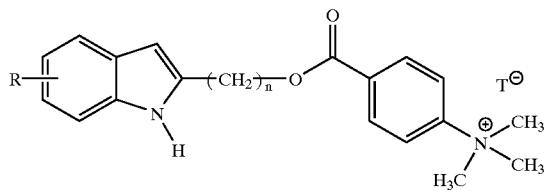

TABLE 186

COMPOUNDS 883–897
CORRESPONDING TO STRUCTURE 186

| R | n = 4 | n = 7 | n = 8 |
|---|---|---|---|
| 6-CF$_3$ | 883 | 884 | 885 |
| 5-OPh | 886 | 887 | 888 |
| 5-CH(CH$_3$)$_2$ | 889 | 890 | 891 |
| 5-COCH$_3$ | 892 | 893 | 894 |
| 5-COPh | 895 | 896 | 897 |

In further embodiments, the compounds administered according to the methods of the present invention correspond to compounds of the Structure 188 wherein n is an integer of from 1 to 12, more preferably, from 3 to 10, from 5 to 9 and, still further, from 6 to 9 and wherein and R is 6-CF$_3$, 5-OPh, 5-CH(CH$_3$)$_2$, 5-COCH$_3$ or 5-COPh. Further embodiments of the compounds corresponding to Structure 188 are set out in Table 188.

STRUCTURE 188:

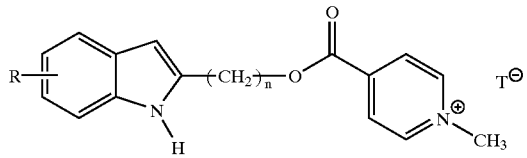

TABLE 188

COMPOUNDS 898–912
CORRESPONDING TO STRUCTURE 188

| R | n = 4 | n = 7 | n = 8 |
|---|---|---|---|
| 6-CF$_3$ | 898 | 899 | 900 |
| 5-OPh | 901 | 902 | 903 |
| 5-CH(CH$_3$)$_2$ | 904 | 905 | 906 |
| 5-COCH$_3$ | 907 | 908 | 909 |
| 5-COPh | 910 | 911 | 912 |

In further embodiments, the compounds administered according to the methods of the present invention correspond to compounds of the Structure 190 wherein n is an integer of from 1 to 12, more preferably, from 3 to 10, from 5 to 9 and, still further, from 6 to 9 and wherein R is 6-CF$_3$, 5-OPh, 5-CH(CH$_3$)$_2$, 5-COCH$_3$ or 5-COPh. Further embodiments of the compounds corresponding to Structure 190 are set out in Table 190.

STRUCTURE 190:

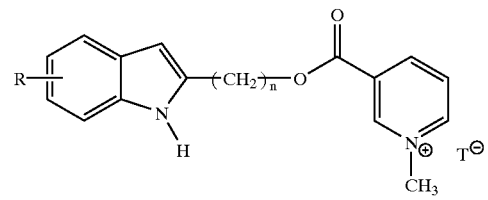

TABLE 190

COMPOUNDS 913–927
CORRESPONDING TO STRUCTURE 190

| R | n = 4 | n = 7 | n = 8 |
|---|---|---|---|
| 6-CF$_3$ | 913 | 914 | 915 |
| 5-OPh | 916 | 917 | 918 |
| 5-CH(CH$_3$)$_2$ | 919 | 920 | 921 |
| 5-COCH$_3$ | 922 | 923 | 924 |
| 5-COPh | 925 | 926 | 927 |

In further embodiments, the compounds administered according to the methods of the present invention correspond to compounds of the Structure 192 wherein n is an integer of from 1 to 12, more preferably, from 3 to 10, from 5 to 9 and, still further, from 6 to 9 and wherein and R is 6-CF$_3$, 5-OPh, 5-CH(CH$_3$)$_2$, 5-COCH$_3$ or 5-COPh. Further embodiments of the compounds corresponding to Structure 192 are set out in Table 192.

STRUCTURE 192:

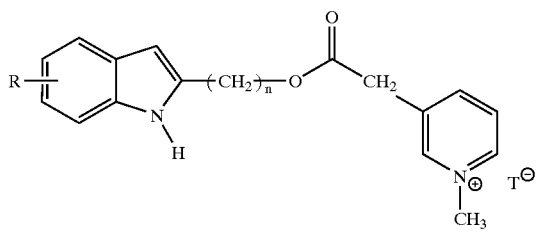

TABLE 192

COMPOUNDS 928–942
CORRESPONDING TO STRUCTURE 192

| | n = | | |
|---|---|---|---|
| R | 4 | 7 | 8 |
| 6-CF$_3$ | 928 | 929 | 930 |
| 5-OPh | 931 | 932 | 933 |
| 5-CH(CH$_3$)$_2$ | 934 | 935 | 936 |
| 5-COCH$_3$ | 937 | 938 | 939 |
| 5-COPh | 940 | 941 | 942 |

In further embodiments, the compounds administered according to the methods of the present invention correspond to compounds of the Structure 194 wherein n is an integer of from 1 to 12, more preferably, from 3 to 10, from 5 to 9 and, still further, from 6 to 9 and R$^1$ is an H or —OCH$_2$Ph and R$^2$ is H or COOCH$_3$. Further embodiments of the compounds corresponding to Structure 194 are set out in Table 194.

STRUCTURE 194:

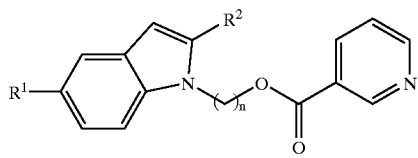

TABLE 194

COMPOUNDS 943–954
CORRESPONDING TO STRUCTURE 194

| | | n = | | | |
|---|---|---|---|---|---|
| R$^1$ | R$^2$ | 6 | 7 | 8 | 9 |
| H | H | 943 | 944 | 945 | 946 |
| H | COOCH$_3$ | 947 | 948 | 949 | 950 |
| —OCH$_2$Ph | COOCH$_3$ | 951 | 952 | 953 | 954 |

In further embodiments, the compounds administered according to the methods the present invention correspond to compounds of the Structure 196 wherein n is an integer of from 1 to 12, more preferably, from 3 to 10, from 5 to 9 and, still further, from 6 to 9 and wherein R$^1$ is an H or a —OCH$_2$Ph and R$_2$ is H or COOCH$_3$. Further embodiments of the compounds corresponding to Structure 196 are set out in Table 196.

STRUCTURE 196:

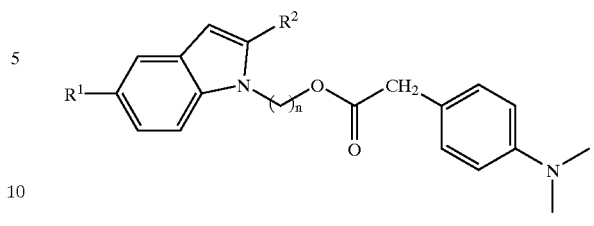

TABLE 196

COMPOUNDS 955–966
CORRESPONDING TO STRUCTURE 196

| | | n = | | | |
|---|---|---|---|---|---|
| R$^1$ | R$^2$ | 6 | 7 | 8 | 9 |
| H | H | 955 | 956 | 957 | 958 |
| H | COOCH$_3$ | 959 | 960 | 961 | 962 |
| —OCH$_2$Ph | COOCH$_3$ | 963 | 964 | 965 | 966 |

In further embodiments, the compounds administered according to the methods of the present invention correspond to compounds of the Structure 198 wherein n is an integer of from 1 to 12, more preferably, from 3 to 10, from 5 to 9 and, still further, from 6 to 9 and wherein R$^1$ is an H or a —OCH$_2$Ph and R$^2$ is H, or COOCH$_3$. Further embodiments of the compounds corresponding to Structure 198 are set out in Table 198.

STRUCTURE 198:

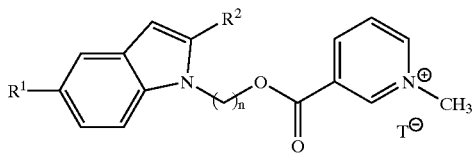

TABLE 198

COMPOUNDS 967–978
CORRESPONDING TO STRUCTURE 198

| | | n = | | | |
|---|---|---|---|---|---|
| R$^1$ | R$^2$ | 6 | 7 | 8 | 9 |
| H | H | 967 | 968 | 969 | 970 |
| H | COOCH$_3$ | 971 | 972 | 973 | 974 |
| —OCH$_2$Ph | COOCH$_3$ | 975 | 976 | 977 | 978 |
| OCPh$_3$ | COOCH$_3$ | | | 1106 | |

In further embodiments, the compounds administered according to the methods of the present invention correspond to compounds of the Structure 200 wherein n is an integer of from 1 to 12, more preferably, from 3 to 10, from 5 to 9 and, still further, from 6 to 9 and wherein R$^1$ is H or a —OCH$_2$Ph and R is H or COOCH$_3$. Further embodiments of the compounds corresponding to Structure 200 are set out in Table 200.

STRUCTURE 200:

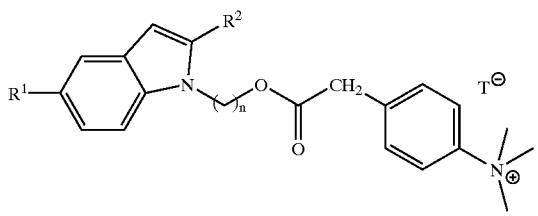

TABLE 200

COMPOUNDS 979–990
CORRESPONDING TO STRUCTURE 200

| | | n = | | | |
|---|---|---|---|---|---|
| $R^1$ | $R^2$ | 6 | 7 | 8 | 9 |
| H | H | 979 | 980 | 981 | 982 |
| H | $COOCH_3$ | 983 | 984 | 985 | 986 |
| $OCH_2Ph$ | $COOCH_3$ | 987 | 988 | 989 | 990 |

In further embodiments, the compounds administered according to the methods of the present invention correspond to compounds of the Structure 202A.

STRUCTURE 202A:

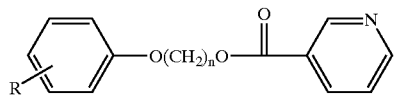

In further embodiments, the compounds administered according to the methods of the present invention correspond to compounds of the Structure 202A wherein n is an integer of from 1 to 12, more preferably, from 3 to 10, from 5 to 9 and, still further, from 6 to 9 and wherein R is H; 4-$NO_2$; 2-CONHPh; 2-$NO_2$; 4-[1' (4'-acetylpiperazine)]; 2-$COCH_3$; 3-$OCOCH_3$; 3-$OCH_3$; 4-$COCH_3$; 3-OCOPh; 2-$CONH_2$; 4-CH=CHCOCH$_3$; 4-OCOPh; 4-CH=CHCOPh; 4-{CO-3'[2'-butylbenzo(b)furan]}; 3-$NO_2$; 4-[5'-(5'-phenylhydantoin)]; 2-CH=CHCOPh; 2-$OCH_3$; 4-COPh; 4-$CONH_2$; 3-$COCH_3$; 4-OPh; 4-(N-Phthalimide); 3-(N-Morpholine); 2-(N-pyrrolidine); 2-(N-Morpholine); or 4-$OCH_2Ph$. Further embodiments of the compounds corresponding to Structure 202 are set out in Table 202.

TABLE 202

COMPOUNDS 991–1021
CORRESPONDING TO STRUCTURE 202A

| R = | n = 4 | n = 7 | n = 8 |
|---|---|---|---|
| H | 991 | 993 | |
| 4-$NO_2$ | 992 | 994 | 995 |
| 2-CONHPh | | | 996 |
| 2-$NO_2$ | | | 997 |
| 4-[1'(4'-acetylpiperazine)] | | | 998 |
| 2-$COCH_3$ | | | 999 |
| 3-$OCOCH_3$ | | | 1000 |
| 3-$OCH_3$ | | | 1001 |
| 4-$COCH_3$ | | | 1002 |
| 3-OCOPh | | | 1003 |
| 2-$CONH_2$ | | | 1004 |

TABLE 202-continued

COMPOUNDS 991–1021
CORRESPONDING TO STRUCTURE 202A

| R = | n = 4 | n = 7 | n = 8 |
|---|---|---|---|
| 4-CH=CHCOCH$_3$ | | | 1005 |
| 4-OCOPh | | | 1006 |
| 4-CH=CHCOPh | | | 1007 |
| 4-{CO-3'[2'-butylbenzo(b)furan]} | | | 1008 |
| 3-$NO_2$ | | | 1009 |
| 4-[5'-(5'-phenylhydantoin)] | | | 1010 |
| 2-CH=CHCOPh | | | 1011 |
| 2-$OCH_3$ | | | 1012 |
| 4-COPh | | | 1013 |
| 4-$CONH_2$ | | | 1014 |
| 3-$COCH_3$ | | | 1015 |
| 4-Oph | | | 1016 |
| 4-(N-phthalimide) | | | 1017 |
| 3-(N-morpholine) | | | 1018 |
| 2-(N-pyrrolidine) | | | 1019 |
| 2-(N-morpholine) | | | 1020 |
| 4-$OCH_2Ph$ | | | 1021 |

In further embodiments, the compounds administered according to the methods of the present invention correspond to compounds of the Structure 204A wherein n is an integer of from 1 to 12, from 3 to 10, from 5 to 9 and, still further, from 6 to 9 and wherein R is 4-$NO_2$; 2-CONHPh; 2-$NO_2$; 4-[1' (4'-acetylpiperazine)]; 2-$COCH_3$; 3-$OCOCH_3$; 3-$OCH_3$; 4-$COCH_3$; 3-OCOPh; 2-$CONH_2$; 4-CH=CHCOCH$_3$; 4-OCOPh; 4-CH=CHCOPh; 4-{CO-3'[2'-butylbenzo(b)furan]}; 3-$NO_2$; 4-[5'-(5'-phenylhydantoin)]; 2-CH=CHCOPh; 2-$OCH_3$; 4-COPh; 4-$CONH_2$; 3-$COCH_3$; 4-OPh; 4-(N-phthalimide); 3-(N-morpholine); 2-(N-pyrrolidine); 2-(N-morpholine); or 4-$OCH_2Ph$. Further embodiments of the compounds corresponding to Structure 204 are set out in Table 204.

STRUCTURE 204A:

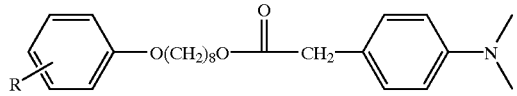

TABLE 204

COMPOUNDS 1022–1048
CORRESPONDING TO STRUCTURE 204A

| R = | |
|---|---|
| 4-$NO_2$ | 1022 |
| 2-CONHPh | 1023 |
| 2-$NO_2$ | 1024 |
| 4-[1'(4'-acetylpiperazine)] | 1025 |
| 2-$COCH_3$ | 1026 |
| 3-$OCOCH_3$ | 1027 |
| 3-$OCH_3$ | 1028 |
| 4-$COCH_3$ | 1029 |
| 3-OCOPh | 1030 |
| 2-$CONH_2$ | 1031 |
| 4-CH=CHCOCH$_3$ | 1032 |
| 4-OCOPh | 1033 |
| 4-CH=CHCOPh | 1034 |
| 4-{CO-3'[2'-butylbenzo(b)furan]} | 1035 |
| 3-$NO_2$ | 1036 |
| 4-[5'-(5'-phenylhydantoin)] | 1037 |
| 2-CH=CHCOPh | 1038 |
| 2-$OCH_3$ | 1039 |
| 4-COPh | 1040 |

TABLE 204-continued

COMPOUNDS 1022–1048
CORRESPONDING TO STRUCTURE 204A

R =

| | |
|---|---|
| 4-CONH$_2$ | 1041 |
| 3-COCH$_3$ | 1042 |
| 4-Oph | 1043 |
| 4-(N-phthalimide) | 1044 |
| 3-(N-morpholine) | 1045 |
| 2-(N-pyrrolidine) | 1046 |
| 2-(N-morpholine) | 1047 |
| 4-OCH$_2$Ph | 1048 |

In further embodiments, the compounds administered according to the methods of the present invention correspond to compounds of the Structure 206 wherein n is an integer of from 1 to 12, from 3 to 10, from 5 to 9 and, still further, from 6 to 9 and 5 wherein R is H; 4-NO$_2$; 2-CONHPh; 2-NO$_2$; 2-COCH$_3$; 3-CH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 2-CH=CHCOPh; 2-OCH$_3$; 4-COPh; 3-COCH$_3$; 4-OPh; 4-(N-phthalimide); or 4-OCH$_2$Ph. Further embodiments of the compounds corresponding to Structure 206 are set out in Table 206.

STRUCTURE 206:

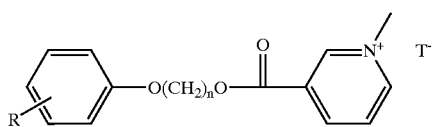

TABLE 206

COMPOUNDS 1049–1068
CORRESPONDING TO STRUCTURE 206

| R = | n = 4 | n = 7 | n = 8 |
|---|---|---|---|
| H | 1049 | 1051 | |
| 4-NO$_2$ | 1050 | 1052 | 1053 |
| 2-CONHPh | | | 3054 |
| 2-NO$_2$ | | | 1055 |
| 2-COCH$_3$ | | | 1056 |
| 3-OCH$_3$ | | | 1057 |
| 4-COCH$_3$ | | | 1058 |
| 3-OCOPh | | | 1059 |
| 2-CONH2 | | | 1060 |
| 4-CH=CHCOCH$_3$ | | | 1061 |
| 4-OCOPh | | | 1062 |
| 4-CH=CHCOPh | | | 1063 |
| 4-{CO-3'[2'-butylbenzo(b)furanl]} | | | 1064 |
| 3-NO$_2$ | | | 1065 |
| 2-CH=CHCOPh | | | 1066 |
| 2-OCH$_3$ | | | 1067 |
| 4-COPh | | | 1068 |
| 3-COCH$_3$ | | | 1069 |
| 4-Oph | | | 1070 |
| 4-(N-phthalimide) | | | 1071 |
| 4-OCH$_2$Ph | | | 1072 |

In further embodiments, the compounds administered according to the methods of the present invention correspond to compounds of the Structure 208 wherein n is an integer of from 1 to 12, from 3 to 10, from 5 to 9 and, still further, from 6 to 9 and wherein R is 4-NO$_2$; 2-CONHPh; 2-NO$_2$; 2-COCH$_3$; 3-OCH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 2-CH=CHCOPh; 2-OCH$_3$; 4-COPh; 3-COCH$_3$; 4-OPh; 4-(N-mhthalimide); 3-(N-morpholine); 2-(N-morpholine); or 4-OCH$_2$Ph. Further embodiments of the compounds corresponding to Structure 208 are set out in Table 208.

STRUCTURE 208:

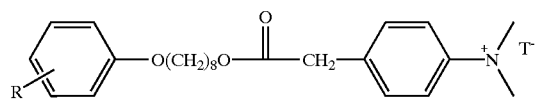

TABLE 208

COMPOUNDS 1073–1094
CORRESPONDING TO STRUCTURE 208

| R = | |
|---|---|
| 4-NO$_2$ | 1073 |
| 2-CONHPh | 1074 |
| 2-NO$_2$ | 1075 |
| 2-COCH$_3$ | 1076 |
| 3-OCH$_3$ | 1077 |
| 4-COCH$_3$ | 1078 |
| 3-OCOPh | 1079 |
| 2-CONH$_2$ | 1080 |
| 4-CH=CHCOCH$_3$ | 1081 |
| 4-OCOPh | 1082 |
| 4-CH=CHCOPh | 1083 |
| 4-{CO-3'[2'-butylbenzo(b)furan]} | 1084 |
| 3-NO$_2$ | 1085 |
| 2-CH=CHCOPh | 1086 |
| 2-OCH$_3$ | 1087 |
| 4-COPh | 1088 |
| 3-COCH$_3$ | 1089 |
| 4-Oph | 1090 |
| 4-(N-phthalimide) | 1091 |
| 3-(N-morpholine) | 1092 |
| 2-(N-morpholine) | 1093 |
| 4-OCH$_2$Ph | 1094 |

In further embodiments, the compounds administered according to the methods of the present invention correspond to compounds of the Structure 210 wherein R is NH$_2$; NMe$_2$; NMe$_3$.I; NH$_2$.HCl; NMe$_2$.HCl. Further embodiments of the compounds corresponding to Structure 210 are set out in Table 210.

STRUCTURE 210:

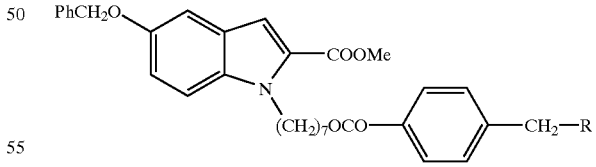

TABLE 210

COMPOUNDS 1095–1099
CORRESPONDING TO STRUCTURES 210

| R = | |
|---|---|
| NH$_2$ | 1095 |
| Nme$_2$ | 1096 |
| Nme$_3$.I— | 1097 |

TABLE 210-continued

COMPOUNDS 1095–1099 CORRESPONDING TO STRUCTURES 210

| R = | |
|---|---|
| NH$_2$.HCl | 1098 |
| NMe$_2$.HCl | 1099 |

In further embodiments, the compounds administered according to the methods of the present invention correspond to compounds of the Structure 212 wherein R' is PhCONH or Ph$_3$C and R" is H or COOCH$_3$. Further embodiments of the compounds corresponding to Structure 212 are set out in Table 212.

STRUCTURE 212:

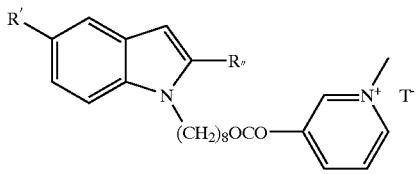

TABLE 212

COMPOUNDS 1100–1101 CORRESPONDING TO STRUCTURE 212

| R' = | R" = | |
|---|---|---|
| PhCONH | H | 1100 |
| Ph$_3$C | COOCH$_3$ | 1101 |

In further embodiments, the compounds administered according to the methods of the present invention correspond to compounds of the Structure 214 wherein R is 4-hydroxyphenyl or 3-hydroxy-4-methylphenyl. Further embodiments of the compounds corresponding to Structure 214 are set out in Table 214.

STRUCTURE 214:

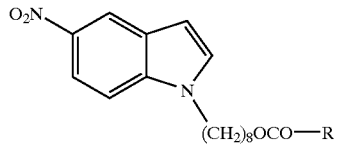

TABLE 214

COMPOUNDS 1102–1103 CORRESPONDING TO STRUCTURE 214

| R = | |
|---|---|
| 4-hydroxyphenyl | 1102 |
| 3-hydroxy-4-methylphenyl | 1103 |

In further embodiments, the compounds administered according to the methods of the present invention correspond to compounds of Structure 216 wherein R' is PhCONH and and R" is H or COOCH$_3$ and n=7 or 8. Further preferred embodiments of the compounds corresponding to Structure 216 are set out in Table 216.

STRUCTURE 216:

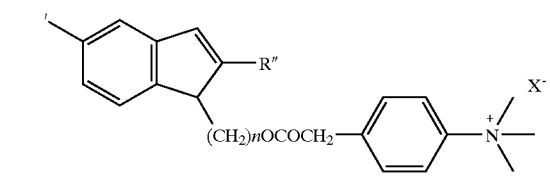

TABLE 216

COMPOUNDS 1104–1105 CORRESPONDING TO STRUCTURE 216

| R' = | R" = | n = | |
|---|---|---|---|
| PhCONH | H | 8 | 1104 |
| PhCH$_2$O | COOCH$_3$ | 7 | 1105 |

Further embodiments of the invention include compounds having Structure 300:

Structure 300

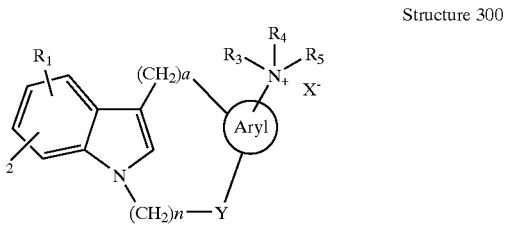

wherein Y is C, N, O, S, ester, amide, or ketone, n is an integer of from 1 to 12, a is an integer from 1–3, and $R_1$–$R_5$ each, independently, is an H, unsubstituted or substituted cyclic group or an aliphatic group, a branched or an unbranched group, or an alkyl, alkenyl, or alkynyl, or an aryl group. $R_1$–$R_2$ may also be an H, hydroxyl, ketone, nitro, amino, amidino, guanidino, carboxylate, amide, ester, sulfonate, halogen, alkoxy, or aryloxy group. The $(CH_2)_n$ linker may be saturated or unsaturated and contain cyclic or aliphatic groups, branched or unbranched alkyl, alkenyl, or alkynyl substituents, and wherein the linker may also contain heteroatoms. The aryl group is an aromatic grouping which may contain one or more rings, and the quaternary nitrogen may be part of the ring (as, for example, in pyridines and quinolines) or outside the ring (as, for example, in anilines and aminonaphthalenes). The value for n may also be an integer of from 3 to 10, more preferably 5 to 9 and, still more preferably 6 to 9.

Specific examples include Structure 1300

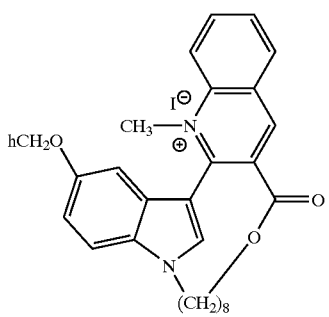

1300

Yet another example of suitable compounds include those having Structure 400:

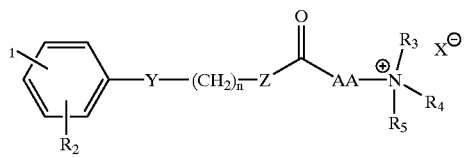

Structure 400 wherein Y is C, N, O, S, ester, amide, or ketone; Z is C, N, O, or S; AA is a natural or unnatural stereoisomer of an α-, β-, γ-, or δ-amino acid in which the carboxyl carbonyl is attached to Z, and the amino grouping may be a primary, secondary, tertiary, or quaternary ammonium compound; n is an integer of from 1 to 12; and $R_1-R_5$ each, independently, is an H, unsubstituted or substituted cyclic group or an aliphatic group, a branched or an unbranched group, or an alkyl, alkenyl, or alkynyl, or an aryl group. $R_1-R_2$ may also be an H, hydroxyl, ketone, nitro, amino, amidino, guanidino, carboxylate, amide, ester, sulfonate, halogen, alkoxy, or aryloxy group. The $(CH2)_n$ linker may be saturated or unsaturated and contain cyclic or aliphatic groups, branched or unbranched alkyl, alkenyl, or alkynyl substituents, and wherein the linker may also contain heteroatoms. The value for n may also be an integer of from 3 to 10, more preferably 5 to 9 and, still more preferably 6 to 9.

Specific examples include Structure 1230:

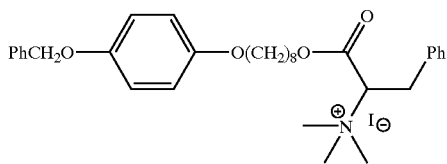

1230 and Structure 1260:

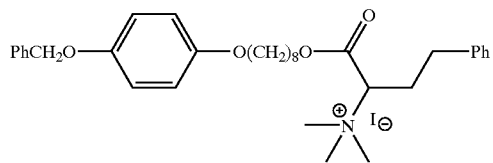

1260

In the method of killing yeast, as well as in the method of decreasing the growth of yeast, the NAD synthetase enzyme inhibitor is a compound that selectively binds with catalytic sites or subsites on a yeast NAD synthetase enzyme to reduce or eliminate the production of NAD by the yeast. In such methods, it is particularly preferable that there is little or no inhibitory activity on the host cell. For example, when the method is utilized to inhibit yeast activity in a mammal, it is preferred that there is little or no attendant affect on the NAD synthetase activity of the host. In one embodiment, the host is a mammal. In a further embodiment, the host is a plant.

In the methods herein, the compound is preferably administered by oral, rectal, intramuscular, intravenous, intravesicular or topical means of administration. The compounds of this invention can be administered to a cell of a subject either in vivo or ex vivo. For administration to a cell of the subject in vivo, as well as for administration to the subject, the compounds of this invention can be administered orally, parenterally (e.g., intravenously), by intramuscular injection, by intraperitoneal injection, subcutaneous injection, transdermally, extracorporeally, topically, mucosally or the like.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected composition, possibly in combination with a pharmaceutically acceptable carrier and, in addition, may include other medicinal agents, pharmaceutical agents, carriers, adjuvants, diluents, etc.

Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. One approach for parenteral administration involves use of a slow release or sustained release system such that a constant dosage is maintained. These compounds can be present in a pharmaceutically acceptable carrier, which can also include a suitable adjuvant. By "pharmaceutically acceptable," it is meant a material that is not biologically or otherwise undesirable, i.e., the material may be administered to an individual along with the selected compound without causing substantial deleterious biological effects or interacting in a deleterious manner with any of the other components of the composition in which it is contained.

Routes of administration for the compounds herein are preferably in a suitable and pharmacologically acceptable formulation. When administered to a human or an animal subject, the yeast NAD synthetase enzyme inhibitor compounds of the invention herein are preferably presented to animals or humans orally, rectally, intramuscularly, intravenously, intravesicularly or topically (including inhalation). The dosage preferably comprises between about 0.1 to about 15 g per day and wherein the dosage is administered from about 1 to about 4 times per day. The preferred dosage may also comprise between 0.001 and 1 g per day, still preferably about 0.01, 0.05, 0.1, and 0.25, 0.5, 0.75 and 1.0 g per day. Further preferably, the dosage may be administered in an amount of about 1, 2.5, 5.0, 7.5,10.0, 12.5 and 15.0 g per day. The dosage may be administered at a still preferable rate of about 1, 2, 3, 4 or more times per day. Further, in some circumstances, it may be preferable to administer the compounds invention continuously, as with, for example, intravenous administration. The exact amount of the compound required will vary from subject to subject, depending on the species, age, weight and general condition of the subject, the particular compound used, its mode of administration and the like. Thus, it is not possible to specify an exact amount for every compound. However, an appropriate amount can be determined by one of ordinary skill in the art using only routine experimentation given the teachings herein.

If ex vivo methods are employed, cells or tissues can be removed and maintained outside the subject's body according to standard protocols well known in the art. The compounds of this invention can be introduced into the cells via known mechanisms for uptake of small molecules into cells (e.g., phagocytosis, pulsing onto class I MHC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

EXAMPLES

The following examples are set forth so as to provide those of ordinary skill in the art with a complete disclosure and description of how the compositions and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

NAD Synthetase Enzyme Inhibition Assay- Determination of Test Compound Concentrations Providing 50% Inhibition (ICL) of the Maximum Enzyme Rate The potential inhibitory activity of the synthetic compounds was determined by the use of a coupled enzymatic assay. The coupled assay involves two steps as summarized below.

Step 1

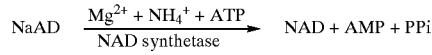

Step 2

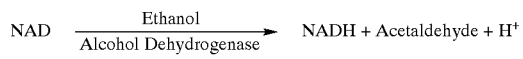

The final reaction mixture includes 0.2 ml of 60 mM HEPPS buffer, pH 8.5, 10 mM MgCl$_2$, 19 mM NH$_4$CL$_2$, 20 mM KCL, 0.1 mM NaAD, 0.3% n-octyl-α-D-glucopyranoside, 1% ethanol, 1 μg/ml NAD synthetase, 62.5 μg/ml yeast alcohol dehydrogenase, 0.2 mM ATP and 2.5% DMSO.

The measurement of inhibitory activities of the test compounds was facilitated by the use of a high through-put screening system (HTS system). The HTS system utilizes an integrated Sagian 2M ORCA robotic system coordinating the functions of a Beckman Biomek 2000 liquid handler and a Molecular Devices SpectraMax Plus spectrophotometer. The 2M ORCA robotic station is responsible for the movement of all hardware and the integration of multiple stations on the worksurface. The Biomek 2000 is programmed to perform all phases of liquid dispensing and mixing. The SpectraMax Plus spectrophotometer is equipped to monitor absorbance in a 96-well plate format.

The current assay is designed for a 96-well plate format and begins with the dispensing of 0.170 mL of reaction buffer containing 60 mM HEPPS buffer, pH 8.5, 10 mM MgCl$_2$, 19 mM NH$_4$CL$_2$, 20 mM KCL, 0.118 mM NaAD, 0.3% n-octyl-α-D-glucopyranoside, 1.18% ethanol, 1.18 μg/ml NAD synthetase (recombinant protein from *B. subtilis*; purified), and 73.75 μg/ml yeast alcohol dehydrogenase. Once the Biomek 2000 has completed this stage of the liquid handling, a 0.005 ml volume of test compound in 100% DMSO or a 0.005 ml of DMSO will be dispensed in the reaction well. The Biomek 2000 mixes these components utilizing a predefined mixing program. The reaction is initiated by the addition of 0.025 ml of a solution of 1.6 mM ATP dissolved in 60 mM HEPPS buffer, pH 8.5, 10 mM MgCl$_2$, 19 mM NH$_4$CL$_2$, 20 mM KCL, 2.5% DMSO, and 0.3% n-Octyl-α-D-Glucopyranoside. The reaction is monitored by measuring the increase in absorbance at 340 nm (NADH). The linear portion of the reaction is monitored for 180 sec. The initial velocity is determined using Softmax Pro, the software supplied with the Molecular Devices SpectrMax Plus spectrophotometer.

The test compounds were supplied as a stock solution with a concentration of 50 mM dissolved in 100% dimethyl sulfoxide (DMSO). An initial screen was conducted on all compounds using a 2 or 3 concentration screen. The 2 panel screen used concentrations of 0.2 mM and 0.1 mM for the compounds. The 3 panel screen used concentrations of 0.2 mM, 0.1 mM, and 0.05 mM. From the initial screen, compounds which indicated the greatest inhibitory capacity were then subjected to a wider screen of concentrations (0.1 mM to 0.005 mM). The IC$_{50}$ values for each compound were determined graphically from a plot of % inhibition versus rate.

TABLE 1

Enzyme Inhibition Data for Selected Compounds: Concentration of Test Compounds Producing 50% Inhibition (IC$_{50}$) of the NAD Synthetase Enzyme Rate

| Compound | IC$_{50}$ (μM) |
| --- | --- |
| 769 | 20 |
| 749 | 25 |
| 230 | 12 |
| 976 | 20 |
| 977 | 10 |
| 984 | 20 |
| 985 | 15 |
| 986 | 10 |
| 988 | 10 |
| 970 | 20 |
| 1094 | 20 |

Example 2

Determination of Minimum Inhibitory Concentration (MIC) Against Yeast

*Candida albicans* (ATCC 10231), *Candida tropicalis* (ATCC 28707-amphotericin B-resistant) and *Candida tropi-*

*calis* (ATCC 750) from stock culture were subcultured on Sabouraud dextrose agar plates for 2 days at 37° C. in ambient air. At least 5 colonies from each of the cultures were inoculated into 3 mL of an approriate broth and thoroughly mixed. One-tenth mL of this suspension was transferred into 10 mL of the appropriate broth and incubated on a shaking incubator at 37° C. for 5–6 hours. Each suspension of the yeast was then adjusted with sterile saline to contain approximately $5 \times 10^8$ CFU/mL.

Test compounds (antifungal agents) were prepared as 5 mg/mL stock solutions in 100% dimethyl sulfoxide. This was diluted 1:100 into 4 mL of diluted broth media for a starting concentration of 50 μg/mL. An additional 9 tubes were prepared with each containing 2 mL of the appropriate broth medium. Serial doubling dilutions were performed for each set of 10 tubes by transferring 2 mL of test material from the first tube to the second tube, mixing thoroughly, then transferring 2 mL to the next tube and mixing, until the tenth tube. From the tenth tube, 2 mL of mixture was discarded. Each tube is then inoculated with 0.01 mL of the yeast suspension in broth. Tubes were incubated for 37° C. for 20 hours and then scored for visible growth or no visible growth. The MIC is defined as the concentration of test compound (μg/mL) that completely inhibits growth of yeast. A positive control (without test compound in broth containing 1% DMSO inoculated with 0.01 mL of the suspension in broth) and a sterility control (only broth containing 1% DMSO) were incubated and evaluated under the same conditions. The MIC determinations and controls were performed in duplicate. The MIC values reported in Table 2 are the mean of duplicate results.

TABLE 2

Minimum Inhibitory Concentration (MIC) Against Yeast

| Compound | Candida albicans (ATCC 10231) MIC (μg/mL) | Candida tropicalis (ATCC 28707) MIC (μg/mL) | Candida tropicalis (ATCC 750) MIC (μg/mL) |
|---|---|---|---|
| 769 | 4.7 | 0.098 | 0.098 |
| 749 | 1.6 | | |
| 230 | 0.78 | | |
| 976 | 3.1 | | |
| 977 | 1.6 | | |
| 984 | 0.78 | | |
| 985 | 1.6 | | |
| 986 | 2.3 | | |
| 988 | 0.10 | 0.15 | 0.024 |
| 970 | 0.8 | | |
| 1094 | 6.2 | 0.78 | 0.78 |

Example 3

In vivo Toxicity: Intraperitoneal (IP) Dosage in Mice Rsulting in 50% Lethality ($LD_{50}$)

Male CD-1 mice (Charles River Labs) at age 4–6 weeks with a body weight of about 25 g were divided into groups of 5 mice each. Animals were fed with commecial diet and water ad lib. Each group of 5 mice received, intraperitoneally (IP), a single dosage of 0, 31.25, 62.5, 125, 250, 500, and 1,000 mg/kg compound. Test compounds were provided as 400 mg/mL stock solutions in 100% dimethyl sulfoxide (DMSO). An equivalent volume was injected into each animal. Animals were observed for 14 days following injection, and body weight was measured every other day. The LD50 was determined from a plot of death rate (%) versus log dose (mg/kg).

TABLE 3

In Vivo Toxicity for Selected Antifungal Compounds In Mice.

| Compound | $LD_{50}$ (mg/kg) |
|---|---|
| 769 | 43 |
| 230 | 47 |
| 988 | 135 |

Example 4

IN VITRO Study of Inhibition of Growth and Lethality Against Yeast

STRUCTURES OF NAD SYNTHETASE INHIBITORS USED IN THE YEAST ASSAY

| Compound | Structure | $IC_{50}$ (μg/mL) for Inhibit. of NAD Synthetase |
|---|---|---|
| 1096 | PhCH₂O-[indole]-COOCH₃, N-(CH₂)₇OCO-[phenyl]-CH₂N(/\) | 100 |

-continued

STRUCTURES OF NAD SYNTHETASE INHIBITORS USED IN THE YEAST ASSAY

| Compound | Structure | $IC_{50}$ (μg/mL) for Inhibit. of NAD Synthetase |
|---|---|---|
| 1300 | 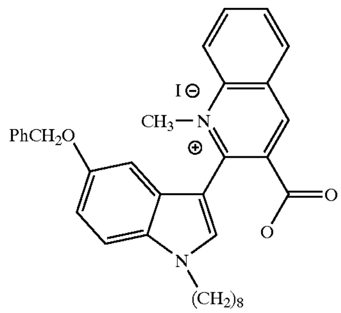 | 66 |
| 988 | 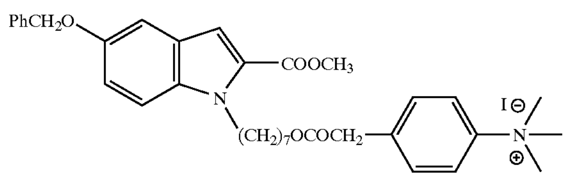 | 10 |
| 769 | 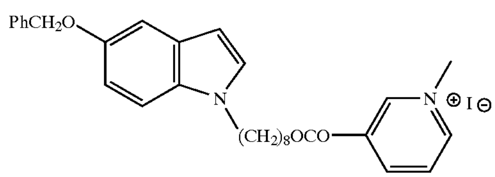 | 20 |
| 1094 | 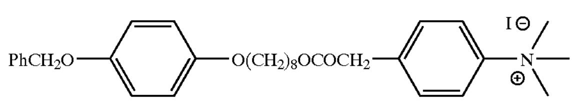 | 20 |
| 1500 | 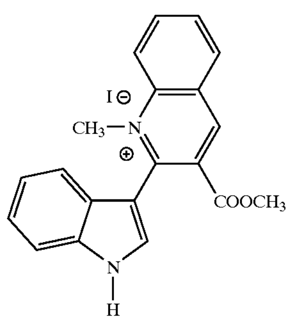 | >200 |
| 230 | 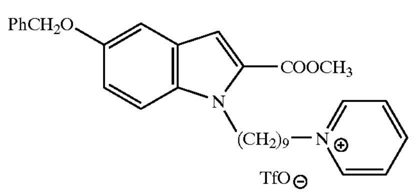 | 10 |

-continued
STRUCTURES OF NAD SYNTHETASE INHIBITORS USED IN THE YEAST ASSAY

| Compound | Structure | $IC_{50}$ (µg/mL) for Inhibit. of NAD Synthetase |
|---|---|---|
| 1400 | 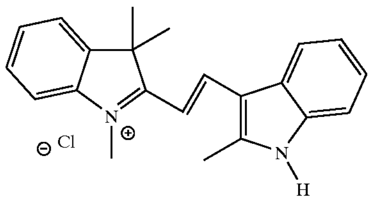 | >200 |
| 1200 | 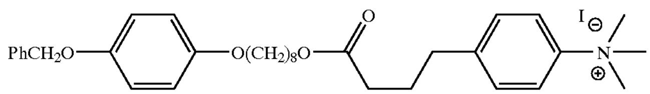 | 35 |
| 1230 | 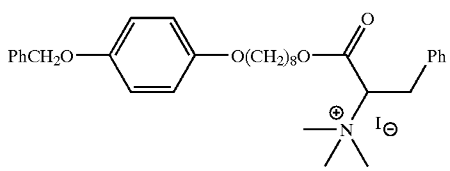 | 20 |
| 1260 | 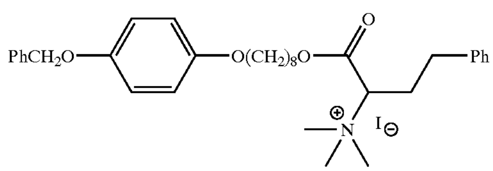 | 30 |

TABLE 4A

RESULTS FOR IN VITRO STUDY OF INHIBITION OF GROWTH AND LETHALITY AGAINST YEAST
Minimum Inhibitory Conc. (MIC; µg/mL) and
Minimum Lethal Conc. (MLC; µg/mL)
Susceptibility Test Against Yeast
*Cryptococcus neoformans* read at 48 and 72 hrs.
All others at 24 and 48 hrs.
MIC value is read at longest time.

| Comp. | Organism | 24 hr. | 48 hr. | 72 hr. | MLC |
|---|---|---|---|---|---|
| 769 | *Candida albicans* | 2 | 2 | | |
| 769 | *Candida albicans* | 1 | 4 | | 8 |
| 769 | *Candida albicans* | 1 | 2 | | |
| 769 | *Candida albicans* | 1 | 2 | | 8 |
| 769 | *Candida tropicalis* | 0.25 | 0.5 | | |
| 769 | *Candida tropicalis* | 0.25 | 0.5 | | 2 |
| 769 | *Candida tropicalis* | 1 | 1 | | |
| 769 | *Candida tropicalis* | 1 | 1 | | 2 |
| 769 | *Cryptococcus neoformans* | | 0.5 | 1 | |
| 769 | *Cryptococcus neoformans* | | 0.5 | 1 | 2 |
| 769 | *Cryptococcus neoformans* | | 0.5 | 0.5 | |
| 769 | *Cryptococcus neoformans* | | 1 | 1 | 2 |
| 769 | *Torulopsis glabrata* | 1 | 2 | | |
| 769 | *Torulopsis glabrata* | 1 | 2 | | 2 |
| 769 | *Torulopsis glabrata* | 0.5 | 1 | | |
| 769 | *Torulopsis glabrata* | 0.5 | 1 | | 1 |
| 230 | *Candida albicans* | 1 | 1 | | |
| 230 | *Candida albicans* | 0.5 | 1 | | 1 |
| 230 | *Candida albicans* | 1 | 1 | | |
| 230 | *Candida albicans* | 1 | 1 | | 1 |
| 230 | *Candida tropicalis* | 0.5 | 0.5 | | |
| 230 | *Candida tropicalis* | 0.5 | 0.5 | | 0.5 |
| 230 | *Candida tropicalis* | 1 | 1 | | |
| 230 | *Candida tropicalis* | 1 | 1 | | 1 |
| 230 | *Cryptococcus neoformans* | | 1 | 1 | |
| 230 | *Cryptococcus neoformans* | | 1 | 1 | 2 |
| 230 | *Cryptococcus neoformans* | | 1 | 1 | |
| 230 | *Cryptococcus neoformans* | | 1 | 1 | 2 |
| 230 | *Torulopsis glabrata* | 1 | 2 | | |
| 230 | *Torulopsis glabrata* | 2 | 2 | | 2 |
| 230 | *Torulopsis glabrata* | 1 | 2 | | |
| 230 | *Torulopsis glabrata* | 2 | 2 | | 2 |
| 988 | *Candida albicans* | 1 | 1 | | |
| 988 | *Candida albicans* | 1 | 1 | | 1 |
| 988 | *Candida albicans* | 1 | 2 | | |
| 988 | *Candida albicans* | 1 | 2 | | 2 |
| 988 | *Candida tropicalis* | 0.5 | 0.5 | | |
| 988 | *Candida tropicalis* | 1 | 1 | | 1 |
| 988 | *Candida tropicalis* | 1 | 1 | | |
| 988 | *Candida tropicalis* | 1 | 1 | | 1 |
| 988 | *Cryptococcus neoformans* | | 1 | 1 | |
| 988 | *Cryptococcus neoformans* | | 1 | 2 | 4 |
| 988 | *Cryptococcus neoformans* | | 1 | 1 | |
| 988 | *Cryptococcus neoformans* | | 1 | 2 | 4 |

TABLE 4A-continued

RESULTS FOR IN VITRO STUDY OF INHIBITION OF
GROWTH AND LETHALITY AGAINST YEAST
Minimum Inhibitory Conc. (MIC; µg/mL) and
Minimum Lethal Conc. (MLC; µg/mL)
Susceptibility Test Against Yeast
*Cryptococcus neoformans* read at 48 and 72 hrs.
All others at 24 and 48 hrs.
MIC value is read at longest time.

| Comp. | Organism | 24 hr. | 48 hr. | 72 hr. | MLC |
|---|---|---|---|---|---|
| 988 | *Torulopsis glabrata* | 2 | 2 | | |
| 988 | *Torulopsis glabrata* | 2 | 2 | | 2 |
| 988 | *Torulopsis glabrata* | 1 | 2 | | |
| 988 | *Torulopsis glabrata* | 2 | 2 | | 2 |
| 1096 | *Candida albicans* | >32 | >32 | | |
| 1096 | *Candida albicans* | >32 | >32 | | >32 |
| 1096 | *Candida albicans* | >32 | >32 | | |
| 1096 | *Candida albicans* | >32 | >32 | | >32 |
| 1096 | *Candida tropicalis* | 4 | 8 | | |
| 1096 | *Candida tropicalis* | 2 | 16 | | 16 |
| 1096 | *Candida tropicalis* | >32 | >32 | | |
| 1096 | *Candida tropicalis* | >32 | >32 | | >32 |
| 1096 | *Cryptococcus neoformans* | | >32 | >32 | |
| 1096 | *Cryptococcus neoformans* | | 8 | 16 | >32 |
| 1096 | *Cryptococcus neoformans* | | >32 | >32 | |
| 1096 | *Cryptococcus neoformans* | | 32 | 32 | >32 |
| 1096 | *Torulopsis glabrata* | >32 | >32 | | |
| 1096 | *Torulopsis glabrata* | >32 | >32 | | >32 |
| 1096 | *Torulopsis glabrata* | >32 | >32 | | |
| 1096 | *Torulopsis glabrata* | >32 | >32 | | >32 |
| 1094 | *Candida albicans* | 1 | 2 | | |
| 1004 | *Candida albicans* | 1 | 1 | | 4 |
| 1094 | *Candida albicans* | 2 | 2 | | |
| 1094 | *Candida albicans* | 2 | 2 | | 8 |
| 1094 | *Candida tropicalis* | 0.5 | 0.5 | | |
| 1094 | *Candida tropicalis* | 0.5 | 0.5 | | 2 |
| 1094 | *Candida tropicalis* | 1 | 1 | | |
| 1094 | *Candida tropicalis* | 1 | 1 | | 4 |
| 1094 | *Cryptococcus neoformans* | | 1 | 1 | |
| 1094 | *Cryptococcus neoformans* | | 1 | 1 | 2 |
| 1094 | *Cryptococcus neoformans* | | 1 | 1 | |
| 1094 | *Cryptococcus neoformans* | | 1 | 1 | 2 |
| 1094 | *Torulopsis glabrata* | 0.5 | 1 | | |
| 1094 | *Torulopsis glabrata* | 1 | 1 | | 4 |
| 1094 | *Torulopsis glabrata* | 0.5 | 1 | | |
| 1094 | *Torulopsis glabrata* | 1 | 1 | | 4 |
| 1300 | *Candida albicans* | 2 | 4 | | |
| 1300 | *Candida albicans* | 2 | 4 | | 8 |
| 1300 | *Candida albicans* | 4 | 4 | | |
| 1300 | *Candida albicans* | 2 | 4 | | 16 |
| 1300 | *Candida tropicalis* | 0.25 | 0.5 | | |
| 1300 | *Candida tropicalis* | 0.5 | 0.5 | | 4 |
| 1300 | *Candida tropicalis* | 2 | 4 | | |
| 1300 | *Candida tropicalis* | 4 | 4 | | 8 |
| 1300 | *Cryptococcus neoformans* | | 8 | 8 | |
| 1300 | *Cryptococcus neoformans* | | 8 | 8 | 16 |
| 1300 | *Cryptococcus neoformans* | | 8 | 8 | |
| 1300 | *Cryptococcus neoformans* | | 8 | 8 | 16 |
| 1300 | *Torulopsis glabrata* | 16 | 16 | | |
| 1300 | *Torulopsis glabrata* | 8 | 16 | | 32 |
| 1300 | *Torulopsis glabrata* | 16 | 16 | | |
| 1300 | *Torulopsis glabraia* | 8 | 16 | | 32 |
| 1230 | *Candida albicans* | 1 | 2 | | |
| 1230 | *Candida albicans* | 1 | 2 | | 2 |
| 1230 | *Candida albicans* | 2 | 4 | | |
| 1230 | *Candida albicans* | 1 | 2 | | 2 |
| 1230 | *Candida tropicalis* | 0.5 | 0.5 | | |
| 1230 | *Candida tropicalis* | 0.5 | 0.5 | | 1 |
| 1230 | *Candida tropicalis* | 1 | 1 | | |
| 1230 | *Candida tropicalis* | 1 | 1 | | 1 |
| 1230 | *Cryptococcus neoformans* | | 1 | 1 | |
| 1230 | *Cryptococcus neoformans* | | 0.5 | 2 | 4 |
| 1230 | *Cryptococcus neoformans* | | 1 | 1 | |
| 1230 | *Cryptococcus neoformans* | | 1 | 2 | 4 |
| 1230 | *Torulopsis glabrata* | 2 | 2 | | |
| 1230 | *Torulopsis glabrata* | 2 | 2 | | 2 |
| 1230 | *Torulopsis glabrata* | 1 | 2 | | |
| 1230 | *Torulopsis glabrata* | 2 | 2 | | 2 |
| 1260 | *Candida albicans* | 2 | 2 | | |
| 1260 | *Candida albicans* | 2 | 2 | | 2 |
| 1260 | *Candida albicans* | 2 | 2 | | |
| 1260 | *Candida albicans* | 2 | 2 | | 4 |
| 1260 | *Candida tropicalis* | 1 | 1 | | |
| 1260 | *Candida tropicalis* | 1 | 1 | | 1 |
| 1200 | *Candida tropicalis* | 2 | 2 | | |
| 1260 | *Candida tropicalis* | 2 | 2 | | 2 |
| 1260 | *Cryptococcus neoformans* | | 1 | 1 | |
| 1260 | *Cryptococcus neoformans* | | 1 | 1 | 2 |
| 1260 | *Cryptococcus neoformans* | | 1 | 1 | |
| 1260 | *Cryptococcus neoformans* | | 1 | 1 | 2 |
| 1260 | *Torulopsis glabrata* | 2 | 2 | | |
| 1260 | *Torulopsis glabrata* | 2 | 2 | | 2 |
| 1260 | *Torulopsis glabrata* | 2 | 2 | | |
| 1260 | *Torulopsis glabrata* | 2 | 2 | | 2 |
| 1200 | *Candida albicans* | 2 | 2 | | |
| 1200 | *Candida albicans* | 2 | 2 | | 2 |
| 1200 | *Candida albicans* | 2 | 2 | | |
| 1200 | *Candida albicans* | 2 | 2 | | 2 |
| 1200 | *Candida tropicalis* | 1 | 1 | | |
| 1200 | *Candida tropicalis* | 1 | 1 | | 1 |
| 1200 | *Candida tropicalis* | 1 | 1 | | |
| 1200 | *Candida tropicalis* | 1 | 1 | | 1 |
| 1200 | *Cryptococcus neoformans* | | 2 | 2 | |
| 1200 | *Cryptococcus neoformans* | | 2 | 2 | 4 |
| 1200 | *Cryptococcus neoformans* | | 2 | 2 | |
| 1200 | *Cryptococcus neoformans* | | 2 | 2 | 4 |
| 1200 | *Torulopsis glabrata* | 1 | 2 | | |
| 1200 | *Torulopsis glabrata* | 1 | 2 | | 2 |
| 1200 | *Torulopsis glabrata* | 1 | 1 | | |
| 1200 | *Torulopsis glabrata* | 1 | 1 | | 1 |
| 1400 | *Candida albicans* | >32 | >32 | | |
| 1400 | *Candida albicans* | >32 | >32 | | >32 |
| 1400 | *Candida albicans* | >32 | >32 | | |
| 1400 | *Candida albicans* | >32 | >32 | | >32 |
| 1400 | *Candida tropicalis* | 16 | 32 | | |
| 1400 | *Candida tropicalis* | 16 | 16 | | 16 |
| 1400 | *Candida tropicalis* | >32 | >32 | | |
| 1400 | *Candida tropicalis* | >32 | >32 | | >32 |
| 1400 | *Cryptococcus neoformans* | | >32 | >32 | |
| 1400 | *Cryptococcus neoformans* | | >32 | >32 | >32 |
| 1400 | *Cryptococcus neoformans* | | >32 | >32 | |
| 1400 | *Cryptococcus neoformans* | | >32 | >32 | >32 |
| 1400 | *Torulopsis glabrata* | >34 | >32 | | |
| 1400 | *Torulopsis glabrata* | >32 | >32 | | >32 |
| 1400 | *Torulopsis glabrata* | >33 | >32 | | |
| 1400 | *Torulopsis glabrata* | >32 | >32 | | >32 |
| 1500 | *Candida albicans* | 32 | >32 | | |
| 1500 | *Candida albicans* | >32 | >32 | | >32 |
| 1500 | *Candida albicans* | 32 | >32 | | |
| 1500 | *Candida albicans* | >32 | >32 | | >32 |
| 1500 | *Candida tropicalis* | 4 | 8 | | |
| 1500 | *Candida tropicalis* | 4 | 8 | | 8 |
| 1500 | *Candida tropicalis* | 32 | >32 | | |
| 1500 | *Candida tropicalis* | >32 | >32 | | >32 |
| 1500 | *Cryptococcus neoformans* | | 32 | 32 | |
| 1500 | *Cryptococcus neoformans* | | 32 | >32 | >32 |
| 1500 | *Cryptococcus neoformans* | | 32 | 32 | |
| 1500 | *Cryptococcus neoformans* | | 32 | >32 | >32 |
| 1500 | *Torulopsis glabrata* | 32 | >32 | | |
| 1500 | *Torulopsis glabrata* | >32 | >32 | | >32 |
| 1500 | *Torulopsis glabrata* | 32 | >32 | | |
| 1500 | *Torulopsis glabrata* | >32 | >32 | | >32 |
| Amphotericin B | *Candida albicans* | 0.5 | 1 | | |
| Amphotericin B | *Candida albicans* | 0.5 | 1 | | |

TABLE 4A-continued

RESULTS FOR IN VITRO STUDY OF INHIBITION OF
GROWTH AND LETHALITY AGAINST YEAST
Minimum Inhibitory Conc. (MIC; µg/mL) and
Minimum Lethal Conc. (MLC; µg/mL)
Susceptibility Test Against Yeast
Cryptococcus neoformans read at 48 and 72 hrs.
All others at 24 and 48 hrs.
MIC value is read at longest time.

| Comp. | Organism | 24 hr. | 48 hr. | 72 hr. | MLC |
|---|---|---|---|---|---|
| Amphotericin B | Candida albicans | 0.5 | 0.5 | | |
| Amphotericin B | Candida albicans | 0.5 | 0.5 | | |
| Amphotericin B | Candida tropicalis | 2 | 4 | | |
| Amphotericin B | Candida tropicalis | 2 | 4 | | |
| Amphotericin B | Candida tropicalis | 0.5 | 0.5 | | |
| Amphotericin B | Candida tropicalis | 0.5 | 1 | | |
| Amphotericin B | Cryptococcus neoformans | | 0.25 | 0.25 | |
| Amphotericin B | Cryptococcus neoformans | | 0.25 | 0.25 | |
| Amphotericin B | Cryptococcus neoformans | | 0.5 | 0.5 | |
| Amphotericin B | Cryptococcus neoformans | | 0.25 | 025 | |
| Amphotericin B | Torulopsis glabrata | 0.5 | 1 | | |
| Amphotericin B | Torulopsis glabrata | 0.5 | 1 | | |
| Amphotericin B | Torulopsis glabrata | 0.5 | 1 | | |
| Amphotericin B | Torulopsis glabrata | 0.5 | 0.5 | | |
| Fluconazole | Candida albicans | 0.5 | 1 | | |
| Fluconazole | Candida albicans | 0.5 | 2 | | |
| Fluconazole | Candida albicans | 0.5 | >64 | | |
| Fluconazole | Candida albicans | >64 | >64 | | |
| Fluconazole | Candida tropicalis | 64 | >64 | | |
| Fluconazole | Candida tropicalis | >64 | >64 | | |
| Fluconazole | Candida tropicalis | 1 | 4 | | |
| Fluconazole | Candida tropicalis | 1 | 4 | | |
| Fluconazole | Cryptococcus neoformans | | >64 | >64 | |
| Fluconazole | Cryptococcus neoformans | | 64 | 64 | |
| Fluconazole | Cryptococcus neoformans | | 4 | 4 | |
| Fluconazole | Cryptococcus neoformans | | 4 | 4 | |
| Fluconazole | Torulopsis glabrata | 64 | >64 | | |
| Fluconazole | Torulopsis glabrata | >64 | >64 | | |
| Fluconazole | Torulopsis glabrata | 2 | 8 | | |
| Fluconazole | Torulopsis glabrata | 2 | 4 | | |

| ISOLATE | ORGANISM |
|---|---|
| A | ATCC 750 | Candida tropicalis |
| B | ATCC 28707 | Candida tropicalis |
| C | KJP-000531594 | Candida albicans |
| D | LH-000664533 | Candida albicans |
| E | JHC-BC9951635 | Torulopsis glabrata |
| F | ERH-BC9938274 | Torulopsis glabrata |
| G | DLB-1027594CNC | Cryptococcus neoformans |
| H | SLP-BC0012854 | Cryptococcus neoformans |

The invention has been described in detail with particular reference to preferred embodiments thereof, but it will be understood that variations and modifications can be effected without departing from the scope and spirit of the invention.

Throughout this application, where publications are referenced, the disclosures of these publications in their entireties are hereby incorporated by reference into this application to more fully describe the state of the art to which this invention pertains.

REFERENCES

1. E. G. Weinberg, "Antifungal Agents," in W. O. Foye, T. L. Lemke, and D. A. Williams, *Principles of Medicinal Chemistry*, $4^{th}$ edition, Williams and Jenkins, Media, Pa., 1995, pp. 803–811.

2. N. H. Georgopapadakou, *Curr. Opin. Microbiol.*, 1, 547–557 (1998).

3. (a) A. H. Groll and T. J. Walsh, *Curr. Opin. Infect. Dis.*, 10, 449 (1997). (b) C. A. Kauffman and P1 L. Carver, *Drugs*, 53, 539 (1997).

4. K. Richardson, "Fluconazole, an Orally Active Antifungal Agent," in C. R. Ganellin and S. M. Roberts, *Medicinal Chemistry*, $2^{nd}$ ed., Academic Press, San Diego, 1993.

5. (a) B. C. Monk and D. S. Perlin, *Crit. Rev. Microbiol.*, 20, 209 (1994). (b) B. C. Monk, A. B. Mason, T. B. Kardos, and D. S. Perlin, *Acta Biochim. Pol.*, 42, 481 (1995).

6. (a) J. Fostel and D. Montgomery, *Antimicro. Agents Chemother.*, 39, 586 (1995). (b) J. Fostel, D. Montgomery, and P. Lartey, *FEMS Microbiol. Lett.*, 138, 105 (1996).

7. M. Rizzi, C. Nessi, A. Mattevi, A. Coda, M. Bolognesi, and A. Galizzi, *The EMBO Journal*, 15, 5125–5134 (1996).

8. C. K. Yu and L. S. Dietrich, *J. Biol. Chem.*, 247, 4794–4802 (1972).

9. W. J. Brouillette et al., "Methods of Synthesizing and Screening Inhibitors of Bacterial NAD Synthetase Enzyme,

TABLE 4B

Summary Of Mininium Lethal Concentration (MLC; µg/mL)

| Plate | Compound | A | B | C | D | E | F | G | H |
|---|---|---|---|---|---|---|---|---|---|
| 1 | 1108 | 4 | 2 | 4 | 8 | 4 | 4 | 2 | 2 |
| 2 | 1174 | 8 | 4 | 8 | 16 | 32 | 32 | 16 | 16 |
| 3 | 1072 | >32 | 16 | >32 | >32 | >32 | >32 | >32 | >32 |
| 4 | 1127 | >32 | >32 | >32 | >32 | >32 | >32 | >32 | >32 |
| 5 | 0270 | 2 | 2 | 8 | 8 | 1 | 2 | 2 | 2 |
| 6 | 1198 | 2 | 1 | 2 | 4 | 2 | 2 | 2 | 2 |
| 7 | 1264 | 1 | 1 | 2 | 2 | 1 | 2 | 4 | 4 |
| 8 | 1274 | >32 | 16 | >32 | >32 | >32 | >32 | >32 | >32 |
| 9 | 1308 | >32 | 8 | >32 | >32 | >32 | >32 | >32 | >32 |
| 10 | 0951 | 1 | 1 | 1 | 2 | 2 | 2 | 4 | 4 |
| 11 | 0409 | 1 | 0.5 | 1 | 1 | 2 | 2 | 2 | 2 |
| 12 | 1197 | 1 | 1 | 2 | 2 | 2 | 2 | 4 | 4 |

Compounds Thereof, and Methods of Treating Bacterial and Microbial Infections with Inhibitors of Bacterial NAD Synthetase Enzyme," International Patent Application No. PCT/US99/00810, International Filing Date Jan. 14, 1999.

What is claimed is:

1. A method of treating or preventing a fungal infection in a host comprising administering to a host a treatment or prevention effective amount of a yeast NAD synthetase enzyme inhibitor compound, wherein the prevention is used in a host in need of such treatment or a host susceptible to fungal infections.

2. The method of claim 1, wherein the compound administered has Structure 2:

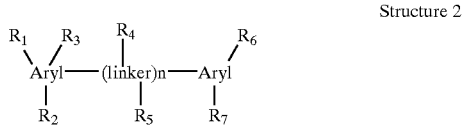

Structure 2 wherein n is an integer of from 1 to 12, $R_1$–$R_7$ each, independently, is H, an unsubstituted or a substituted cyclic or aliphatic group, or a branched or an unbranched group, and wherein the linker is a cyclic or aliphatic, branched or an unbranched alkyl, alkenyl, or an alkynyl group and wherein the linker may also contain one or more heteroatoms.

3. The method of claim 2, wherein n is from 5 to 9.

4. The method of claim 3, wherein the linker has the formula A—(C, Heteroatom)n—B.

5. The method of claim 3, wherein the linker is selected from the group consisting of A—(CH$_2$)n—B, A—(CH$_2$)n—O—C(=O)—B, A—O(CH$_2$)n—O—C(=O)—B, A—(CH$_2$)n—O—C(=O)CH$_2$—B, and A—O(CH$_2$)n—O—C(=O)CH$_2$—B.

6. The method of claim 5, wherein the linker is A—(CH$_2$)—O—(C=O)CH$_2$—B.

7. The method of claim 2, wherein the compound administered has Structure 4:

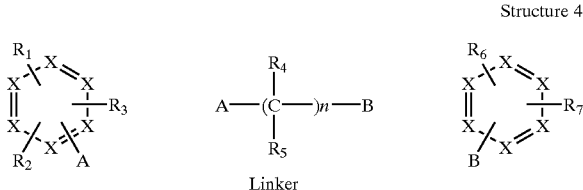

Structure 4 wherein X is a C, N, O or S within a monocyclic or bicyclic moiety, and A and B represent the respective sites of attachment for the linker, n is an integer of from 1 to 12, $R_1$–$R_7$ each, independently, is H, an unsubstituted or a substituted cyclic group, or an aliphatic group, or a branched or an unbranched group, and the linker is a saturated or unsaturated cyclic group or an aliphatic branched or unbranched alky, alkenyl or alkynyl group, and wherein the linker may also contain one or more heteroatoms.

8. The method of claim 2, wherein the compound administered has Structure 6:

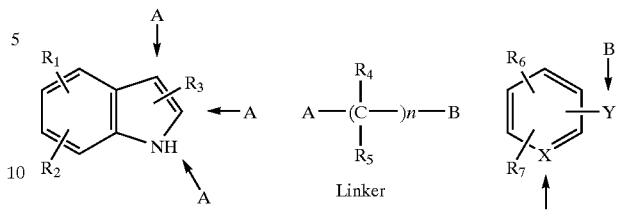

wherein X is C, N, O or S, Y is C, N, O, S, carboxy, ester, amide, or ketone, A and B represent the respective sites of attachment for a linker, n is an integer of from 1 to 12, and $R_1$–$R_7$ each, independently, is H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain one or more heteroatoms.

9. The method of claim 2, wherein the compound administered has Structure 7:

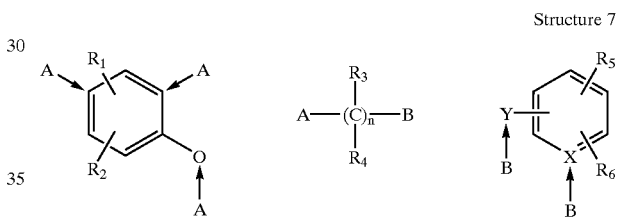

Structure 7 wherein X is C, N, O or S, Y is C, N, O, S, carboxy, ester, amide, or ketone, A and B represent the respective sites of attachment for a linker, n is an integer of from 1 to 12, and $R_1$–R6 each, independently, is H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain one or more heteroatoms.

10. The method of claim 2, wherein the compound administered has Structure 8:

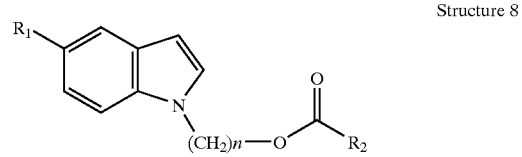

Structure 8 wherein n is an integer of from 1 to 12, $R_1$ is an H, methoxy, benzyloxy, or nitro and $R_2$ is 3-pyridyl, N-methyl-3-pyridyl, 3-quinolinyl, N-methyl-3-quinolinyl, 3-(dimethylamino) phenyl, 3-(trimethylammonio)phenyl, 4-(dimethylamino) phenyl, 4-(trimethylammonio)phenyl, 4-(dimethylaamino) phenylmethyl, or 4-(trimethylammonio)phenylmethyl.

11. The method of claim 2, wherein the compound administered has Structure 10:

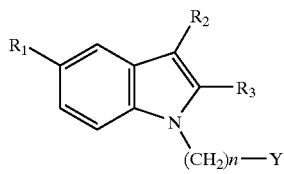

Structure 10 wherein n is an integer of from 1 to 12, $R_1$ is an H, $CO_2H$, —$OCH_3$, or —$OCH_2Ph$, $R_2$ is H, $CO_2H$, or CH=$CHCO_2H$, $R_3$ is H or $CO_2H$, and Y is N-linked pyridine-3-carboxylic acid, N-linked pyridine, N-linked quinoline, or N-linked isoquinoline.

12. The method of claim 2, wherein the compound administered has Structure 12:

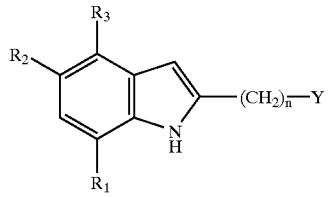

Structure 12 wherein n is an integer of from 1 to 12, $R_1$ is H, F, or $NO_2$, $R_2$ is H, $CH_3$, $CF_3$, $NO_2$, phenyl, n-butyl, isopropyl, F, phenyloxy, triphenylmethyl, methoxycarbonyl, methoxy, carboxy, acetyl, or benzoyl, $R_3$ is H or $CF_3$ and Y is N-linked pyridine-3-carboxylic acid, N-linked pyridine, N-linked quinoline, or N-linked isoquinoline.

13. The method of claim 2, wherein the compound administered has Structure 14:

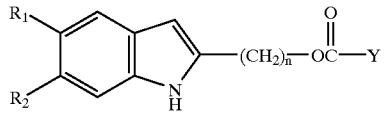

Structure 14 wherein n is an integer of from 1 to 12, $R_1$ is H, phenyloxy, isopropyl, acetyl, or benzoyl, $R_2$ is H or $CF_3$, and Y is 3-(dimethylamino)phenyl, 3-(trimelthylammonio)phenyl, 4-(dimethylamino)phenyl, 4-(trimethylammonio)phenyl, 2-(phenyl)phenyl, diphenylmethyl, 3-pyridyl, 4-pyridyl, or pyridine-3-methyl.

14. The method of claim 2, wherein the compound administered has Structure 100:

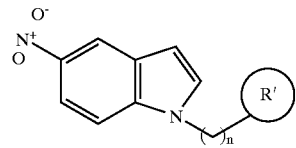

Structure 100 wherein R' is:

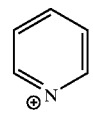

I

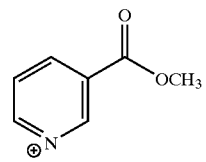

II

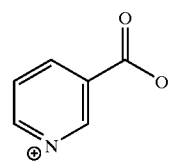

III

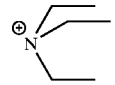

IV

V

VI

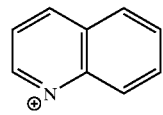

VII

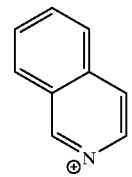

VIII

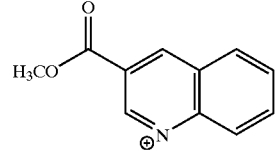

IX

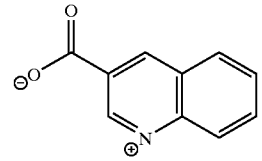

X wherein n is an integer of from 1 to 12.

15. The method of claim 2, wherein the compound administered has Structure 101:
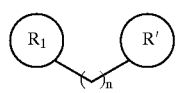
Structure 101
wherein R' is:
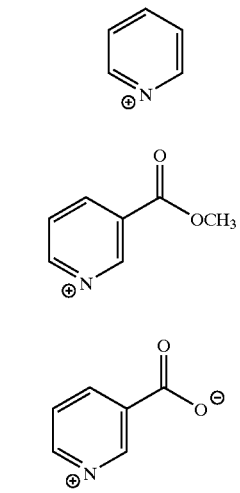
I
II
III
IV
V
VI
VII
VIII
IX
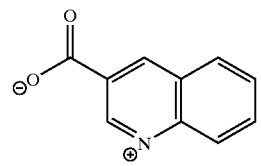
X
wherein $R_1$ is:
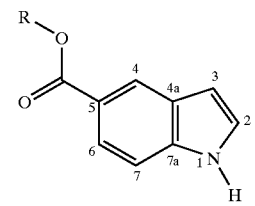
A
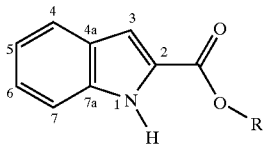
B
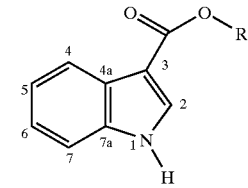
C
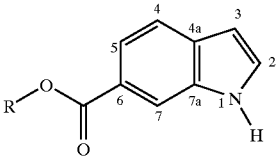
D
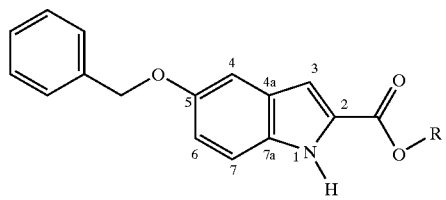
E
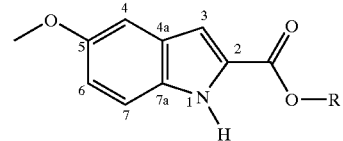
F
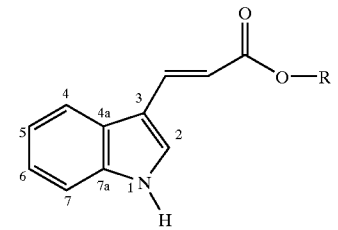
G wherein the R group in Fragments A–G is a benzyl group, a methyl group or a hydrogen.

16. The method of claim 2, wherein the compound administered has Structure 130:

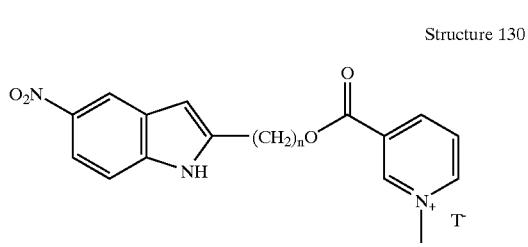

Structure 130 wherein n is an integer of from 1 to 12 and T⁻ is an anion.

17. The method of claim 2, wherein the compound administered has Structure 142:

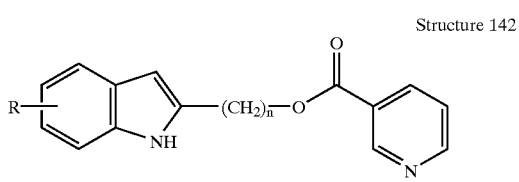

Structure 142 wherein n is an integer of from 1 to 12 and R is 6-CF₃, 5-OPh, 5-iPropyl, 5-COCH₃, or 5-COPh.

18. The method of claim 2, wherein the compound administered has Structure 144:

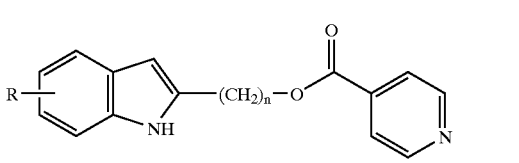

Structure 144 wherein n is an integer of from 1 to 12 and R is 6-CF₃, 5-OPh, 5-iPropyl, 5-COCH₃, or 5-COPh.

19. The method of claim 2, wherein the compound administered has Structure 146:

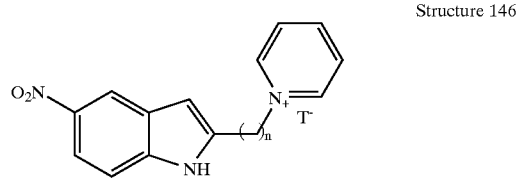

Structure 146 wherein n is an integer of from 1 to 12 and T⁻ is an anion.

20. The method of claim 2, wherein the compound administered has Structure 148:

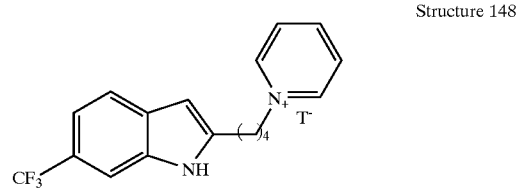

Structure 148 wherein n is an integer of from 1 to 12 and T⁻ is an anion.

21. The method of claim 2, wherein the compound administered has Structure 150:

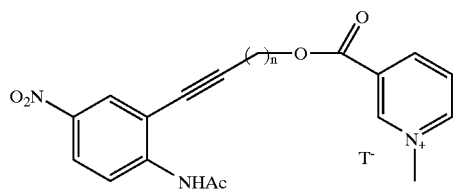

Structure 150 wherein n is an integer of from 1 to 12 and T⁻ is an anion.

22. The method of claim 2, wherein the compound administered has Structure 152:

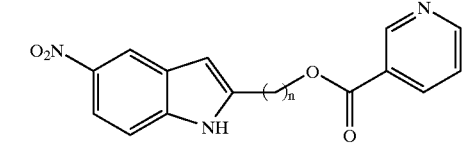

Structure 152 wherein n is an integer of from 1 to 12.

23. The method of claim 2, wherein the compound administered has Structure 154:

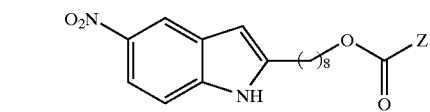

Structure 154 wherein Z is CH(diPh), 4-(N,N-dimethylamino)phenyl, CH₂CH₂-(3-pyridyl), or (2-phenyl)-phenyl.

24. The method of claim 2, wherein the compound administered has Structure 156:

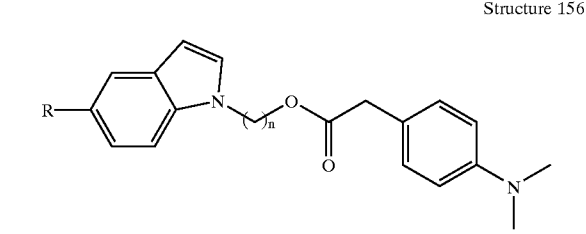

Structure 156 wherein n is an integer of from 1 to 12 and R is —OCH₃ or —OCH₂Ph.

25. The method of claim 2, wherein the compound administered has Structure 158:

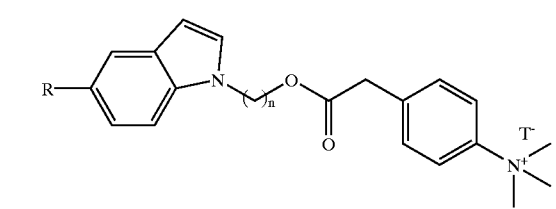

Structure 158 wherein n is an integer of from 1 to 12, R is —OCH₃ or —OCH₂Ph and T⁻ is an anion.

26. The method of claim 2, compound administered has Structure 160:

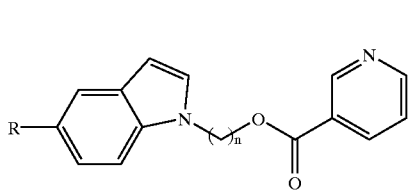

Structure 160 wherein n is an integer of from 1 to 12 and R is —OCH₃ or —OCH₂Ph.

27. The method of claim 2, wherein compound administered has Structure 162:

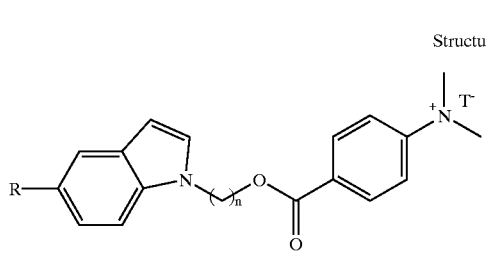

Structure 162 wherein n is an integer of from 1 to 12, R is —OCH₃ or —OCH₂Ph, and T⁻ is an anion.

28. The method of claim 2, wherein the compound administered has Structure 164:

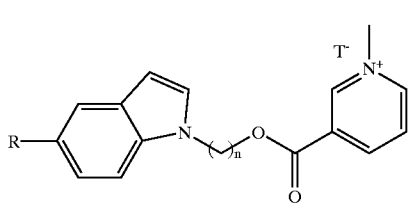

Structure 164 wherein n is an integer of from 1 to 12, R is —OCH₃ or —OCH₂Ph, and T⁻ is an anion.

29. The method of claim 2, wherein the compound has Structure 166:

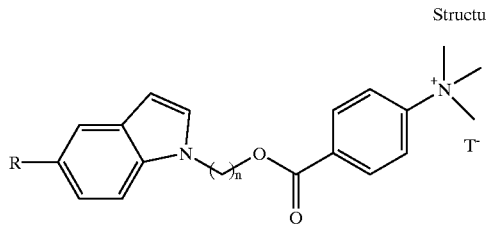

Structure 166 wherein n is an integer of from 1 to 12, R is —OCH₃ or —OCH₂Ph, and T⁻ is an anion.

30. The method of claim 2, wherein the compound administered has Structure 168:

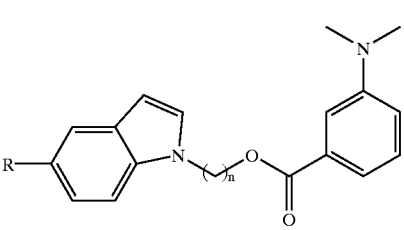

Structure 168 wherein n is an integer of from 1 to 12 and R is —OCH₃ or —OCH₂Ph.

31. The method of claim 2, wherein the compound administered has Structure 170:

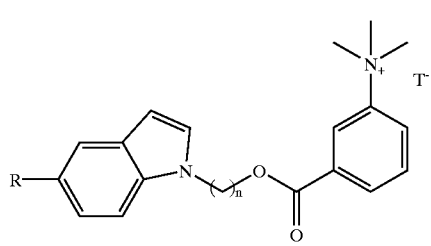

Structure 170 wherein n is an integer of from 1 to 12, R is —OCH₃ or —OCH₂Ph, and T⁻ is an anion.

32. The method of claim 2, wherein the compound administered has Structure 172:

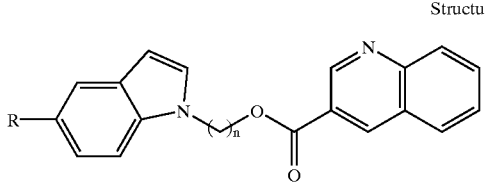

Structure 172 wherein n is an integer of from 1 to 12 and R is —OCH₃ or —OCH₂Ph.

33. The method of claim 2, wherein the compound administered has Structure 174:

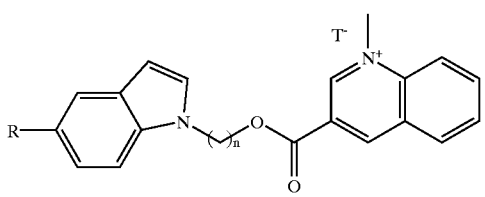

Structure 174 wherein n is an integer of from 1 to 12, R is —OCH₃ or —OCH₂Ph, and T⁻ is an anion.

34. The method of claim 2, wherein the compound administered has Structure 176:

Structure 176

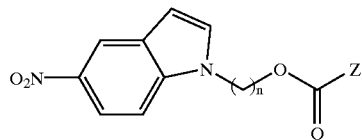

wherein n is an integer of from 1 to 12 and Z is 3-quinoline, 3-(N,N-dimethylamino)phenyl, or 4-(N,N-dimethylamino) phenyl.

35. The method of claim 2, wherein the compound administered has Structure 178:

Structure 178

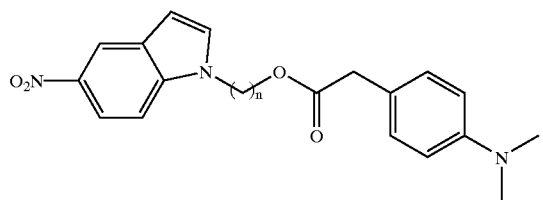

wherein n is an integer of from 1 to 12.

36. The method of claim 2, wherein the compound administered has Structure 180:

Structure 180

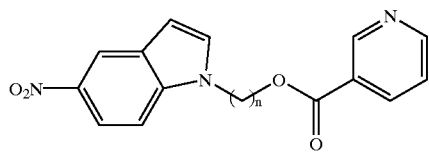

wherein n is an integer of from 1 to 12.

37. The method of claim 2, wherein the compound administered has Structure 182:

Structure 182

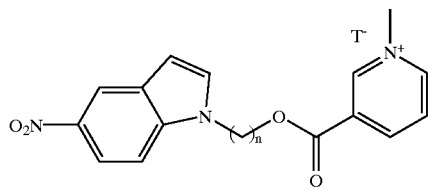

wherein n is an integer of from 1 to 12 and T⁻ is an anion.

38. The method of claim 2, wherein the compound administered has Structure 184:

Structure 184

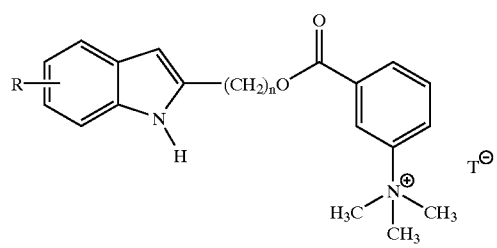

wherein n is an integer of from 1 to 12, R is 6-$CF_3$, 5-OPh, 5-$CH(CH_3)_2$, 5-$COCH_3$ or 5-COPh, and T⁻ is an anion.

39. The method of claim 2, wherein the compound administered has Structure 186:

Structure 186

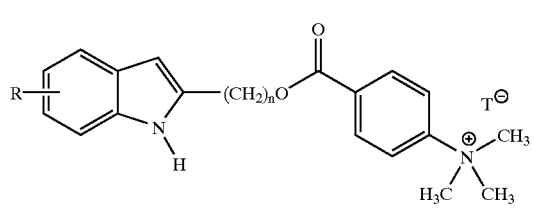

wherein n is an integer of from 1 to 12, R is 6-$CF_3$, 5-OPh, 5-$CH(CH_3)_2$, 5-$COCH_3$ or 5-COPh, and T⁻ is an anion.

40. The method of claim 2, wherein the compound administered has Structure 188:

Structure 188

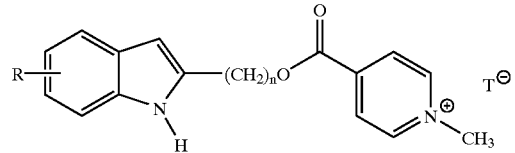

wherein n is an integer of from 1 to 12, R is 6-$CF_3$, 5-OPh, 5-$CH(CH_3)_2$, 5-$COCH_3$ or 5-COPh, and T⁻ is an anion.

41. The method of claim 2, wherein the compound administered has Structure 190:

Structure 190

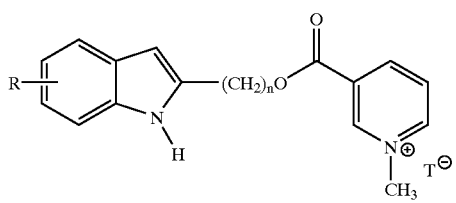

wherein n is an integer of from 1 to 12, R is 6-$CF_3$, 5-OPh, 5-$CH(CH_3)_2$, 5-$COCH_3$ or 5-COPh, and T⁻ is an anion.

42. The method of claim 2, wherein the compound administered has Structure 192:

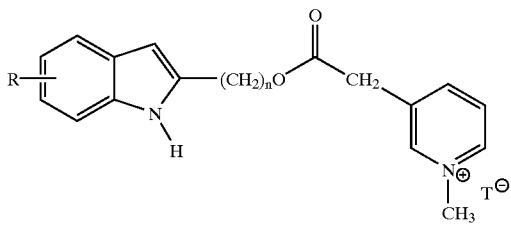

Structure 192 wherein n is an integer of from 1 to 12, R is 6-$CF_3$, 5-OPh, 5-$CH(CH_3)_2$, 5-$COCH_3$ or 5-COPh, and $T^-$ is an anion.

43. The method of claim 2, wherein the compound administered has Structure 194:

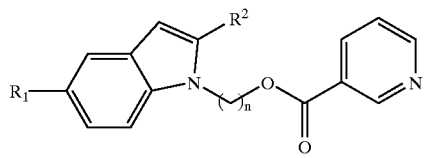

Structure 194 wherein n is an integer of from 1 to 12 and $R^1$ is H or —$OCH_2Ph$ and $R^2$ is H or $COOCH_3$.

44. The method of claim 2, wherein the compound administered has Structure 196:

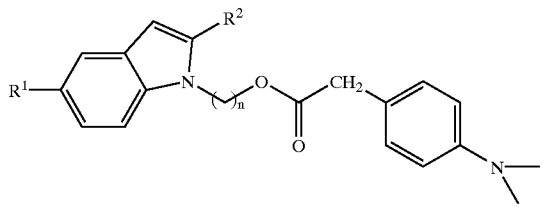

Structure 196 wherein n is an integer of from 1 to 12 and $R^1$ is H or —$OCH_2Ph$ and $R^2$ is H or $COOCH_3$.

45. The method of claim 2, wherein the compound administered has Structure 198:

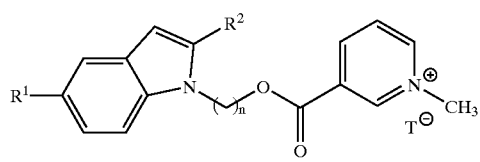

Structure 198 wherein n is an integer of from 1 to 12, $R^1$ is H, —$OCH_2Ph$, or $OCPh_3$, $R^2$ is H or $COOCH_3$, and $T^-$ is an anion.

46. The method of claim 2, wherein the compound administered has Structure 20:

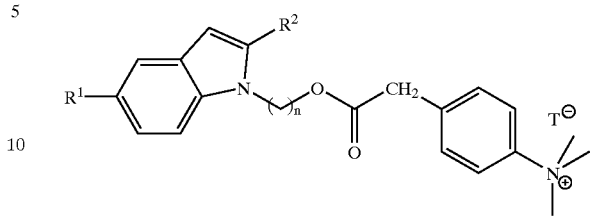

Structure 200 wherein n is an integer of from 1 to 12, $R^1$ is H or a —$OCH_2Ph$, $R^2$ is H or $COOCH_3$, and $T^-$ is an anion.

47. The method of claim 2, wherein the compound administered has Structure 202A:

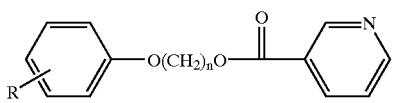

Structure 202A wherein n is an integer of from 1 to 12 and wherein R is H; 4-$NO_2$; 2-CONHPh; 2-$NO_2$; 4-[1'(4'-acetylpiperazine)]; 2-$COCH_3$; 3-$OCOCH_3$; 3-$OCH_3$; 4-$COCH_3$; 3-OCOPh; 2-$CONH_2$; 4-$CH=CHCOCH_3$; 4-OCOPh; 4-CH=CHCOPh; 4-{CO-3'[2'-butylbenzo(b)furan]}; 3-$NO_2$; 4-[5'-(5'-phenylhydantoin)]; 2-CH=CHCOPh; 2-$OCH_3$; 4-COPh; 4-$CONH_2$; 3-$COCH_3$; 4-OPh; 4-(N-phthalimide); 3-(N-morpholine); 2-(N-pyrrolidine); 2-(N-morpholine); or 4-$OCH_2Ph$.

48. The method of claim 2, wherein the compound administered has Structure 204A:

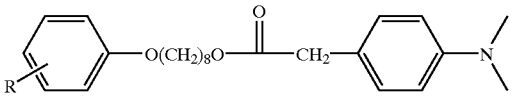

Structure 204A wherein n is an integer of from 1 to 12 and wherein R is H; 4-$NO_2$; 2-CONHPh; 2-$NO_2$; 4-[1'(4'-acetylpiperazine)]; 2-$COCH_3$; 3-$OCOCH_3$; 3-$OCH_3$; 4-$COCH_3$; 3-OCOPh; 2-$CONH_2$; 4-$CH=CHCOCH_3$; 4-OCOPh; 4-CH=CHCOPh; 4-{CO-3'[2'-butylbenzo(b)furan]}; 3-$NO_2$; 4-[5'-(5'-phenylhydantoin)]; 2-CH=CHCOPh; 2-$OCH_3$; 4-COPh; 4-$CONH_2$; 3-$COCH_3$; 4-OPh; 4-(N-phthalimide); 3-(N-morpholine); 2-(N-pyrrolidine); 2-(N-morpholine); or 4-$OCH_2Ph$.

49. The method of claim 2, wherein the compound administered has Structure 206:

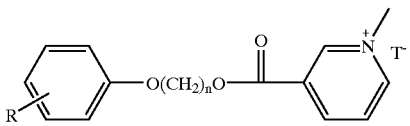

Structure 206 wherein n is an integer of from 1 to 12, R is H; 4-$NO_2$; 2-CONHPh; 2-$NO_2$; 2-$COCH_3$; 3-$OCH_3$; 4-$COCH_3$; 3-OCOPh; 2-$CONH_2$; 4-CH=CHCOCH$_3$; 4-OCOPh; 4-CH=CHCOPh; 4-{CO-3'[2'-butylbenzo(b)furan]};

3-NO$_2$; 2-CH=CHCOPh; 2-OCH$_3$; 4-COPh; 3-COCH$_3$; 4-OPh; 4-(N-phthalimide); or 4-OCH$_2$Ph, and T$^-$ is an anion.

50. The method of claim 2, wherein the compound administered has Structure 208:

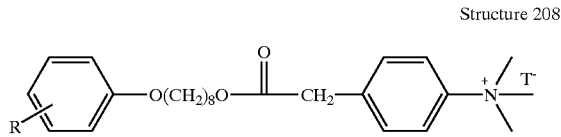

Structure 208 wherein R is 4-NO$_2$; 2-CONHPh; 2-NO$_2$; 2-COCH$_3$; 3-OCH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 2-CH=CHCOPh; 2-OCH$_3$; 4-COPh; 3-COCH$_3$; 4-OPh; 4-(N-phthalimide); 3-(N-morpholine); 2-(N-morpholine); or 4-OCH$_2$Ph; and T$^-$ is an anion.

51. The method of claim 2, wherein the compound administered has Structure 210:

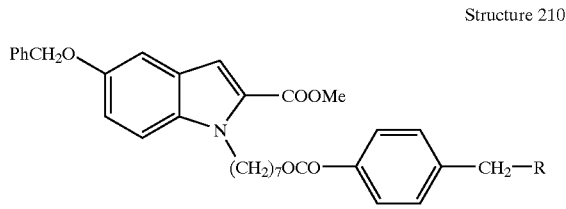

Structure 210 wherein R is NH$_2$; NMe$_2$; NMe$_3$.I; NH$_2$.HCl; NMe$_2$ or HCl.

52. The method of claim 2, wherein the compound administered has Structure 212:

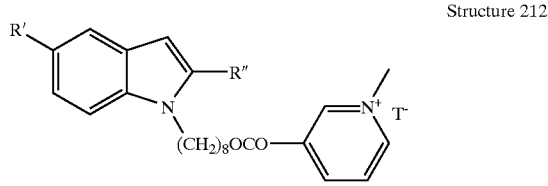

Structure 212 wherein R' is PhCONH or Ph$_3$C, R" is H or COOCH$_3$, and T$^-$ is an anion.

53. The method of claim 2, wherein the compound administered has Structure 214:

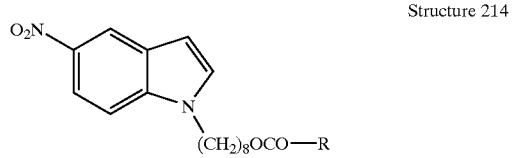

Structure 214 wherein R is 4-hydroxyphenyl or 3-hydroxy-4-methylphenyl.

54. The method of claim 2, wherein the compound administered has Structure 216:

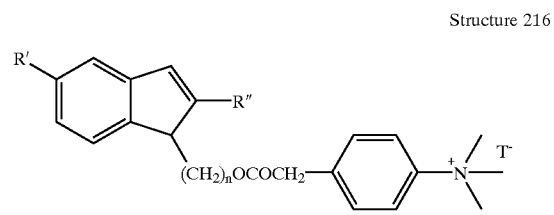

Structure 216 wherein R' is PhCONH, R" is H or COOCH$_3$, n is an integer of from 7 to 8, and T$^-$ is an anion.

55. The method of claim 2, wherein the host is a plant.

56. The method of claim 2, wherein the compound administered has little or no inhibitory effect on the NAD synthetase enzyme of the host.

57. The method of claim 2, comprising oral, rectal, intramuscularly, intravenous, intravesicular or topical administration.

58. The method of claim 2, wherein the compound is administered in a dosage of between about 0.1 to about 15 g per day and wherein the dosage is administered from about 1 to about 4 times per day.

59. The method of claim 2, wherein the compound administered has Structure 300:

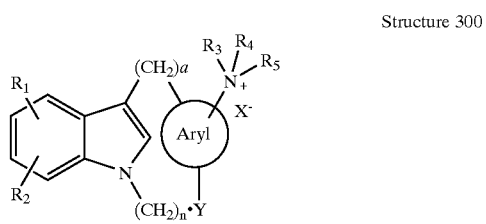

Structure 300 wherein Y is C, N, O, S, ester, amide, or ketone, n is an integer of from 1 to 12, a is an integer from 1–3, and R$_1$–R$_5$ each, independently, is H, unsubstituted or substituted cyclic group or an aliphatic group, a branched or an unbranched group, or an alky, alkenyl, or alkynyl, or an aryl group while R$_1$–R$_2$ may also be H, hydroxyl, ketone, nitro, amino, amidino, guanidino, carboxylate, amide, ester, sulfonate, halogen, alkoxy, or aryloxy group, and the (CH$_2$)$_n$ linker may be saturated or unsaturated and contain cyclic or aliphatic group, branched or unbranched alkyl, alkenyl, or alkynyl substituent, and further wherein the linker may also contain one or more heteroatoms while the aryl group is an aromatic grouping which may contain one or more rings, and X$^-$ is an anion.

60. The method of claim 2, wherein the compound administered has Structure 1300:

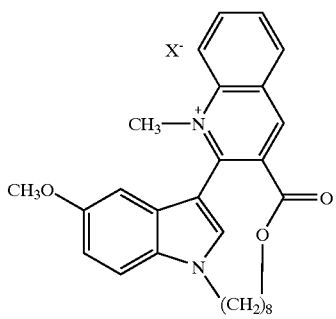

Structure 1300 wherein X⁻ is an anion.

61. The method of claim 2, the compound administered has Structure 400:

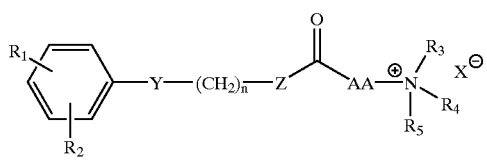

Structure 400 wherein Y is C, N, O, S, ester, amide, or ketone; Z is C, N, O, or S; AA is a natural or unnatural stereoisomer of an α-, β-, γ-, or δ-amino acid in which the carboxyl carbonyl is attached to Z, and the amino grouping may be a primary, secondary, tertiary, or quaternary ammonium compound; n is an integer of from 1 to 12; and $R_1-R_5$ each, independently, is H, unsubstituted or substituted cyclic group or an aliphatic group, a branched or an unbranched group, or an alkyl, alkenyl, or alkynyl, or an aryl group wherein $R_1-R_2$ may also be H, hydroxyl, ketone, nitro, amino, amidino, guanidino, carboxylate, amide, ester, sulfonate, halogen, alkoxy, or aryloxy group and the $(CH_2)_n$ linker may be saturated or unsaturated and contain cyclic or aliphatic group, branched or unbranched alkyl, alkenyl, or alkynyl substituents, and further wherein the linker may also contain one or more heteroatoms, and X⁻ is an anion.

62. The method of claim 2, wherein the compound administered has Structure 1230:

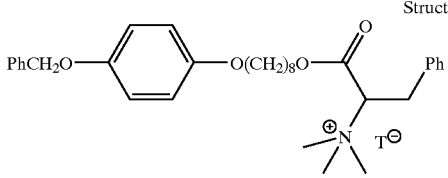

Structure 1230 wherein I⁻ is an anion.

63. The method of claim 2, wherein the compound administered has Structure 1260:

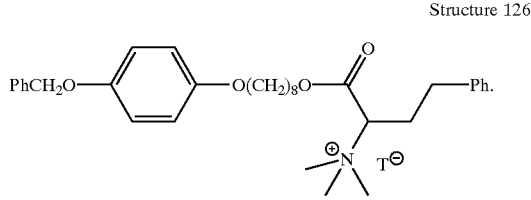

Structure 1260

64. The method of claim 46, wherein n is 7, $R^1$ is —OCH₂Ph and $R^2$ is —COOCH₃.

65. The method of claim 5, wherein the compound administered has one of the following structures:

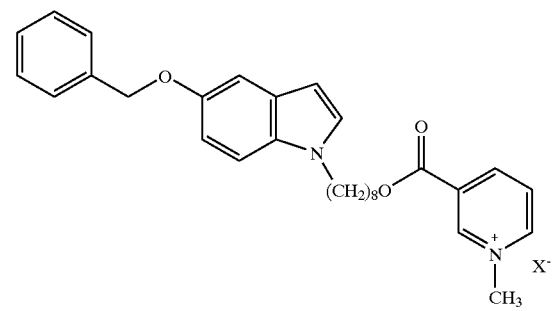

769

749

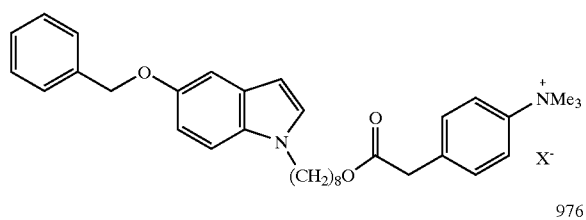

976

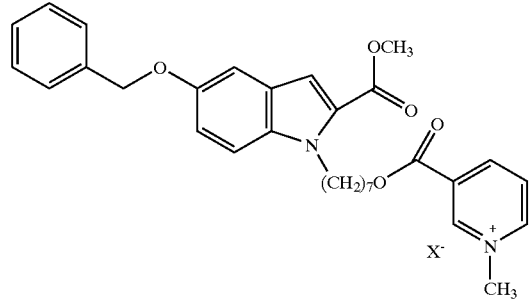

230

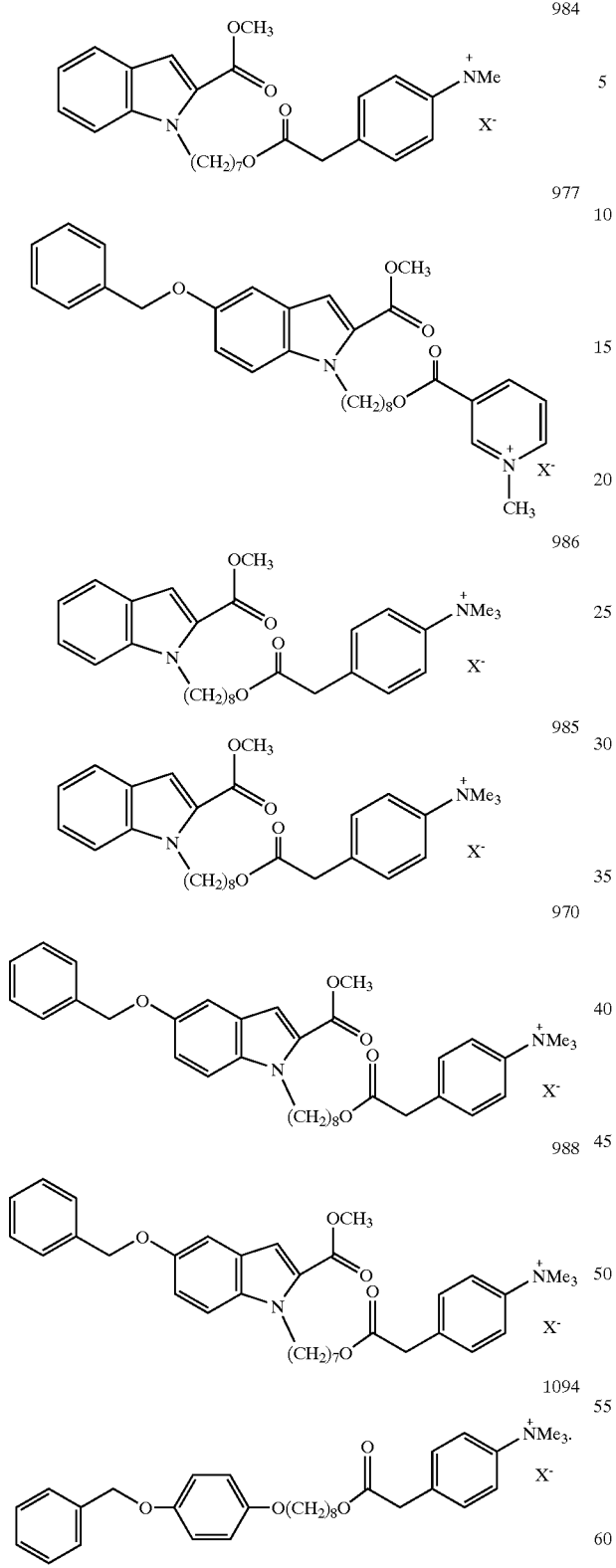
66. The method of claim 5, wherein the compound administered has one of the following structures, wherein X⁻ is an anion:

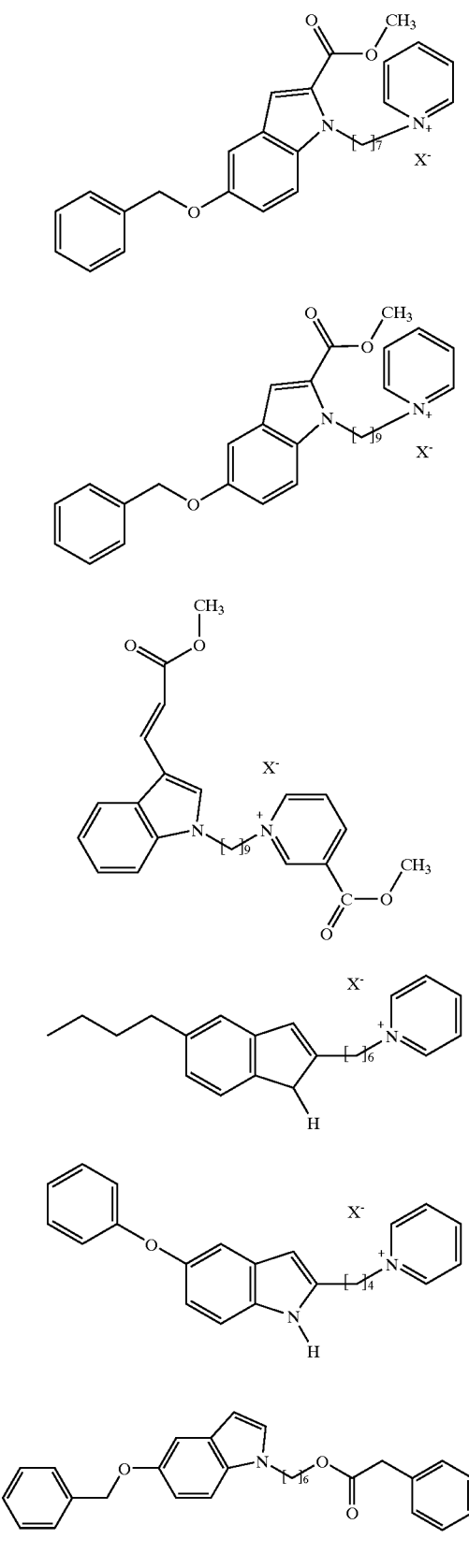

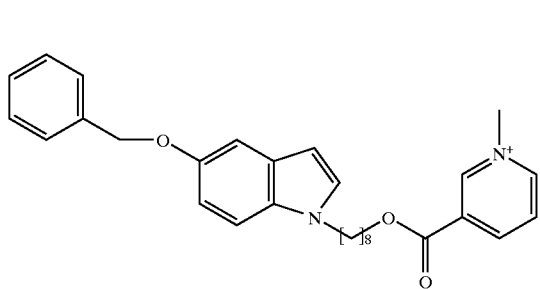
769
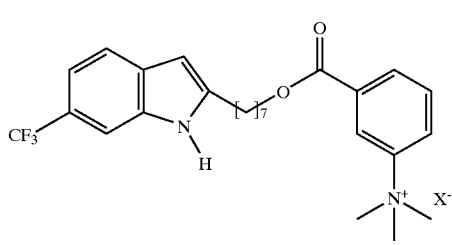
869
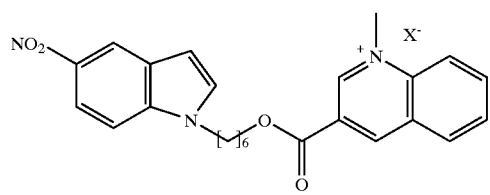
832
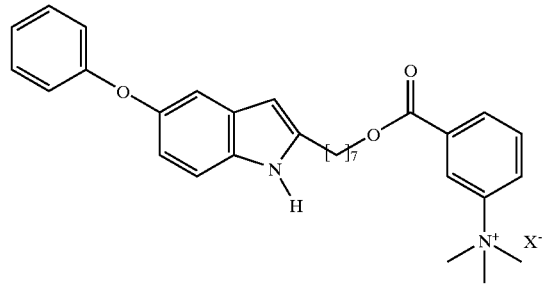
872
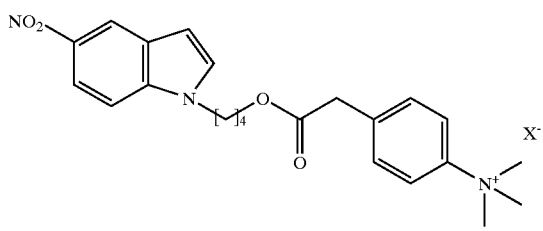
848
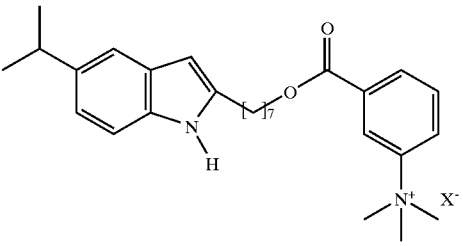
875
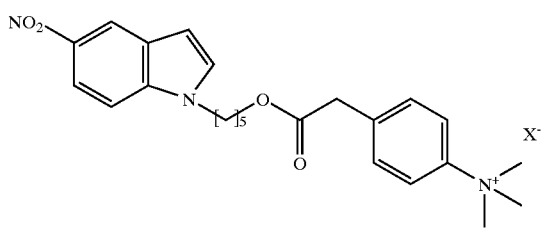
849
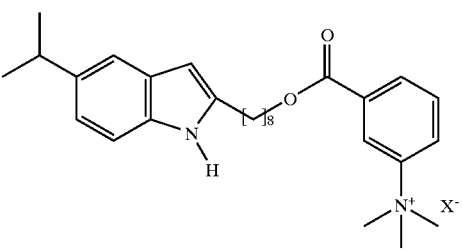
876
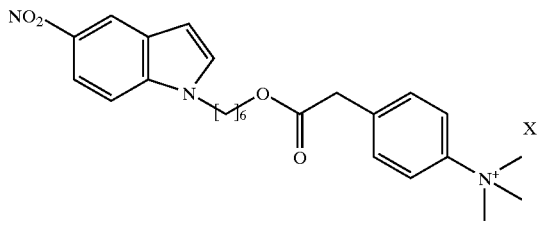
850
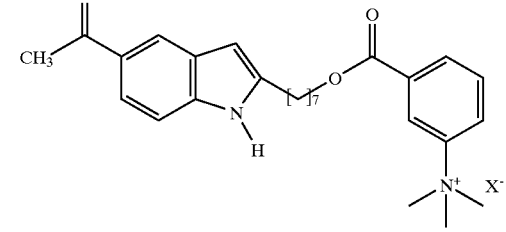
878
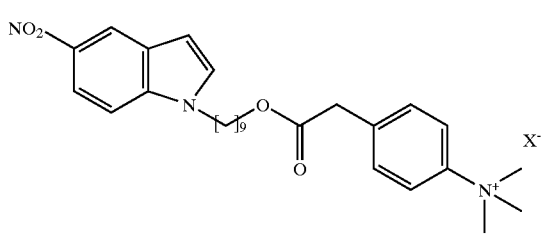
853
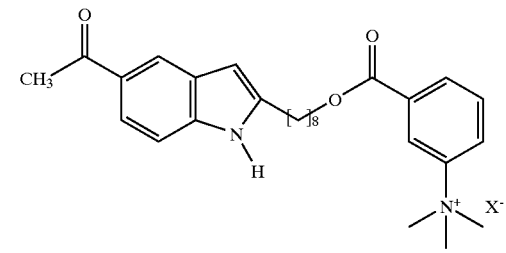
879

882
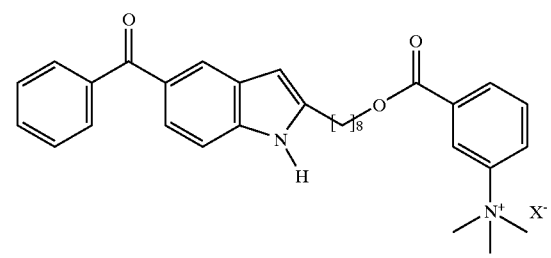
884
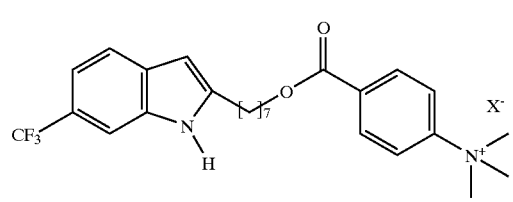
886
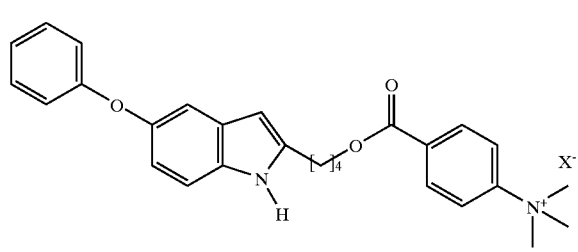
887
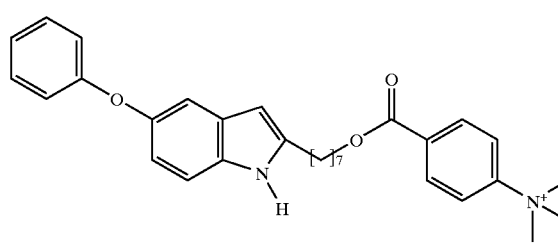
889
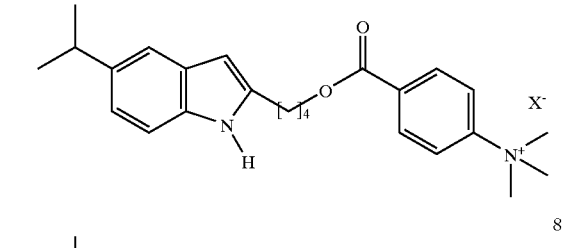
891
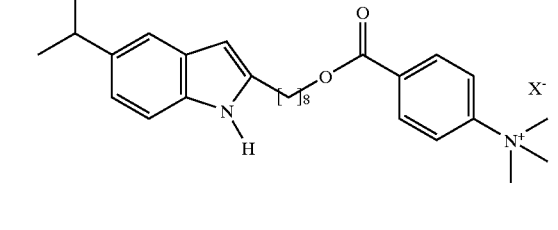
894
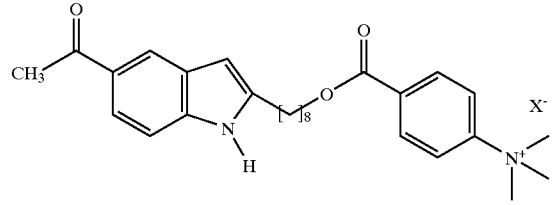
906
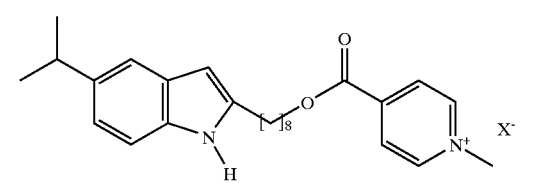
909
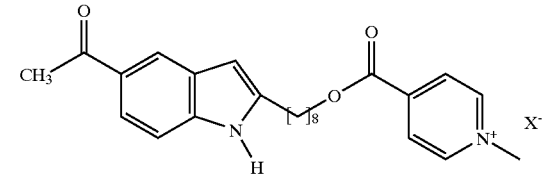
917
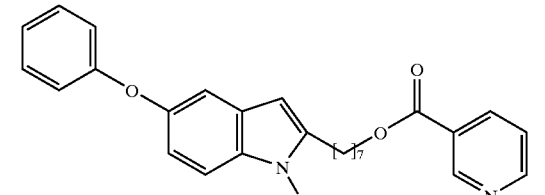
921
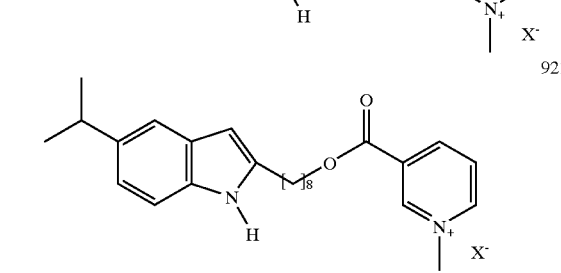
924
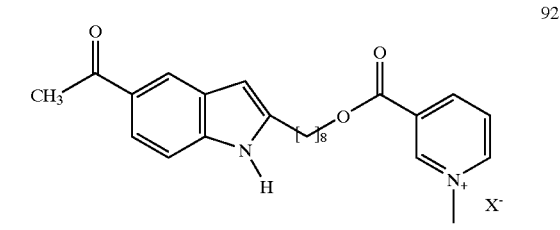
936
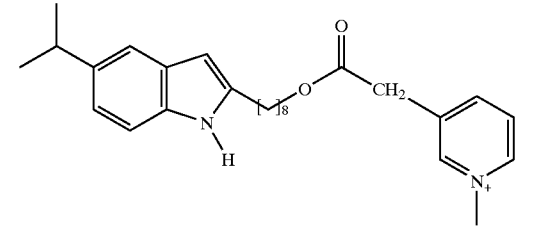

-continued
985
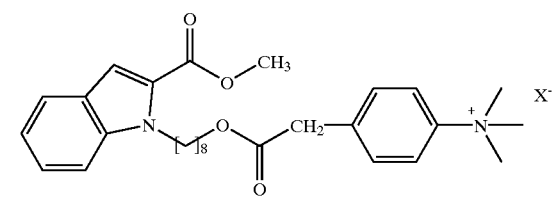
986
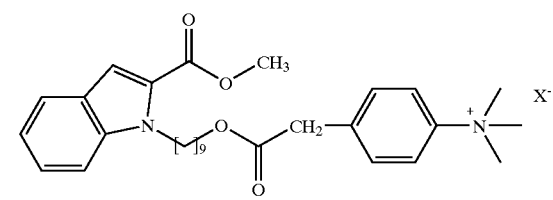
988
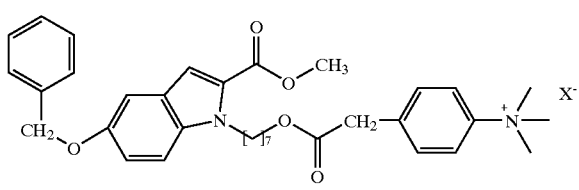
990
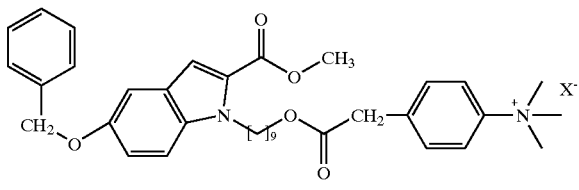
1059
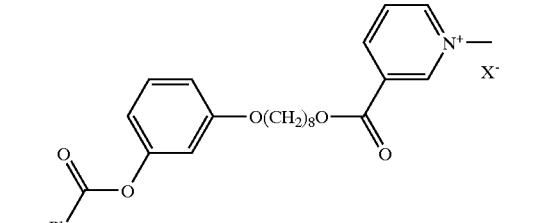
1064
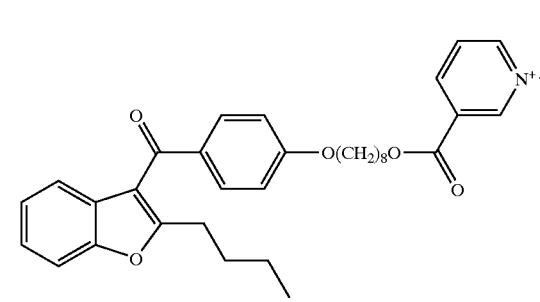
1066
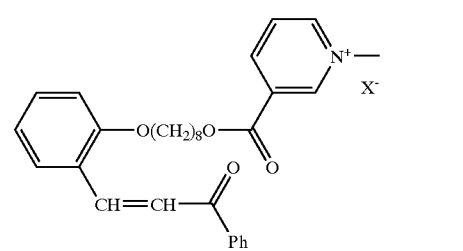
-continued
1068
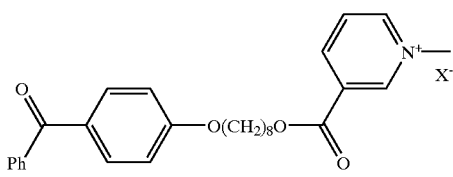
1070
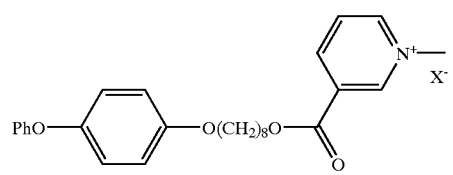
1072
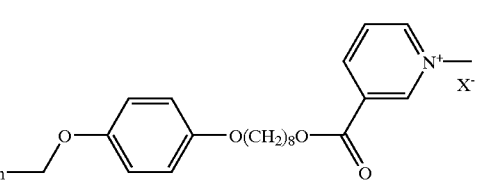
1074
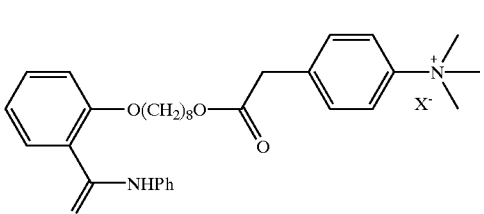
1075
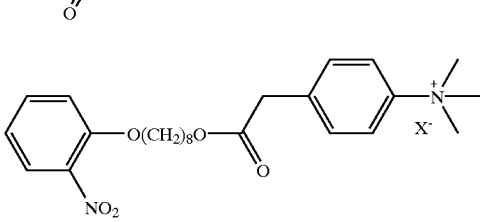
1079
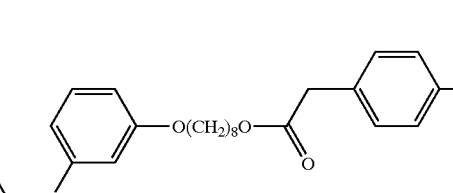
1080
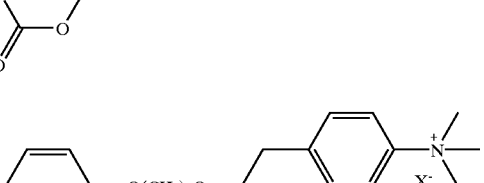
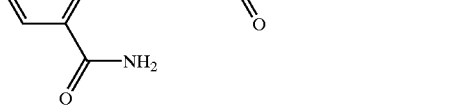
1082
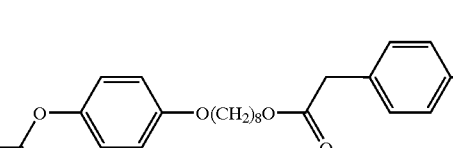

-continued
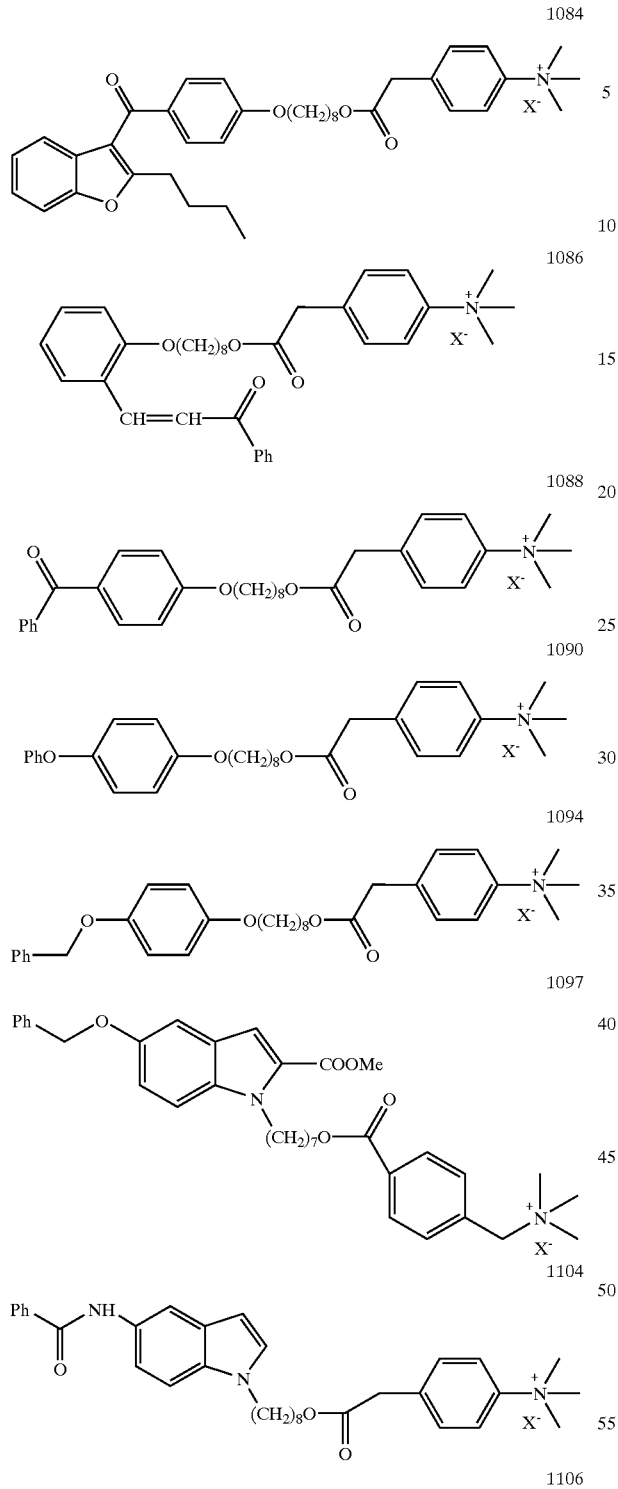
-continued
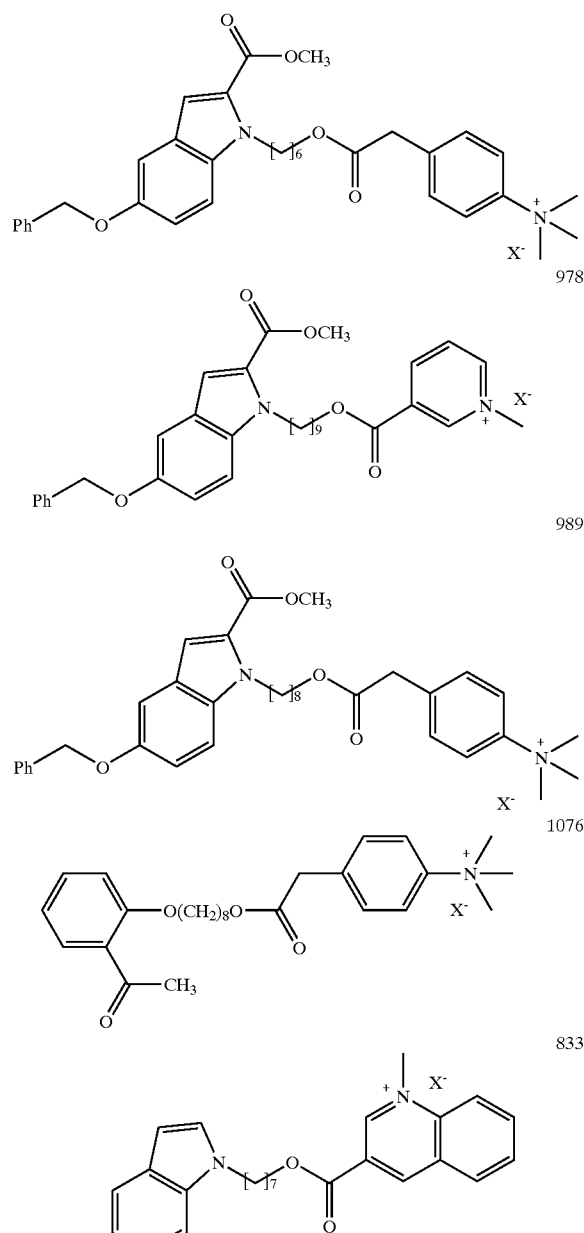
wherein X⁻=F⁻, Cl⁻, Br⁻, I⁻, acetate, or any pharmaceutically acceptable anion.
67. The method of claims 2, wherein the compound administered has Structure 132:
Structure 132
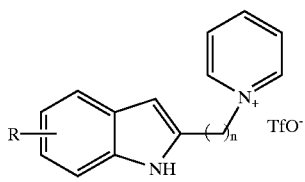
wherein n is an integer of from 1 to 12 and R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-Oph, 5-COPh, 5-CF$_3$, 5-COCH$_3$, 5-OCH$_3$, 5-COOCH$_3$ or 5-COOH.

68. The method of claim 2, wherein the compound administered has Structure 134:

Structure 134

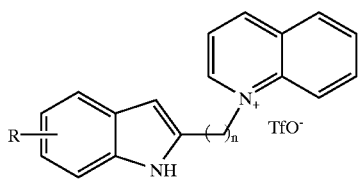

wherein n is an integer of from 1 to 12 and R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-Oph, 5-COPh, 5-CF$_3$, 5-COCH$_3$, 5-OCH$_3$, 5-COOCH$_3$, or 5-COOH.

69. The method of claim 2, wherein the compound administered has Structure 136:

Structure 136

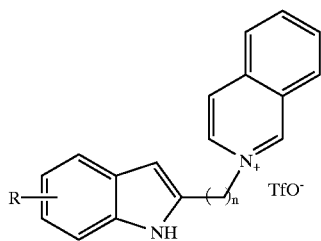

wherein n is an integer of from 1 to 12 and R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-Oph, 5-COPh, 5-CF$_3$, 5-COCH$_3$, 5-OCH$_3$, 5-COOCH$_3$, or 5-COOH.

70. The method of claim 2, wherein the compound administered has Structure 138:

Structure 138

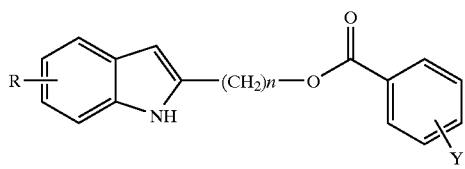

wherein n is an integer of from 1 to 12 and R is 5-CF$_3$, 5-Oph, 5-iPropyl, 5-COCH$_3$, or 5-COPh and Y is 3-N,N-dimethylamino(phenyl), 4-N,N-dimethylamino(phenyl), or 2-Ph.

71. The method of claim 2, wherein the compound administered has Structure 140:

Structure 140

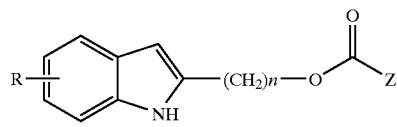

wherein n is an integer of from 1 to 12, R is 5-CF$_3$, 5-OPh, 5-iPropyl, 5-COCH$_3$ or 5-COPh, and Z is CH(Ph)$_2$ or 3-Pyridyl.

72. A method of killing an yeast or decreasing the growth of an yeast, comprising contacting the yeast with an amount of a yeast NAD synthetase enzyme inhibitor effective to reduce or eliminate the production of NAD whereby the yeast is killed or the yeast growth is decreased.

73. The method of claim 72, wherein the NAD synthetase enzyme inhibitor is a compound that selectively binds with one or more catalytic sites on a yeast NAD synthetase enzyme.

74. The method of claim 73, wherein the yeast NAD synthetase enzyme inhibitor has Structure 2:

Structure 2

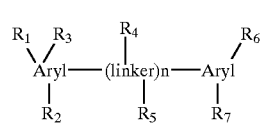

wherein n is an integer of from 1 to 12, R$_1$–R$_7$ each, independently, is H, an unsubstituted or a substituted cyclic or aliphatic group, or a branched or an unbranched group, and wherein the linker is a cyclic or aliphatic, branched or an unbranched alkyl, alkenyl, or an alkynyl group and wherein the linker may also contain one or more heteroatoms.

75. The method of claim 74, wherein n is from 5 to 9.

76. The method of claim 75, wherein the linker has the formula A—(C, Heteroatom)$_n$—B.

77. The method of claim 75, wherein the linker is selected from the group consisting of A—(CH$_2$)n—B, A—(CH$_2$)n—O—C(=O)—B, A—O(CH$_2$)n—O—C(=O)—B, A—(CH$_2$)n—O—C(=O)CH$_2$—B, and A—O(CH$_2$)n—O—C(=O)CH$_2$—B.

78. The method of claim 77, wherein the linker is A—(CH$_2$)—O—(C=O)CH$_2$—B.

79. The method of claim 74, wherein the yeast NAD synthetase enzyme inhibitor has Structure 4:

Structure 4

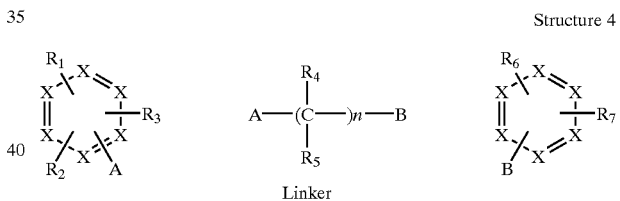

Linker wherein X is a C, N, O or S within a monocyclic or bicyclic moiety, and A and B represent the respective sites of attachment for the linker, n is an integer of from 1 to 12, R$_1$–R$_7$ each, independently, is H, an unsubstituted or a substituted cyclic group, or an aliphatic group, or a branched or an unbranched group, and the linker is a saturated or unsaturated cyclic group or an aliphatic branched or unbranched alkyl, alkenyl or alkynyl group, and wherein the linker may also contain one or more heteroatoms.

80. The method of claim 74, wherein the yeast NAD synthetase enzyme inhibitor has Structure 6:

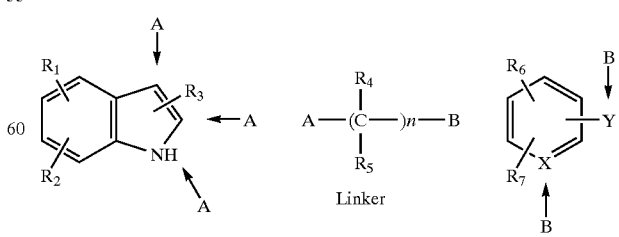

Linker wherein X is C, N, O or S, Y is C, N, O, S, carboxy, ester, amide, or ketone, A and B represent the respective sites of attachment for a linker, n is an integer of from 1 to 12, and $R_1$–$R_7$ each, independently, is H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain one or more heteroatoms.

81. The method of claim 73, wherein the yeast NAD synthetase enzyme inhibitor has Structure 200:

Structure 200

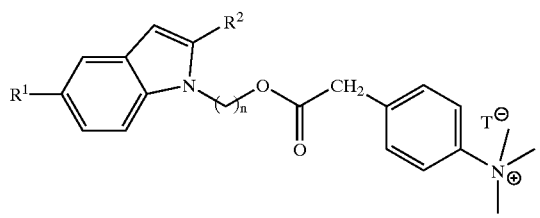

wherein n is an integer of from 1 to 12, $R^1$ is H or a —$OCH_2Ph$, $R^2$ is H or $COOCH_3$, and $T^-$ is an anion.

82. The method of claim 74, wherein the yeast NAD synthetase enzyme inhibitor has Structure 216:

Structure 216

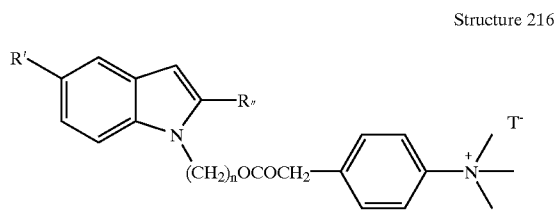

wherein R' is PhCONH, R" is H or $COOCH_3$, n is an integer of from 7 to 8, and $T^-$ is an anion.

83. The method of claim 81, wherein n is 7, $R^1$ is —$OCH_2Ph$ and $R^2$ is —$COOCH_3$.

84. The method of claim 74, wherein the yeast NAD synthetase enzyme inhibitor has one of the following structures wherein $X^-$ is an anion:

769

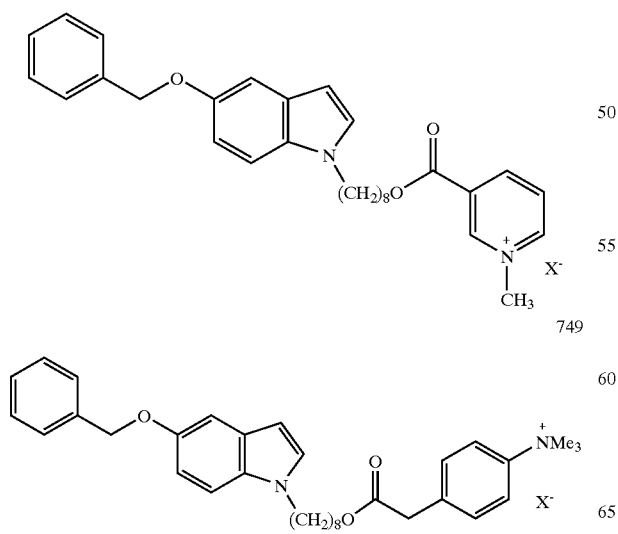

749

976

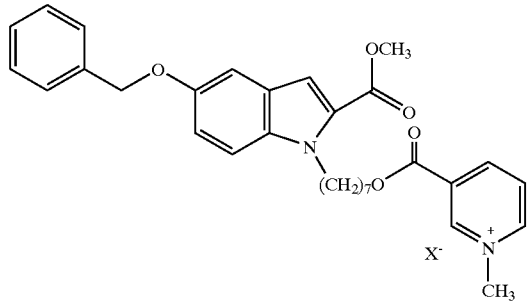

230

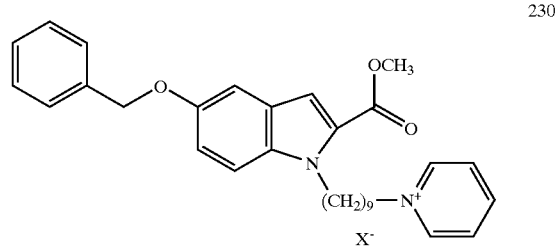

984

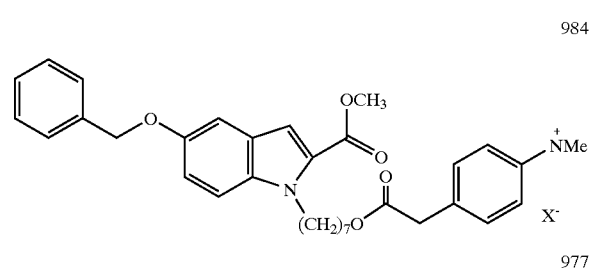

977

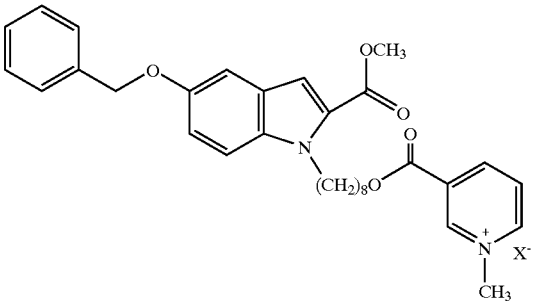

986

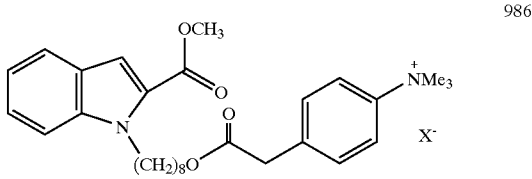

985

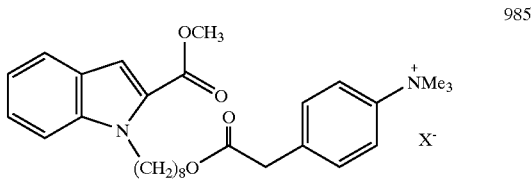

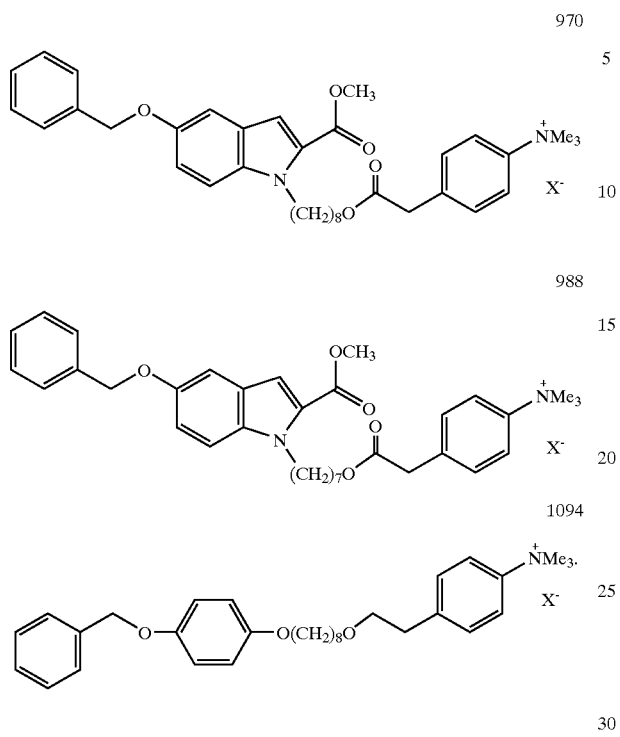
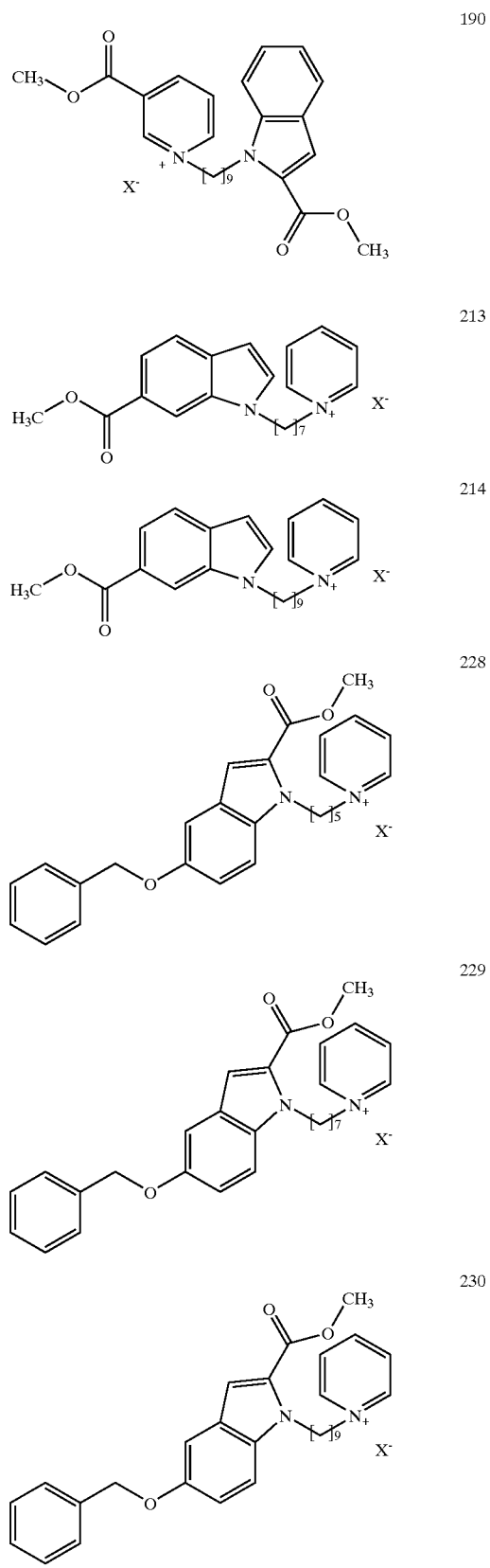
85. The method of claim 74, wherein the yeast NAD synthetase enzyme inhibitor has one of the following structures, wherein X⁻ is an anion:
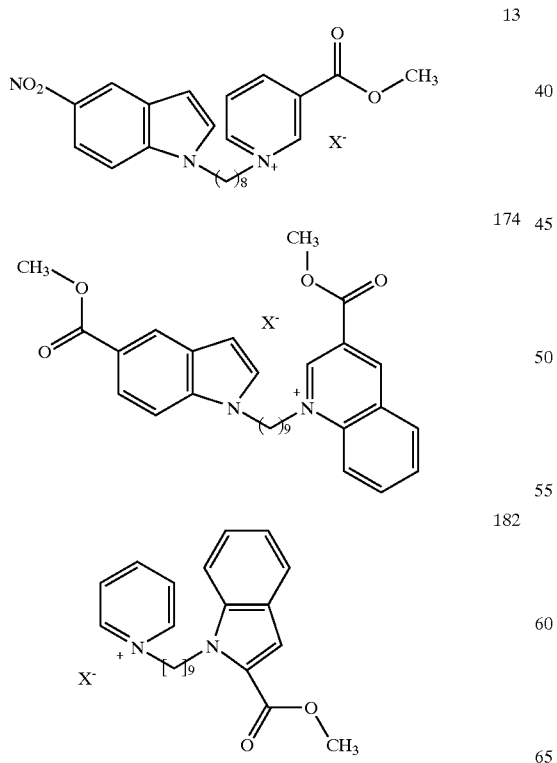

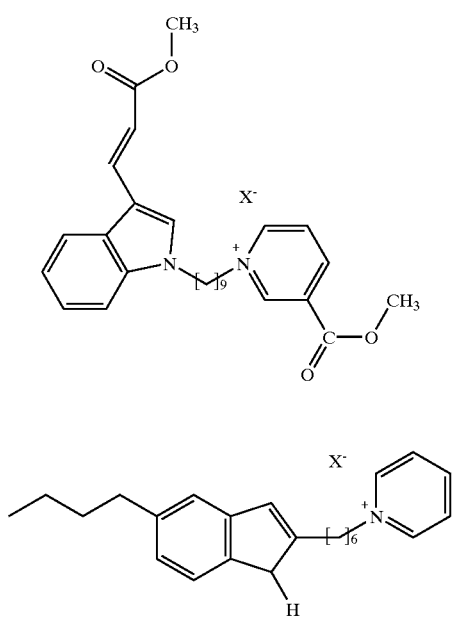
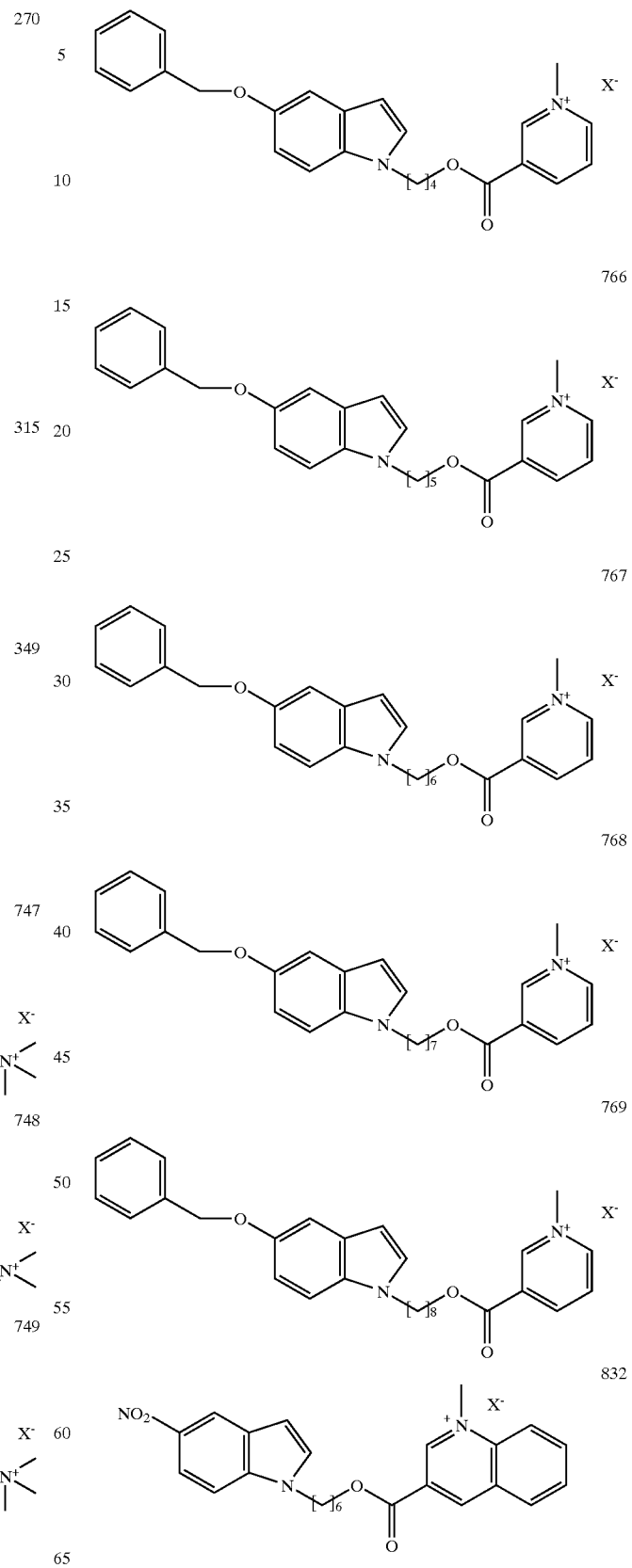

-continued

886
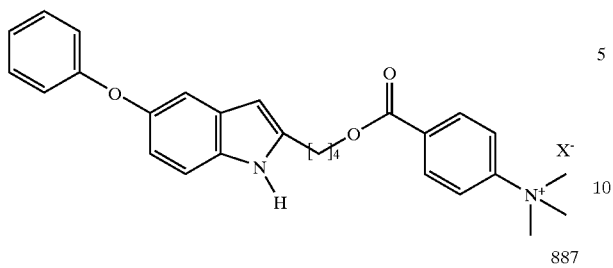
887
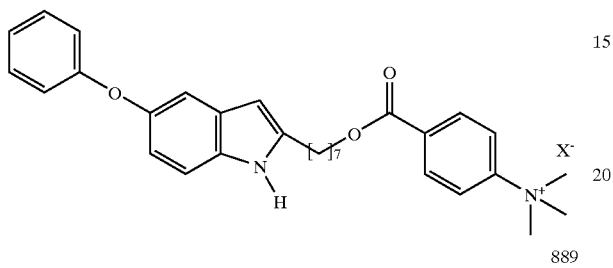
889
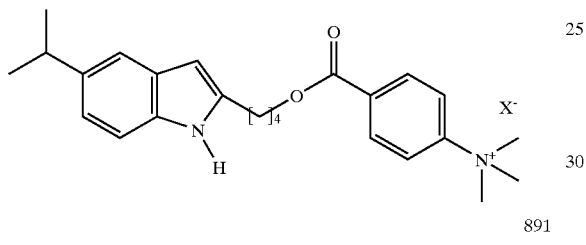
891
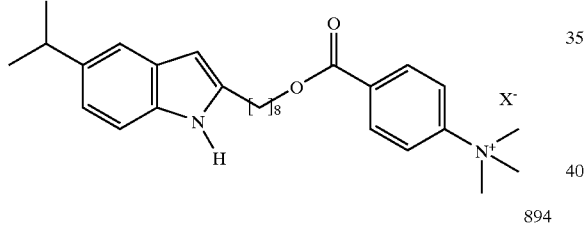
894
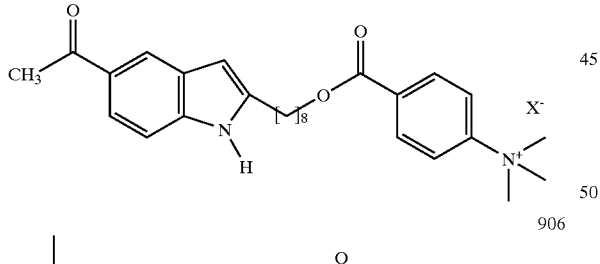
906
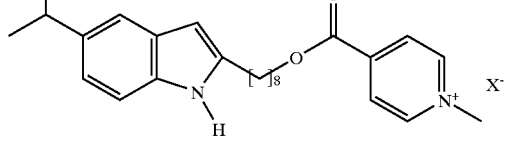
909
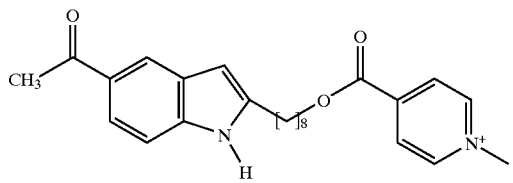
917
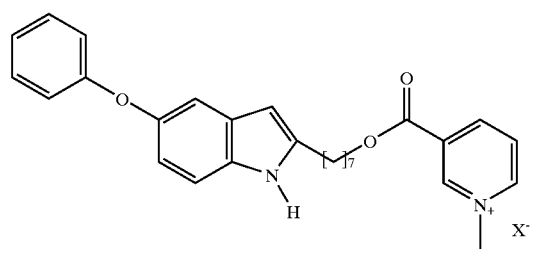
921
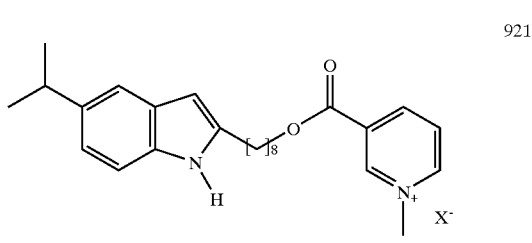
924
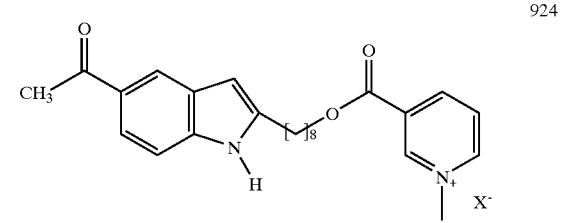
936
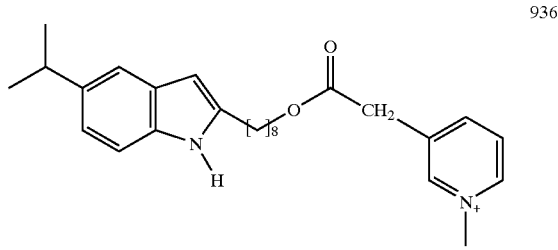
939
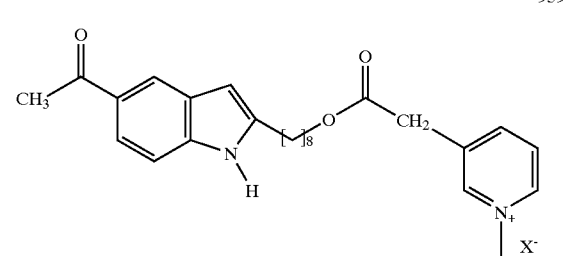
941
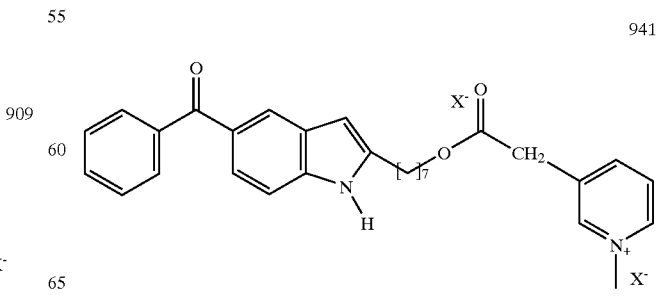

942
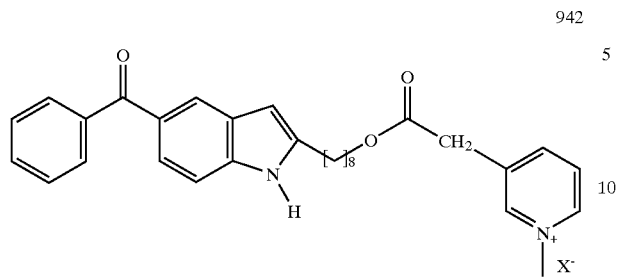
977
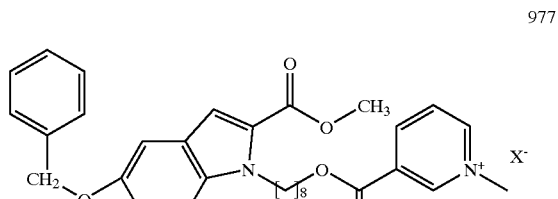
970
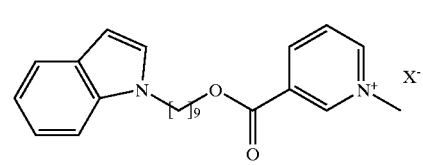
981
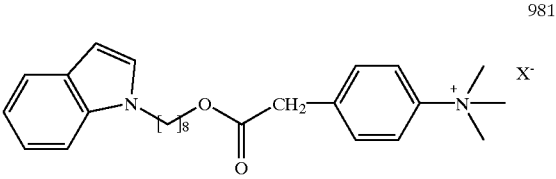
972
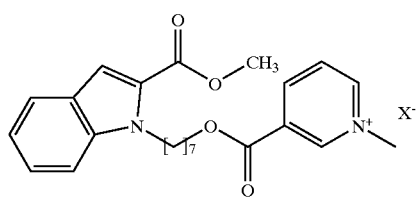
982
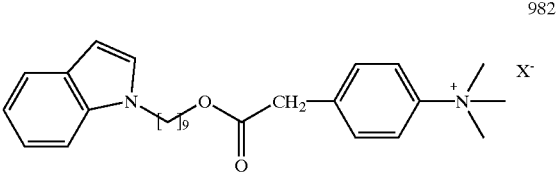
973
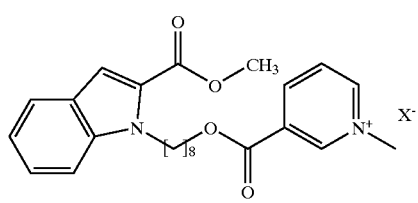
983
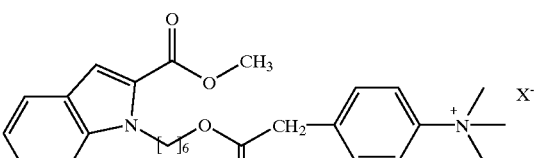
974
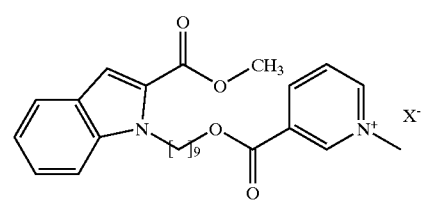
984
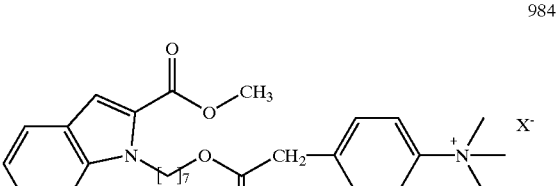
975
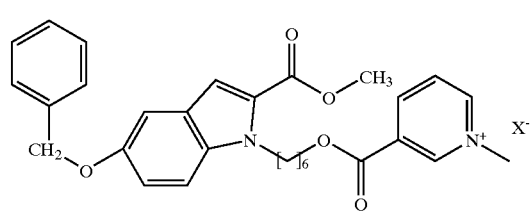
985
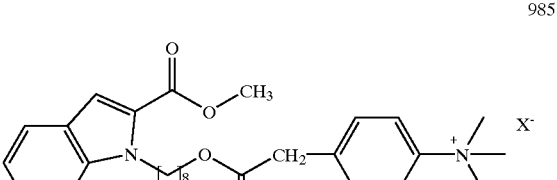
976
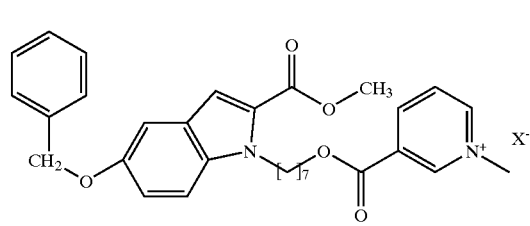
986
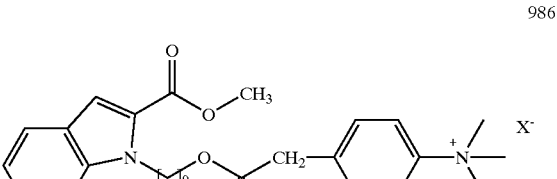

-continued

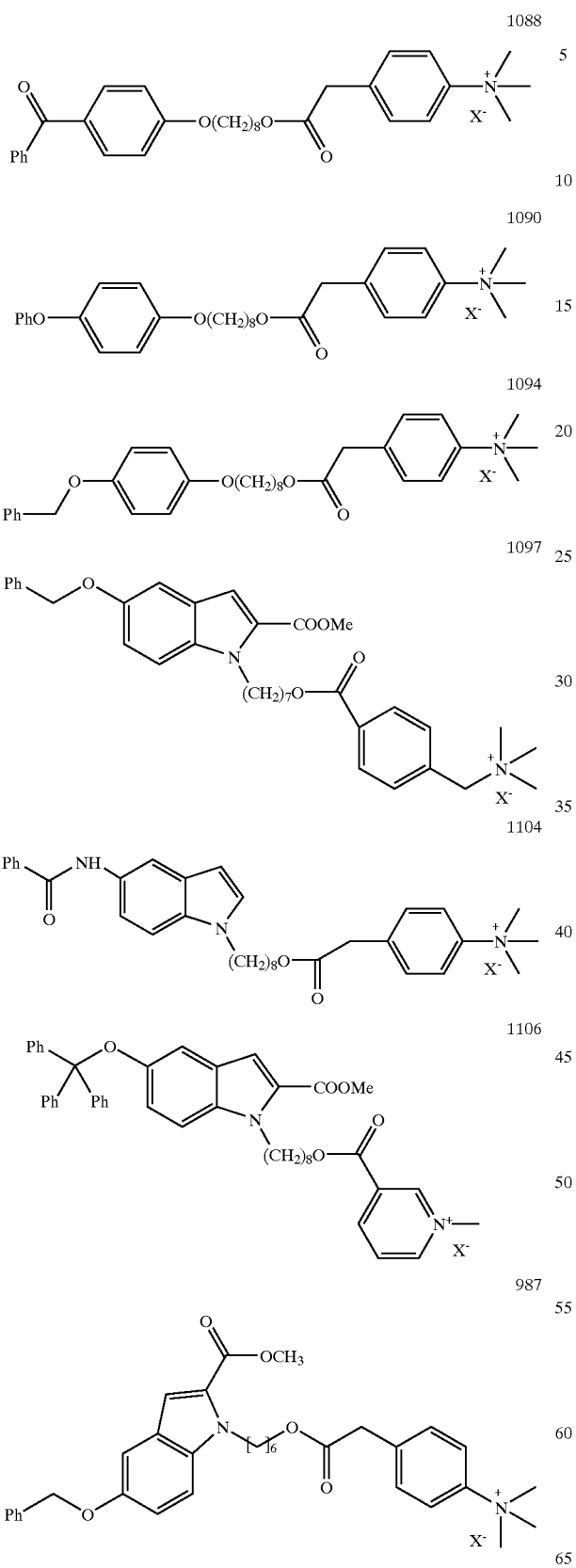

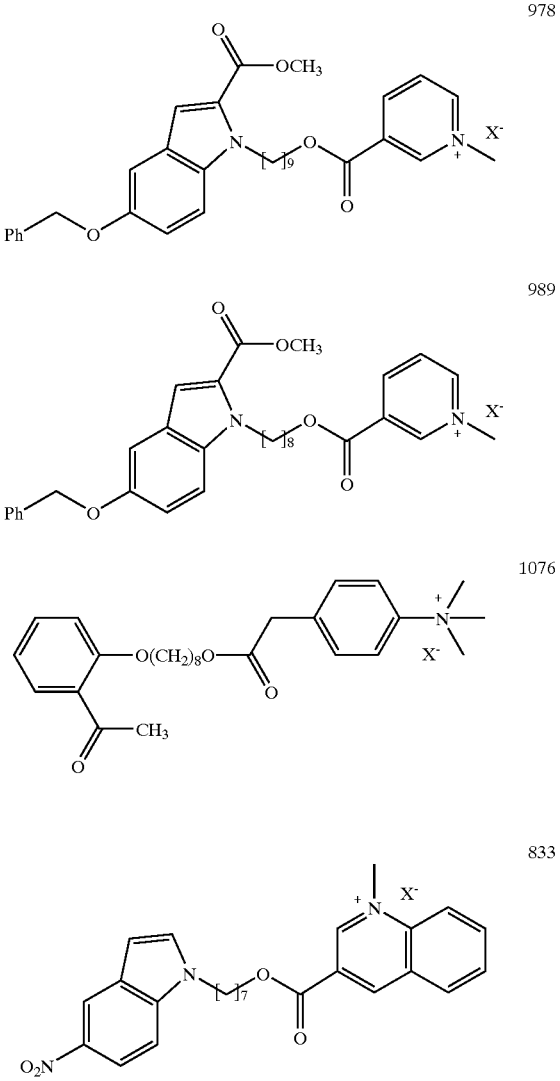

wherein X⁻=F⁻, Cl⁻, Br⁻, I⁻, acetate, or any pharmaceutically acceptable anion.

86. A method of treating or preventing a fungal infection in a host comprising administering to a host a treatment or prevention effective amount of a compound of Structure 2, wherein the prevention is used in a host in need of such treatment or a host susceptible to fungal infections:

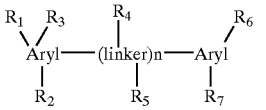

Structure 2 wherein n is an integer of from 1 to 12, $R_1$–$R_7$ each, independently, is H, an unsubstituted or a substituted cyclic or aliphatic group, or a branched or an unbranched group, and wherein the linker is a cyclic or aliphatic, branched or an unbranched alkyl, alkenyl or an alkynyl group and wherein the linker may also contain one or more heteroatoms.

87. A method of killing a yeast or decreasing the growth of a yeast, comprising contacting the yeast with an amount of a compound of Structure 2 effective to reduce or eliminate the production of NAD whereby the yeast is killed or the yeast growth is decreased,
wherein structure is

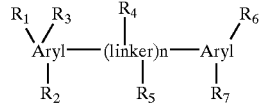

Structure 2 wherein n is an integer of from 1 to 12, $R_1$–$R_7$ each, independently, is an H, an unsubstituted or a substituted cyclic or aliphatic group, or a branched or an unbranched group, and wherein the linker is a cyclic or aliphatic, branched or an unbranched alkyl, alkenyl, or an alkynyl group and wherein the linker may also contain heteroatoms.

* * * * *